United States Patent
Saravolac et al.

(10) Patent No.: US 6,734,171 B1
(45) Date of Patent: *May 11, 2004

(54) METHODS FOR ENCAPSULATING NUCLEIC ACIDS IN LIPID BILAYERS

(75) Inventors: Edward George Saravolac, Vancouver (CA); Yuan-Peng Zhang, Mountain View, CA (US); Jeffery J. Wheeler, Surrey (CA); Pieter R. Cullis, Vancouver (CA); Peter Scherrer, Vancouver (CA); Ljiljana D. Kojic, Vancouver (CA); Olga Ludkovski, Port Coquitlam (CA)

(73) Assignee: Inex Pharmaceuticals Corp., Burnaby (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/169,573

(22) Filed: Oct. 9, 1998

Related U.S. Application Data
(60) Provisional application No. 60/063,473, filed on Oct. 10, 1997.

(51) Int. Cl.[7] ................................................. A61K 48/00
(52) U.S. Cl. ....................... 514/44; 424/450; 435/320.1; 435/455; 435/458
(58) Field of Search ........................ 424/450; 435/325, 435/320.1, 455, 458; 514/44

(56) References Cited

U.S. PATENT DOCUMENTS

| | | | | |
|---|---|---|---|---|
| 4,089,801 A | | 5/1978 | Schneider | 252/316 |
| 4,460,560 A | | 7/1984 | Tokes et al. | 424/1.1 |
| 4,501,728 A | | 2/1985 | Geho et al. | 424/38 |
| 4,544,545 A | | 10/1985 | Ryan et al. | 424/1.1 |
| 4,617,186 A | | 10/1986 | Schafer et al. | 424/78 |
| 4,650,909 A | | 3/1987 | Yoakum | 568/621 |
| 4,728,575 A | | 3/1988 | Gamble et al. | 428/402.2 |
| 4,737,323 A | | 4/1988 | Martin et al. | 264/4.3 |
| 4,752,425 A | | 6/1988 | Martin et al. | 264/4.6 |
| 4,837,028 A | * | 6/1989 | Allen | 424/450 |
| 4,861,521 A | | 8/1989 | Suzuki et al. | 260/403 |
| 4,920,016 A | | 4/1990 | Allen et al. | 424/450 |
| 4,925,661 A | | 5/1990 | Huang | 424/85.91 |
| 4,943,624 A | | 7/1990 | Regen | 528/301 |
| 4,944,948 A | | 7/1990 | Uster et al. | 424/450 |
| 4,963,367 A | | 10/1990 | Ecanow | 424/485 |
| 5,008,109 A | | 4/1991 | Tin | 424/422 |
| 5,013,556 A | | 5/1991 | Woodle et al. | 424/450 |
| 5,064,655 A | | 11/1991 | Uster et al. | 424/450 |
| 5,153,000 A | | 10/1992 | Chikawa et al. | 424/450 |
| 5,185,154 A | | 2/1993 | Lasic et al. | 424/450 |
| 5,206,027 A | | 4/1993 | Kitaguchi | 424/450 |
| 5,288,499 A | | 2/1994 | Janoff et al. | 424/450 |
| 5,356,633 A | | 10/1994 | Woodle et al. | 424/450 |
| 5,395,619 A | | 3/1995 | Zalipsky et al. | 424/450 |
| 5,527,528 A | | 6/1996 | Allen et al. | 424/178.1 |
| 5,552,155 A | | 9/1996 | Bailey et al. | 424/450 |
| 5,593,622 A | | 1/1997 | Yoshioka et al. | 264/4.32 |
| 5,631,237 A | * | 5/1997 | Dzau et al. | 514/44 |
| 5,705,385 A | | 1/1998 | Bally et al. | |
| 5,708,385 A | * | 1/1998 | Shou et al. | 435/320.1 |
| 5,753,262 A | * | 5/1998 | Wyse et al. | 424/450 |
| 5,820,873 A | * | 10/1998 | Choi et al. | 424/283.1 |
| 5,827,703 A | * | 10/1998 | Debs et al. | 435/455 |
| 5,885,613 A | * | 3/1999 | Holland et al. | 424/450 |
| 5,976,567 A | * | 11/1999 | Wheeler et al. | 424/450 |
| 5,981,501 A | | 11/1999 | Wheeler et al. | |
| 2002/0192651 A1 | * | 12/2002 | Wheeler | 435/6 |

FOREIGN PATENT DOCUMENTS

| | | |
|---|---|---|
| CA | 1270197 | 6/1990 |
| CA | 2067133 | 4/1991 |
| CA | 2067178 | 4/1991 |
| CA | 1305054 | 7/1992 |
| EP | 0 118 316 | 3/1983 |
| EP | 0 072 111 | 10/1985 |
| EP | 0 220 797 | 5/1987 |
| EP | 0 370 491 | 5/1990 |
| EP | 0 422 543 | 4/1991 |
| EP | 0 482 860 | 4/1992 |
| EP | 526700 | 2/1993 |
| EP | 546951 | 6/1993 |
| EP | 572049 | 12/1993 |
| EP | 0 445 131 | 4/1994 |
| EP | 0 354 855 | 12/1994 |
| EP | 0 496 813 | 12/1994 |
| EP | 0 496 835 | 5/1995 |
| GB | 2185397 | 7/1987 |
| WO | WO 88/04924 | 7/1988 |
| WO | WO 90/04384 | 5/1990 |
| WO | WO 91/05545 | 5/1991 |
| WO | WO 91/05546 | 5/1991 |
| WO | WO 93/19738 | 10/1993 |
| WO | WO 94/07466 | 4/1994 |
| WO | WO 94/21281 | 9/1994 |
| WO | WO 94/22429 | 10/1994 |
| WO | WO 94/26251 | 11/1994 |
| WO | WO 94/27580 | 12/1994 |
| WO | WO 95/31183 | 11/1995 |
| WO | WO 96/34598 | 11/1996 |
| WO | WO96/37194 | 11/1996 |
| WO | WO96/40964 | 12/1996 |

OTHER PUBLICATIONS

Zelphati et al., Liposomes as a carrier for intracellular delivery of antisense oligonucleotides: a real magic bullet?, 1996, Journal of Controlled Release, vol. 41, pp. 99–119.*

(List continued on next page.)

Primary Examiner—Dave T. Nguyen
(74) Attorney, Agent, or Firm—Townsend & Townsend & Crew LLP

(57) ABSTRACT

The present invention relates to lipid-based formulations for nucleic acid delivery to cells, methods for the preparation of such formulations and, in particular, to lipid encapsulated plasmids. The compositions are safe and practical for clinical use. In addition, the present invention provides methods for introducing nucleic acids into cells and for inhibiting tumor growth in cells using such lipid-nucleic acid formulations.

19 Claims, 31 Drawing Sheets-

OTHER PUBLICATIONS

Filion et al., Major limitations in the use of cationic liposomes for DNA delivery, 1998, International Journal of Pharmaceutics, vol. 192, pp. 159–170.*

Branch, A good antisense molecule is hard to find, Feb. 1998, TIBS, vol. 23, pp. 45–50.*

Anderson, Human gene therpy, Apr. 30, 1998, Nature, vol. 392, pp. 25–30.*

Verma et al. Gene therapy –promises, problems and propespects, Sep. 18, 1997, Nature, vol. 389, pp. 239–242.*

Abuchowski, et al., "Treatment of L5178Y Tumor–Bearing BDF Mice With a Nonimmunogenic L–Gutaminase–L–Asparginase," Cancer Treatment Reports, 63(6):1127–1132 (1979).

Abuchowski, et al., "Immunosuppressive Properties and Circulating Life of Achromobacter Glutaminase–Asparaginase Covalently Attached to Polyethylene Glycol in Man," Cancer Research Reports, 65(11–12):1077–1081 (1981).

Berger, Jr., et al., "Preparation of Polyethylene Glycol–tissue Plasminogen Activator Adducts That Retain Functional Activity: Characteristics and Behavior in Three Animal Species," Blood, 71(6):1641–1647 (1988).

Blume, et al., "Specific targeting with poly(ethylene glycol)–modified liposomes: coupling of homing devices to the ends of the polymeric chains combines effective target binding with long circulation times," 1993, Biochimica et Biophysica Acta., 1149:180–184.

Chonn, et al., "Ganglioside $G_{M1}$ and hydrophilic polymers increases liposome circulation times by inhibiting the association of blood proteins," 1992, J. Liposome Res., 2(3):397–410.

Danishefsky, et al., "Total Synthesis of Zincophorin," 1988, J. Am. Chem. Soc., 1988, 110:4368–4378.

Gregoriadis, et al., "Coupling of ligands to liposomes independently of solute entrapment; observations on the formed vesicles," 1993, Biochimica et Biophysica Acta., 1147:185–193.

Huang, et al., "Extravasation and Transcytosis of Liposomes in Kaposi's Sarcom–Like Dermal Lesions Transgenic Mice Bearing the HIV Tat Gene," 1993, American Journal of Pathology, 143(1):10–14.

Hyde, et al., "Correction of the ion transport defect in cycstic fibrosis transgenic mice by gene therapy," 1993, Nature, 362:250–255.

Kiso, et al., "A Convenient Synthesis of Sphingosine and Ceramide from D–Xylose or D–Glactose," 1986, J. Carbohydrate Chemistry, 5(2):335–340.

Klibanov, et al., "Activity of amphipathic poly(ethylene glycol) 5000 to prolong the circulation time of liposomes depends on the liposome size and is unfavorable for immunoliposome binding to traget," 1991, Biochimica et Biophysica Acta., 1062:142–148.

Liu, et al., "Role of liposome size and RES blockade in controlling biodistribution and tumor uptake of $GM_1$–containing liposomes," 1992, Biochimica et Biophysica Acta., 1104:95–101.

Mori, et al., "Influence of the steric barrier activity of amphipathic poly(ethyleneglycol) and ganglioside $GM_1$ on the circulation time of liposomes and on the target binding of immunoliposomes in vivo," 1991, FEBS Letters, 284(2):263–266.

Nicolaou, et al., "A Practical and Enantioselective Synthesis of Glycosphingolipids and Related Compounds. Total Synthesis of Globotriaosylceramide ($Gb_3$)," 1988, J. Am. Chem. Soc., 110:7910–7912.

Oikawa, et al., "Selective hydrogenolysis of the benzyl protecting group for hydroxy function with Raney nickel in the presence of the MPM (4–methoxybenzyl) and DMPM (3,4–dimethoxybenzyl) protecting groups," 1984, Tetrahedron Letters, 25(47):5397–5400.

Parr, et al., "Factors influencing the retention and chemical stability of poly(ethylene glycol)–lipid conjugates incorporated into large unilamellar vesicles," Jun. 19–22, 1994, Liposome Research Days Conference—Liposomes: The Next Generation, University of British Columbia.

Parr, et al., "Factors influencing the retention and chemical stability of poly(ethylene glycol)–lipid conjugates incorporated into large unilamellar vesicles," 1994, Biochimica et Biophysica Acta, 1195:21–30.

Reed, et al., "Generation of targets for alloreactive CTL using purified $H-2K^k$ in liposomes and polyethylene glycol," 1986, Molecular Immunology, 23(12):1339–1347.

Schmidt, et al., "Lactosylceramides with Unsaturated Fatty Acids—Synthesis and Use in the Generation of Bilayer Membranes," 1987, Angew. Chem. Int. Ed. Engl., 26(8):793–794.

Torchilin, et al., "Targeted accumulation of polyethylene glycol–coated immunoliposomes in infarcted rabbit myocardium," 1992, The FASEB Journal , 6:2716–2719.

Wang, et al., "pH–sensitive immunoliposomes mediate target–cell–specific delivery and controlled expression of a foreign gene in mouse," 1987, Proc. Natl. Acad. Sci. USA, 84:7851–5855.

Allen, T., Journal of Liposome Research, 2(3):289–305 (1992).

Chu et al., Journal of Liposome Research, 4(1):361–395 (1994).

Gao, et al., Journal of Liposome Research, 3(1):17–30 (1993).

Klibanov, et al., Journal of Liposome Research, 2(3):321–334 (1992).

Soehnlein, et al., Seifen, Ole, Fette, Wachse, 115(3):85–86 (1989).

* cited by examiner

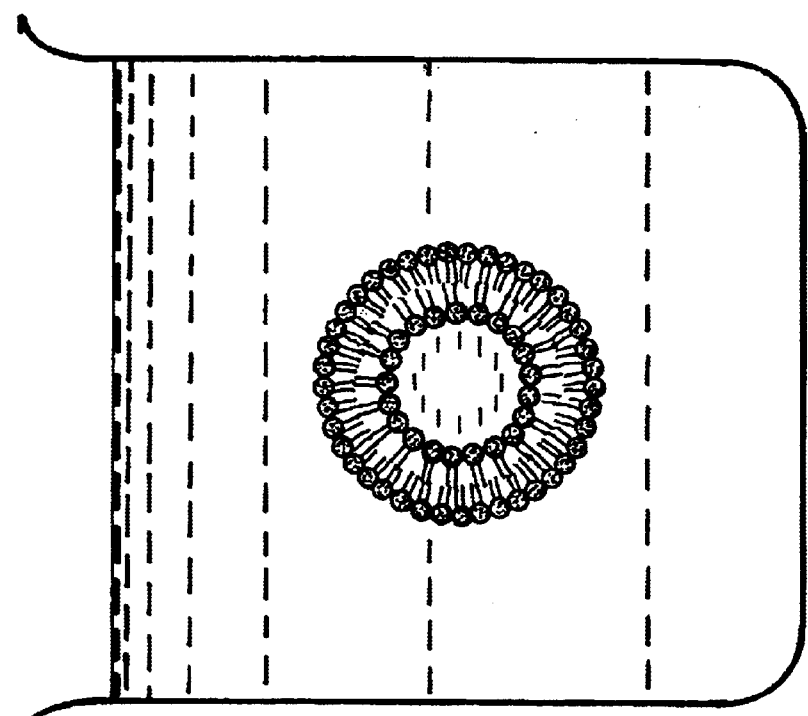
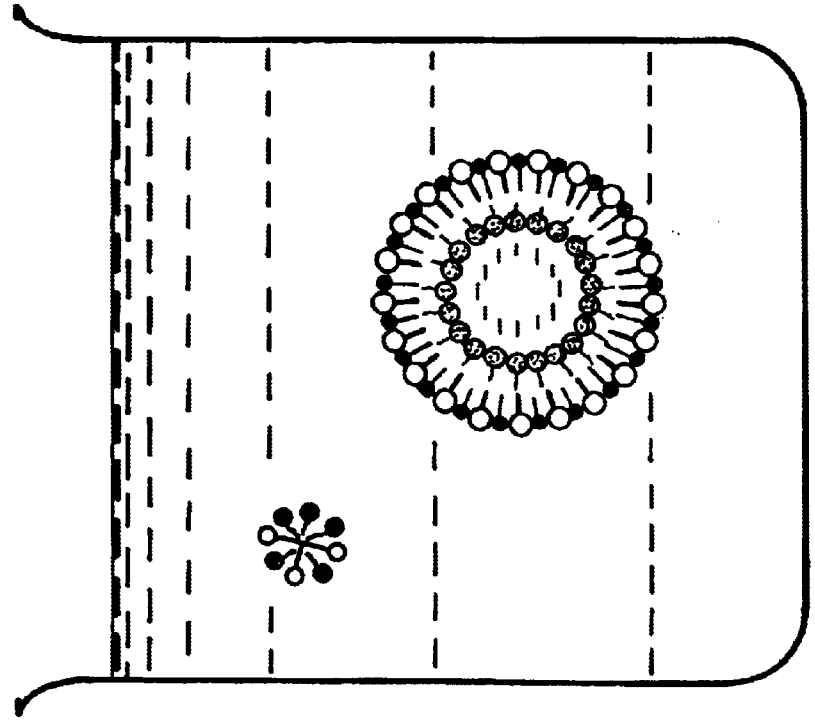
FIG. 3.

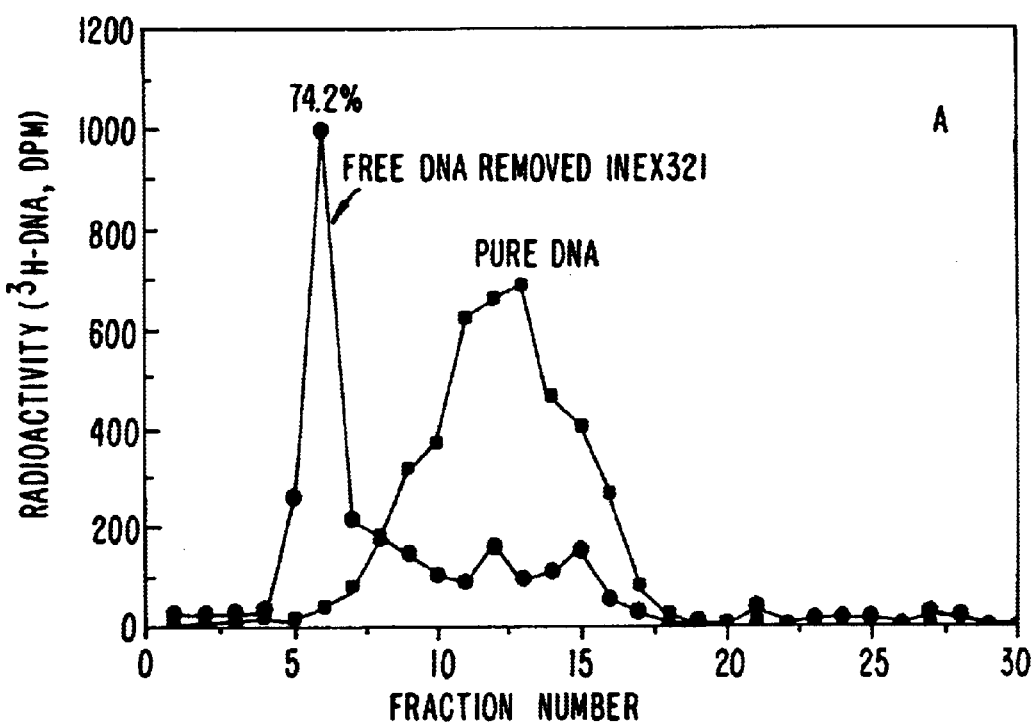
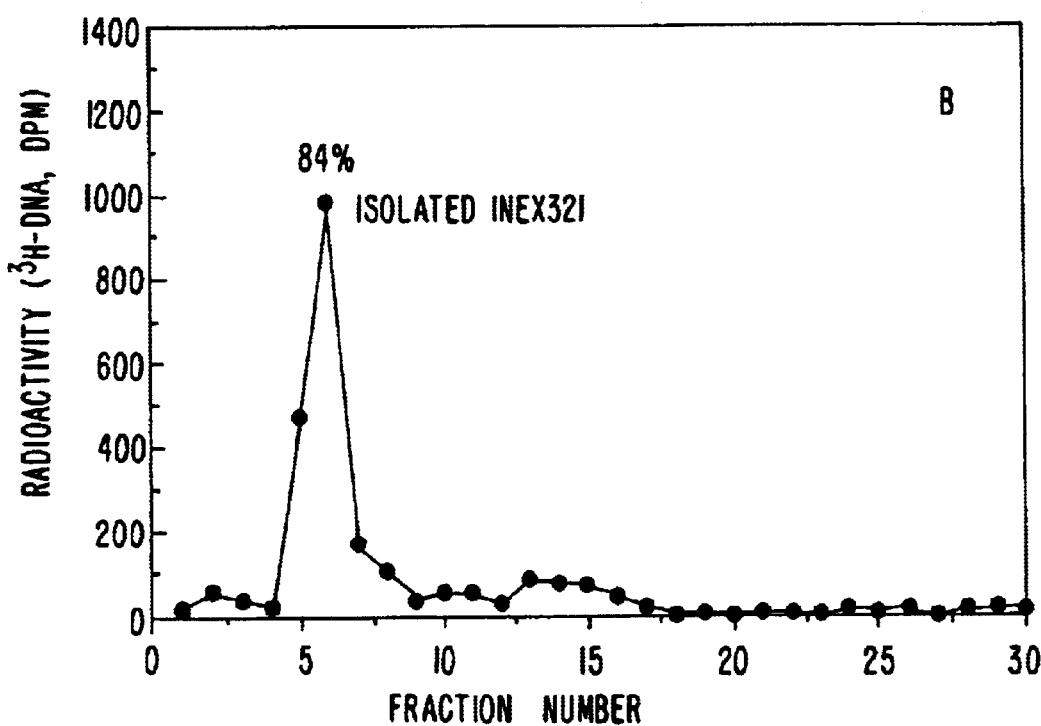
FIG. 15.

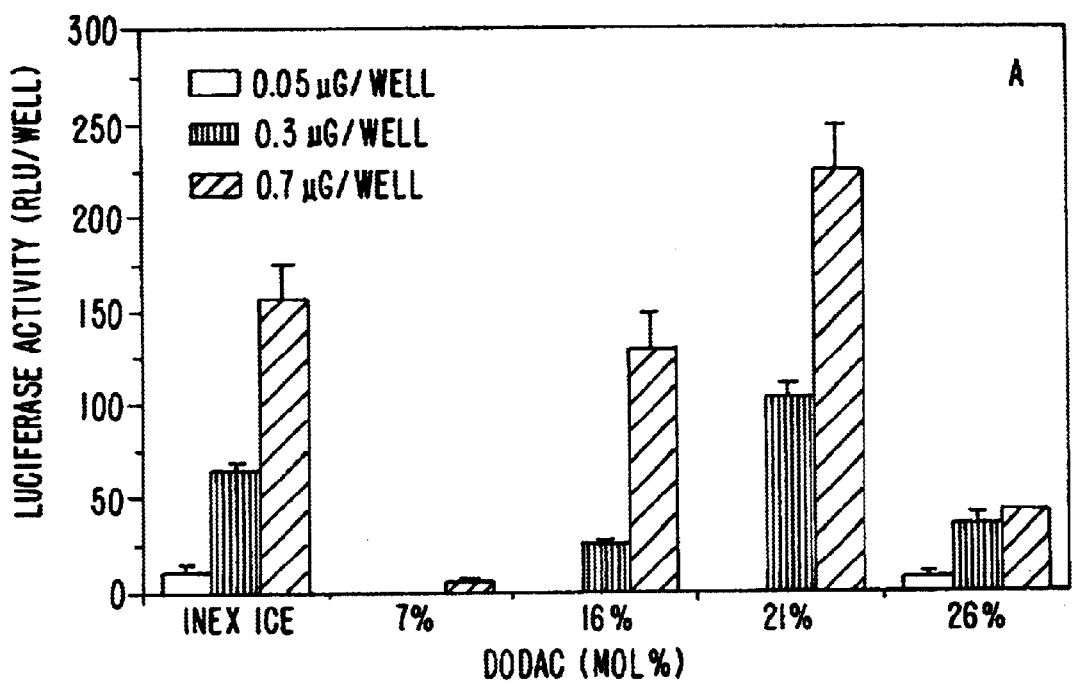
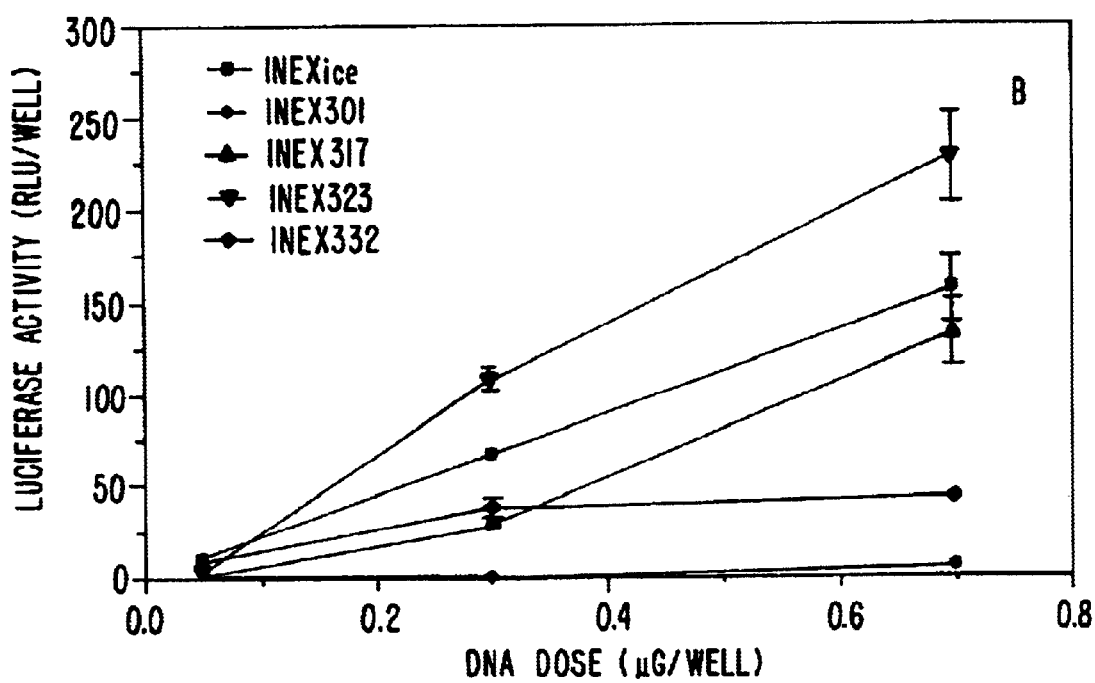
FIG. 19.

METHODS FOR ENCAPSULATING NUCLEIC ACIDS IN LIPID BILAYERS

CROSS-REFERENCE TO RELATED APPLICATION

This application claims priority under 119(e) to U.S. Provisional Patent Application Serial No. 60/063,473, filed on Oct. 10, 1997, which is hereby incoporated by reference.

FIELD OF THE INVENTION

This invention relates to lipid-based formulations for nucleic acid delivery to cells, methods for the preparation of such formulations and, in particular, to lipid encapsulated plasmids. The compositions are safe and practical for clinical use.

BACKGROUND OF THE INVENTION

Gene therapy is an area of current interest which involves the introduction of genetic material into a cell to facilitate expression of a deficient protein. Plasmid DNA has been encapsulated or complexed with lipid-based carriers by a number of methods including reverse phase evaporation (Fraley, et al., *J. Biol. Chem.*, 255:10431–10435 (1980); Soriano, et al., *Proc. Natl. Acad. Sci. USA*, 80:7128–7131 (1983); Nakanishi, et al., *Exper. Cell Res.*, 159:399–409 (1985); Nandi, et al., *J. Biol. Chem.*, 261:16722–16726 (1986); and Alino, et al., *Biochem. Biophys. Res. Commun.*, 192:174–181 (1993)); $Ca^{2+}$ EDTA chelation (Szelei, et al., *Biochem. J.*, 259:549–553 (1989)); detergent dialysis (Wang, et al., *Proc. Natl. Acad. Sci. USA*, 84:7851–7855 (1987)); lipid hydration (Lurquin, *Nucleic Acids Res.*, 6:3773–3784 (1979); Yagi, et al., *Biochem. Mol. Biol. International*, 32:167–171 (1994)); ether injection (Fraley, et al., *Proc. Natl. Acad. Sci.*, 76:3348–3352 (1979); Nicolau, et al., *Biochem. Biophys. Res. Comm.*, 108:982–986 (1982)); and sonication (Jay, et al., *Bioconj. Chem.*, 6:187–194 (1987) and Puyal, et al., *Eur. J. Biochem.*, 228:697–703 (1993)).

Reverse phase techniques typically encapsulate only about 10 to 20% of DNA in solution and the final DNA to lipid ratio is quite low. For example, Nakanishi, et al. (*Exper. Cell Res.*, 159:399–409 (1985)) reported a final DNA to lipid ratio of 1.5 μg DNA to 2.5 mg lipid, while Soriano, et al. (*Proc. Natl. Acad. Sci. USA*, 80:7128–7131 (1983)) reported a DNA to lipid ratio of about 14 μg DNA to 60 μmol of lipids. The maximum theoretical encapsulation efficiency expected by reverse phase is only about 40%. Other methods, such as rehydration of freeze dried vesicles with DNA, have been shown to yield trapping efficiencies between 30 and 40% (Baru, et al., *Gene*, 161:143–150 (1995)). Others have sought to increase the entrapment of DNA by the inclusion of cationic lipids in the lipid suspension (Stavridis, et al., 1986; Puyal, et al., *Eur. J. Biochem.*, 228:697–703 (1995)), or by rendering the DNA positively charged by 10 coating it with basic proteins such as lysozymes (Jay, et al., *Proc. Natl. Acad. Sci. USA*, 84:1978–1980 (1987)). Although trapping efficiencies as high as 50% were achieved by the lysozyme method, the amount of DNA loaded per mg of lipid was low (5 μg/mg lipid) and the largest DNA molecule tested was only 1 kb. Trapping efficiencies as high as 60–90% were achieved by Puyal, et al. (*Eur. J. Biochem.*, 228:697–703 (1995)) with a higher DNA to lipid ratio (13 μg/μmole lipid) using a 6.3 kb ssDNA (M13 phage). The major drawback of this technique and the one described by Jay, et al., *Bioconj. Chem.*, 6:187–194 (1987)) is that sonication was used. Sonication of DNA typically leads to some degradation of the lipid vesicle.

Detergent dialysis is a method of encapsulation which has no deleterious effects on the DNA. Wang, et al., *Proc. Natl. Acad. Sci. USA*, 84:7851–7855 (1987) applied a detergent dialysis technique followed by extrusion through a 0.2 μm polycarbonate filter. A 4.6 kb plasmid was entrapped in vesicles approximately 200 nm in diameter with a trapping efficiency of about 14–17%, giving a DNA to lipid ratio of about 26 μg DNA to 10 μmole lipid.

Ideally, a delivery vehicle for a nucleic acid or plasmid will have the following characteristics: a) small enough and long lived enough to distribute from local injection sites when given intravenously, b) capable of carrying a large amount of DNA per particle to enable transfection of all sizes of genes and to reduce the volume of injection, c) homogeneous, d) reproducible, e) protective of DNA from extracellular degradation and f) capable of transfecting target cells in such a way that the DNA is not digested intracellularly.

The present invention provides such compositions and methods for their preparation and use.

SUMMARY OF THE INVENTION

In one aspect, the present invention provides compositions which are nucleic acid (e.g., plasmid)-lipid compositions. In these compositions, a nucleic acid (e.g., plasmid or an antisense molecule) is encapsulated in a self-assembling lipid vesicle in an amount of from about 20 μg nucleic acid/mg lipid to about 400 μg nucleic acid/mg lipid. The lipid vesicle will typically be a liposome or lipid particle (a bilayer vehicle coating the plasmid and having little or no aqueous interior). The lipid vesicle can be prepared from a wide variety of lipids or combinations of lipids. The compositions can also include targeting groups and modified lipids (e.g., ATTA-lipids, gangliosides, such as ganglioside $G_{M1}$), PEG-lipids, such as PEG-ceramides, and lipids having reactive functional groups for the attachment of targeting groups or circulation stabilizers). Preferably, the lipid vesicles will comprise cationic lipids and fusogenic lipids. Additionally, the nucleic acid (e.g., plasmid)-lipid compositions described herein can be prepared having a narrow size distribution (typically 50 nm to about 150 nm) without the use of sizing methods, such as extrusion and sonication methods.

In another aspect, the present invention provides methods for the encapsulation of nucleic acids, antisense, ribozymes and, particularly, plasmids in a lipid bilayer carrier. Such methods are related to a detergent dialysis method using cationic lipids of any desired concentration in combination with a dialysis buffer of an ionic strength (salt concentration, type of ions) specific for the given cationic lipid concentration. With the dialysis buffer of appropriate ionic strength, the methods provide encapsulation of 40–80% of the nucleic acid solution. The compositions above, and those formed by the methods described below, exhibit preferably less than about 30% degradation, more preferably, less than about 15% degradation and, even more preferably, less than about 5% degradation when digested with 0.1 to 10 U and, more preferably, 1 U of a nuclease after 30 minutes at 37° C.

In particular, the invention provides a method for encapsulating a nucleic acid in a lipid bilayer carrier, comprising:

(a) combining a nucleic acid with a lipid-detergent mixture comprising an aggregation-preventing agent (e.g., an ATTA-lipid, a PEG-lipid, such as a PEG-ceramide, a ganglioside, etc.) in an amount of about 5 mol % to about 20 mol %, cationic lipids in an amount of about 0.5 mol % to about 50 mol % by weight, neutral or fusogenic lipids in an amount of from about 30 mol % to about 70 mol % and a detergent, to provide a nucleic acid-lipid-detergent mixture; and (b) dialyzing the nucleic acid-lipid-detergent mixture against a buffered salt solution and to encapsulate the nucleic acid in a lipid bilayer carrier. In these methods, the ionic strength (salt concentration) is adjusted for the cationic lipid concentration used in the lipid mixture and when necessary for the polynucleotide selected for encapsulation to entrap from about 40% to about 80% of the nucleic acid for any given concentration of cationic lipid.

In another aspect, the present invention provides methods for introducing nucleic acids into cells and for inhibiting tumor growth in cells using the lipid-nucleic acid formulations described above.

Other features, objects and advantages of the invention and its preferred embodiments will become apparent from the detailed description which follows.

BRIEF DESCRIPTION OF THE DRAWINGS

FIG. 3 provides an illustration of the detergent dialysis procedure for entrapping nucleic acids in fusogenic lipid vesicles.

FIG. 15. Serum stability assay of INEX TCS. Sepharose CL-4B gel filtration chromatography after treatment with 80% normal mouse serum at 37° C. for 60 minutes. Upper panel: free DNA vs. TCS containing 21 mol % DODAC (unencapsulated DNA removed). Lower panel: TCS containing 21 mol % DODAC after isolation on a sucrose density gradient. TCS when not incubated with serum, or incubated but protected from serum degradation was eluded at the void volume (fractions 5–8). DNA when degraded by serum was eluded in later fractions (fractions #10–20). The results showed that DNA was protected 74% and 84% in the cleaned TCS (by DEAE column) and the isolated TCS respectively.

FIG. 19. Effect of dose on the transfection of Hep-G2 cells in culture in isolated TCS prepared with pINEXL018 and DODAC/DOPE/PEG-Cer-C8 by the detergent dialysis method using citrate buffer. Cells (40,000/well) were seeded in 24 well plates 24 hr before transfection. The doses were 0.05, 0.3 & 0.7 μg/well and the luciferase activity was assayed at 48 hr time point (n=3). INEXice represents complexes prepared by mixing DODAC/DOPE liposomes with pINEXL018.

DETAILED DESCRIPTION OF THE INVENTION

CONTENTS

Figure 1:
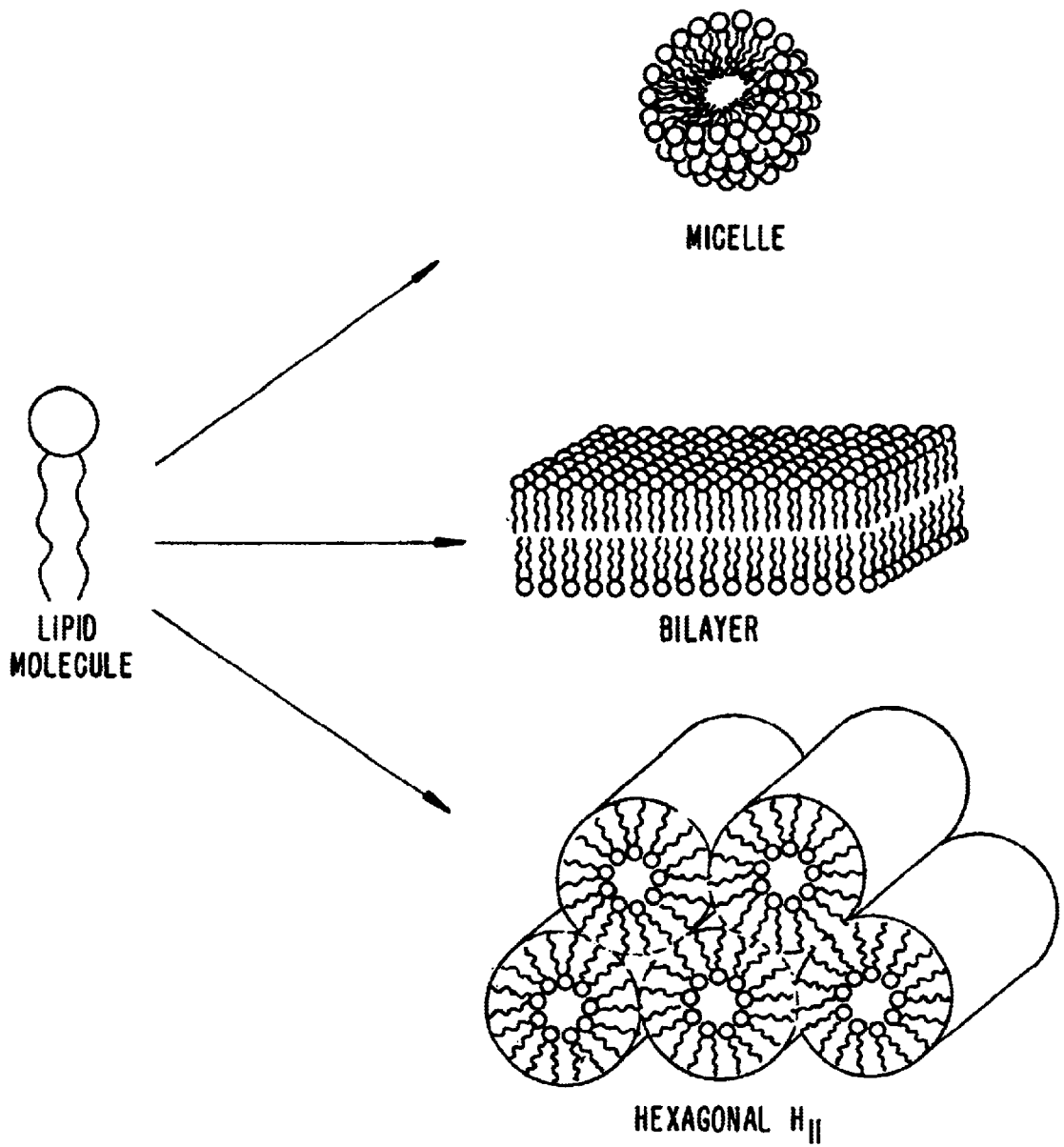
FIG. 1 provides an illustration of the phase properties of lipids.

I. Glossary
II. General—Plasmid-Lipid Compositions
III. Methods of Forming Plasmid-Lipid Particles
IV. Pharmaceutical Preparations
V. Administration of Plasmid-Lipid Particle Formulations
VI. Example 1
VII. Example 2
VIII. Conclusion

I. Glossary

The following abbreviations are used herein: DC-Chol, 3β-(N-(N',N'-dimethylaminoethane)carbamoyl)cholesterol (see, Gao, et al., *Biochem. Biophys. Res. Comm.*, 179:280–285 (1991)); DDAB, N,N-distearyl-N,N-dimethylammonium bromide; DMRIE, N-(1,2-dimyristyloxyprop-3-yl)-N,N-dimethyl-N-hydroxyethyl ammonium bromide; DODAC, N,N-dioleyl-N,N-dimethylammonium chloride (see, commonly owned patent application U.S. Ser. No. 08/316,399, incorporated herein by reference); DOGS, diheptadecylamidoglycyl spermidine; DOPE, 1,2-sn-dioleoylphoshatidyethanolamine; DOSPA, N-(1-(2,3-dioleyloxy)propyl)-N-(2-(sperminecarboxamido)ethyl)-N,N-dimethylammonium trifluoroacetate; DOTAP, N-(1-(2,3-dioleyloxy)propyl)-N,N,N-trimethylammonium chloride; DOTMA, N-(1-(2,3-dioleyloxy)propyl)-N,N,N-trimethylammonium chloride; EPC, egg phosphatidylcholine; RT, room temperature; HEPES, 4-(2-hydroxyethyl)-1-piperazineethanesulfonic acid; HBS, HEPES buffered saline (150 mM NaCl and 20 mM HEPES); PEG-Cer-$C_{20}$, 1-O-(2'-(ω-methoxypolyethyleneglycol)succinoyl)-2-N-arachidoyl-sphingosine; PEG-Cer-$C_{14}$, 1-O-(2'-(ω-methoxypolyethyleneglycol)succinoyl)-2-N-myristoyl-sphingosine; PBS, phosphate-buffered saline; EGTA, ethylenebis(oxyethylenenitrilo)-tetraacetic acid; OGP, n-octyl β-D-glycopyranoside (Sigma Chemical Co., St. Louis, Mo.); POPC, palmitoyl oleoyl phosphatidylcholine (Northern Lipids, Vancouver, BC); QELS, quasielastic light scattering; TBE, 89 mM Tris-borate with 2 mM EDTA; and EDTA, Ethylenediaminetetraacetic acid (Fisher Scientific, Fair Lawn, N.J.);

The term "acyl" refers to a radical produced from an organic acid by removal of the hydroxyl group. Examples of acyl radicals include acetyl, pentanoyl, palmitoyl, stearoyl, myristoyl, caproyl and oleoyl.

The term "lipid" refers to any fatty acid derivative which is capable of forming a bilayer such that a hydrophobic portion of the lipid material orients toward the bilayer while a hydrophilic portion orients toward the aqueous phase. Hydrophilic characteristics derive from the presence of phosphato, carboxylic, sulfato, amino, sulfhydryl, nitro, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic group(s). Preferred lipids are phosphoglycerides and sphingolipids, representative examples of which include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidyl-ethanolamine, dipalmitoylphosphatidylcholine, dioleoylphosphatidylcholine, distearoyl-phosphatidylcholine or dilinoleoylphosphatidylcholine could be used. Other compounds lacking in phosphorus, such as sphingolipid and glycosphingolipid families are also within the group designated as lipid. Additionally, the amphipathic lipids described above may be mixed with other lipids including triglycerides and sterols.

The term "cationic lipid" refers to any of a number of lipid species which carry a net positive charge at physiological pH or have a protonatable group and are positively charged at pH lower than the $pK_a$. Such lipids include, but are not limited to, DODAC, DOTMA, DOGS, DDAB, DOTAP, DC-Chol, DMRIE and amino lipids. The term "amino lipids" is meant to include lipids with an amino head group (including alkylamino or dialkylamino group) which is protonated to form a cationic lipid below its $pK_a$. Commercial preparations of cationic liposomes prepared from cationic lipids are generally not useful unless the liposomes are first disrupted to provide lipid mixtures. The compositions and methods described herein use lipids and lipid mixtures in a self-assembling process which occurs in the presence of a plasmid or other nucleic acid.

The terms "transfection" and "transformation" are used herein interchangeably, and refer to the introduction of polyanionic materials, particularly nucleic acids and plasmids, into cells. The term "lipofection" refers to the introduction of such materials using liposome or lipid-based complexes. The polyanionic materials can be in the form of DNA or RNA which is linked to expression vectors to facilitate gene expression after entry into the cell. The plasmids used in the present invention include DNA having coding sequences for structural proteins, receptors and hormones, as well as transcriptional and translational regulatory elements (i.e., promoters, enhancers, terminators and signal sequences) and vectors. Methods of incorporating particular nucleic acids into expression vectors are well known to those of skill in the art, but are described in detail in, for example, Sambrook, et al., *Molecular Cloning: A Laboratory Manual* (2nd ed.), Vols. 1–3, Cold Spring Harbor Laboratory, (1989) or *Current Protocols in Molecular Biology*, F. Ausubel, et al., ed. Greene Publishing and Wiley-Interscience, New York (1987), both of which are incorporated herein by reference.

The term "contacting" is used herein interchangeably with the following: combined with, added to, mixed with, passed over, incubated with, flowed over, etc. Moreover, the compounds of present invention can be "administered" by any conventional method such as, for example, parenteral, oral, topical and inhalation routes as described herein.

"An amount sufficient," "an effective amount," or "therapeutically effective amount" refer to an amount of a compound or composition effective to depress, suppress or regress cell growth or result in amelioration of symptoms associated with cancerous diseases. The desired result can be either a subjective relief of a symptom(s) or an objectively identifiable improvement in the recipient of the dosage, a decrease in tumor size, a decrease in the rate of growth of cancer cells as noted by the clinician or other qualified observer.

The terms "treating cancer," "therapy," and the like refer generally to any improvement in the mammal having the cancer wherein the improvement can be ascribed to treatment with the compounds and compositions of the present invention. The improvement can be either subjective or objective. For example, if the mammal is human, the patient may note improved vigor or vitality or decreased pain as subjective symptoms of improvement or response to therapy. Alternatively, the clinician may notice decrease in tumor size or tumor burden based on physical exam, laboratory parameters, tumor markers or radiographic findings. Some laboratory signs that the clinician may observe for response to therapy include normalization of tests such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement such as sonograms, nuclear magnetic resonance testing and positron emissions testing.

"Inhibiting the growth of tumor cells" can be evaluated by any accepted method of measuring whether growth of the tumor cells has been slowed or diminished. This includes direct observation and indirect evaluation such as subjective symptoms or objective signs as discussed above.

"Expression vectors," "cloning vectors," or "vectors" are often plasmids or other nucleic acid molecules that are able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in a mammalian cell for expression.

H. General—Plasmid-Lipid Compositions

The present invention derives from the discovery that nucleic acid (e.g., plasmid) can be encapsulated in lipid bilayer carriers in an amount significantly above that which has been previously demonstrated. In particular, the present invention provides lipid-plasmid compositions in which nucleic acids are encapsulated in self-assembling lipid vesicles in an amount of from about 5 $\mu$g to about 800 $\mu$g per milligram of lipid, preferably in an amount of from about 40 $\mu$g to about 400 $\mu$g per milligram of lipid and, more preferably, in an amount of from about 100 $\mu$g to about 400 $\mu$g per milligram of lipid. Additionally, the nucleic acid-lipid compositions which are described herein, form in a self-assembling process to yield particles having a narrow distribution of sizes (e.g., 50 nm to about 150 nm). The precise size of the compositions formed will depend on several factors including, for example, the choice of lipids and the size of the nucleic acid that is encapsulated. However, the size distribution is relatively narrow and is achieved without harsh sizing steps such as, for example, extrusion or sonication. Still further, the compositions described herein are nuclease resistant and can be concentrated in an aqueous solution without the formation of aggregate complexes. As used herein, the term "nuclease resistant" when used to describe a nucleic acid-lipid composition refers to a composition in which the nucleic acid portion is less than about 30% degraded, more preferably, less than about 15% degraded and, even more preferably, less than about 5% degraded when the composition is incubated with 0.1 to 10 U and, more preferably, 1 U of a nuclease (e.g., DNAse or normal serum) after 30 minutes at 37° C.

More particularly, it has now been discovered that encapsulation efficiency in detergent dialysis methods is dependent on the lipid composition as well as the dialysis buffer which is used in forming the lipid bilayer carriers. Optimal lipid bilayer carriers can now be constructed depending on the encapsulate (e.g., plasmid, antisense, ribozyme or other polyanionic therapeutic agent), the environment for transfection (e.g., diagnostics or in vivo or in vitro transfection) and other factors such as desired circulation lifetimes and fusogenic properties. Accordingly, particular lipid compositions can now be selected to exhibit certain circulation and targeting characteristics and formulated by control of salt concentrations to increase the amounts of plasmid or other nucleic acid which are encapsulated.

The unique detergent dialysis method by which the present compositions are prepared yields DNA to lipid ratios in excess of 20 $\mu$g DNA to 1 mg lipid. In some embodiments, the lipid coated DNA particle will have DNA to lipid ratios in excess of 200 $\mu$g DNA to 1 mg lipid.

Plasmids which are useful for the instant compositions are typically nucleotide polymers which are to be administered to a subject for the purpose of repairing or enhancing the expression of a cellular protein. Accordingly, the nucleotide polymers can be polymers of nucleic acids including genomic DNA, cDNA, or mRNA. Still further, the plasmids can encode promoter regions, operator regions, structural regions, etc. The plasmids are preferably double-stranded DNA or DNA-RNA hybrids. Examples of double-stranded DNA include, but are not limited to, structural genes, genes including operator control and termination regions, and self-replicating systems such as plasmid DNA.

Multiple genetic sequences can also be used in the present compositions. Thus, the sequences for different proteins can be located on one strand or plasmid. Promoter, enhancer, stress or chemically-regulated promoters, antibiotic-sensitive or nutrient-sensitive regions, as well as therapeutic protein encoding sequences, can be included as required. Nonencoding sequences can be also be present to the extent they are necessary to achieve appropriate expression.

Plasmids used in the present method can be isolated from natural sources, obtained from such sources as ATCC or GenBank libraries or prepared by synthetic methods. The compositions of the present invention can be prepared from plasmids of essentially any size. In preferred embodiments, the plasmid is from about 2 kilobases to about 15 kilobases, more preferably from about 4 kilobases to about 10 kilobases.

In some embodiments, the plasmid will be replaced with other nucleic acids (e.g., single-stranded DNA or RNA, antisense, ribozymes or nucleic acids). When nucleic acids other than plasmids are used, the nucleic acids can contain nucleic acid analogs, for example, the antisense derivatives described in a review by Stein, et al., *Science* 261:1004–1011 (1993) and in U.S. Pat. Nos. 5,264,423 and 5,276,019, the disclosures of which are incorporated herein by reference.

Single-stranded nucleic acids include antisense oligonucleotides (complementary to DNA and RNA), ribozymes and triplex-forming oligonucleotides. In order to have prolonged activity, the single-stranded nucleic acids will preferably have some or all of the nucleotide linkages substituted with stable, nonphosphodiester linkages, including, for example, phosphorothioate, phosphorodithioate, phophoroselenate, or O-alkyl phosphotriester linkages.

The nucleic acids used in the present invention will also include those nucleic acids in which modifications have been made in one or more sugar moieties and/or in one or more of the pyrimidine or purine bases. Examples of sugar modifications include replacement of one or more hydroxyl groups with halogens, alkyl groups, amines, azido groups or functionalized as ethers or esters. Additionally, the entire sugar can be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Caruthers, et al., U.S. Pat. Nos. 4,458,066 and 4,500,707; Beaucage, et al., *Tetrahedron Lett.*, 22:1859–1862 (1981); Matteucci, et al., *J. Am. Chem. Soc.*, 103:3185–3191 (1981); Caruthers, et al., *Genetic Engineering*, 4:1–17 (1982); Jones, chapter 2, Atkinson, et al., chapter 3, and Sproat, et al., chapter 4, in *Oligonucle-* *otide Synthesis: A Practical Approach*, Gait (ed.), IRL Press, Washington D.C. (1984); Froehler, et al., *Tetrahedron Lett.*, 27:469–472 (1986); Froehler, et al., *Nucleic Acids Res.*, 14:5399–5407 (1986); Sinha, et al. *Tetrahedron Lett.*, 24:5843–5846 (1983); and Sinha, et al., *Nucl. Acids Res.*, 12:4539–4557 (1984) which are incorporated herein by reference.

Lipids which are useful in the present invention can be any of a variety of lipids including both neutral lipids and charged lipids. Carrier systems having desirable properties can be prepared using appropriate combinations of lipids, targeting groups and circulation enhancers. Additionally, the compositions provided herein can be in the form of liposomes or lipid particles, preferably lipid particles. As used herein, the term "lipid particle" refers to a lipid bilayer carrier which "coats" a nucleic acid and has little or no aqueous interior. More particularly, the term is used to describe a self-assembling lipid bilayer carrier in which a portion of the interior layer comprises cationic lipids which form ionic bonds or ion-pairs with negative charges on the nucleic acid (e.g., a plasmid phosphodiester backbone). The interior layer can also comprise neutral or fusogenic lipids and, in some embodiments, negatively charged lipids. The outer layer of the particle will typically comprise mixtures of lipids oriented in a tail-to-tail fashion (as in liposomes) with the hydrophobic tails of the interior layer. The polar head groups present on the lipids of the outer layer will form the external surface of the particle.

Figure 2:
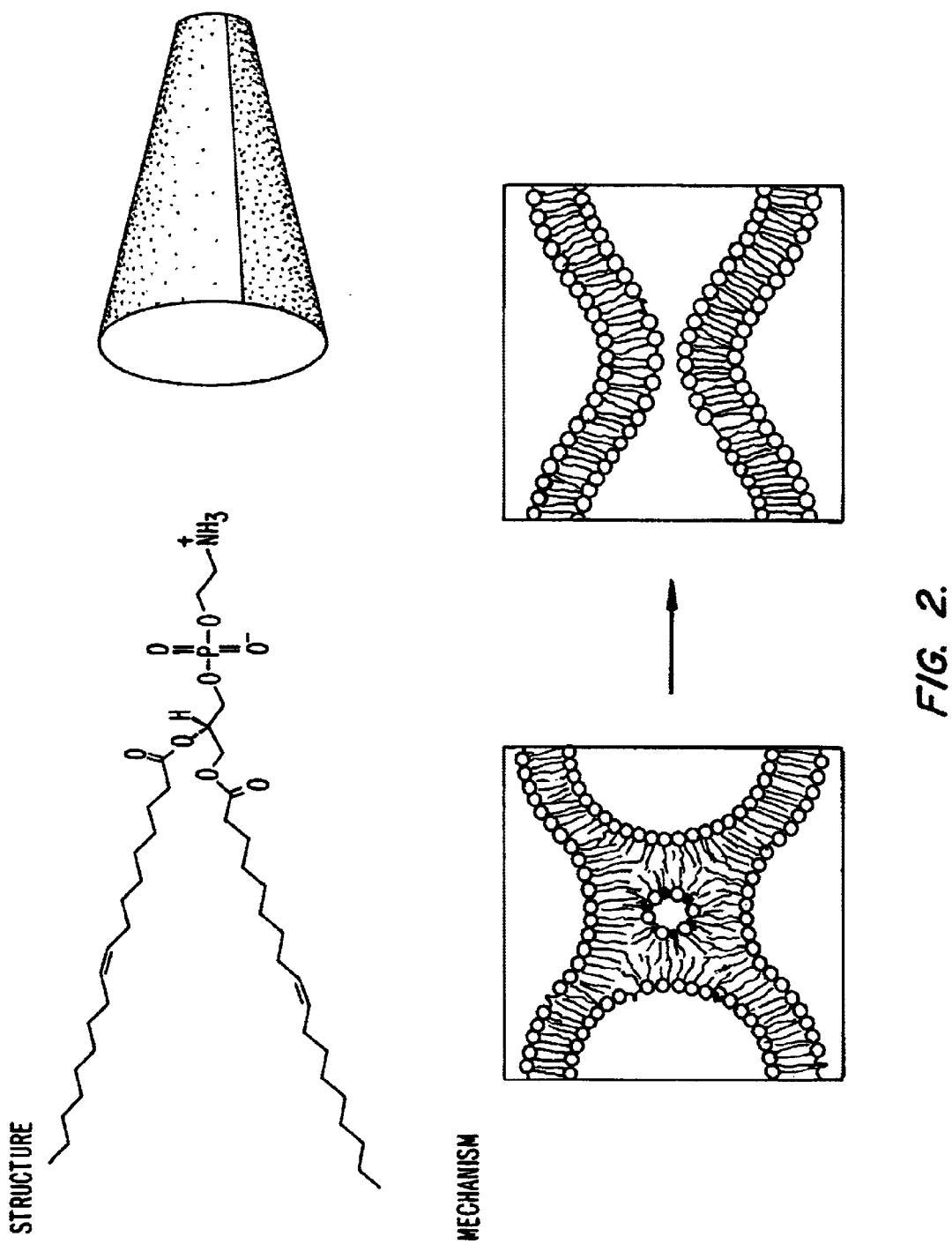
FIG. 2 illustrates the conical form of one fusogenic lipid and further illustrates how fusion with another membrane can occur.

Selection of suitable lipids for use with plasmids will typically involve consideration of the lipid's bilayer-forming capabilities, bilayer-stabilizing capabilities and fusogenic properties. The capabilities, or properties, of a lipid can often be estimated based on the physical shape of the lipid. For example, lipids can be classified according to the three basic structures which lipids can form (see, FIG. 1). Lipids which form micelles typically have large headgroup cross-sectional areas in relation to that of the lipid tail or hydrophobic region. Examples of these lipids are detergents, such as n-octyl β-D-glycopyranoside (OGP), and lysolipids, such as lysophosphatidylcholine (lysoPC). Bilayer-forming lipids or bilayer-stabilizing lipids are typically those which are cylindrical in shape (e.g., DOPC, DOPS, and DODAC). Lipids which form an inverted micelle (the precursor to the hexagonal II phase) have larger tails than heads (e.g., DOPE, see, FIG. 2). Inverted micelles cannot exist in aqueous solution so they must be solubilized in the membrane and form long tube structures called hexagonal II phase ($H_{II}$, phase). The $H_{II}$ phase is thought to be a precursor to fusion of two adjacent membranes. For this reason, DOPE is a powerful membrane fusogen (otherwise referred to as a fusogenic lipid).

Fusogenic lipids such as DOPE, lysolipids and free fatty acids can be accommodated in a bilayer configuration with the appropriate quantities of bilayer-forming lipids. For example, about 20 mol % DOPC will stabilize DOPE in a bilayer. Alternatively, about 30% DODAC (a less effective bilayer-forming lipid) will stabilize DOPE in a bilayer, while only about 10% or perhaps less of PEG-Ceramide is necessary to stabilize DOPE in a bilayer. Similarly, non-micelle forming lipids can be stabilized within micelles with the appropriate quantities of micelle forming lipids such as detergents (e.g., OGP). As the detergent is removed by dialysis, the micelle becomes unstable and becomes a bilayer if enough bilayer-forming lipid is present (FIG. 3). Similarly, a bilayer stabilized by PEG-Ceramide will become unstable once the PEG-Ceramide exchanges out of the outer monolayer.

Considering lipid properties, as noted above, the compositions of the present invention are optimized for the delivery of nucleic acid (e.g., plasmids) to cells. In particular, lipid-plasmid compositions are provided in which the carriers (lipid portions) are composed of at least two types of lipids including (i) fusogenic, nonbilayer forming lipids, and (ii) bilayer-forming or -stabilizing lipids. Preferably, the compositions will further comprise (iii) an aggregation-preventing agent (e.g., PEG-lipids, ATTA-lipids, gangliosides, etc.). In particularly preferred embodiments, the compositions will comprise cationic lipids (as the bilayer-forming or -stabilizing lipids), fusogenic lipids and PEG-lipids.

Cationic lipids which are useful in the present compositions include, for example, DODAC, DOTMA, DDAB, DOTAP, DC-Chol and DMRIE. These lipids and related analogs, which are also useful in the present invention, have been described in co-pending U.S. Ser. No. 08/316,399; U.S. Pat. Nos. 5,208,036, 5,264,618, 5,279,833 and 5,283,185, the disclosures of which are incorporated herein by reference. Particularly preferred within this group is DODAC.

Fusogenic lipids which are useful in the present invention include, for example, DOPE, lysolipids and free fatty acids. Each of these lipids (or lipid groups) can be accommodated in a bilayer configuration with an appropriate quantity of bilayer-forming or bilayer-stabilizing lipids (e.g., DOPC, DODAC, ATTA-lipids, PEG-lipids, such as PEG-Ceramides, etc.). Preferably, the fusogenic lipid is DOPE, or a related phosphatidylethanolamine having two attached fatty acyl chains, preferably unsaturated fatty acyl chains.

Preferably, the lipid-nucleic acid compositions of the present invention contain an aggregation-preventing agent, i.e., a compound (or mixture of compounds) that prevents aggregation during formulation of the lipid-nucleic acid compositions. In addition, such aggregation-preventing agents can also serve as cloaking agents, which help to reduce elimination of the lipid-nucleic acid compositions by the host immune system. These agents can also be targeting agents that help the lipid-nucleic acid formulations to accumulate in the area of the disease or target site. These agents can also be compounds that improve features of the formulation, such as leakiness, longevity in circulation, reduction in toxicity, encapsulation efficiency, etc. Examples of suitable aggregation-preventing agents, include but are not limited to, ATTA-lipid conjugates, such as those disclosed in U.S. patent application Ser. No. 08/996,783, filed Dec. 23, 1997, and U.S. patent application Ser. No. 60/073,852, Feb. 2, 1998; PEG-lipid conjugates, such as those disclosed in U.S. patent application Ser. Nos. 08/486214, 08/316407, and 08/485608; and gangliosides, e.g., $G_{M1}$, such as those disclosed in U.S. Pat. No. 4,837,028, the teachings of all of which are incorporated herein by reference. Examples of these components and others that can usefully be included in the formulations of the invention are known to and used by those skilled in the art.

Figure 4:
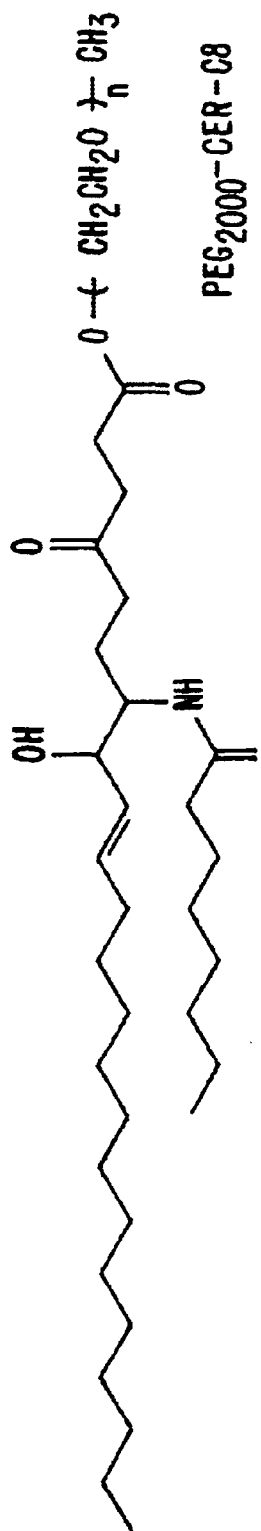
FIG. 4 illustrates the structures of three PEG-Ceramide conjugates and also provides half-times for their dissociation from a lipid vesicle.

In a preferred embodiment, PEG-modified lipids are incorporated into the compositions of the present invention as the aggregation-preventing agent. The use of a PEG-modified lipid positions bulky PEG groups on the surface of the liposome or lipid carrier and prevents binding of DNA to the outside of the carrier (thereby inhibiting cross-linking and aggregation of the lipid carrier). The use of a PEG-ceramide is often preferred and has the additional advantages of stabilizing membrane bilayers and lengthening circulation lifetimes. Additionally, PEG-ceramides can be prepared with different lipid tail lengths to control the lifetime of the PEG-ceramide in the lipid bilayer. In this manner, "programmable" release can be accomplished which results in the control of lipid carrier fusion. For example, PEG-ceramides having $C_{20}$-acyl groups attached to the ceramide moiety will diffuse out of a lipid bilayer carrier with a half-life of 22 hours (see, FIG. 4). PEG-ceramides having $C_{14}$- and $C_8$-acyl groups will diffuse out of the same carrier with half-lives of 10 minutes and less than 1 minute, respectively. As a result, selection of lipid tail length provides a composition in which the bilayer becomes destabilized (and thus fusogenic) at a known rate. Though less preferred, other PEG-lipids or lipid-polyoxyethylene conjugates are useful in the present compositions. Examples of suitable PEG-modified lipids include PEG-modified phosphatidylethanolamine and phosphatidic acid, PEG-modified diacylglycerols and dialkylglycerols, PEG-modified dialkylamines and PEG-modified 1,2-diacyloxypropan-3-amines. Particularly preferred are PEG-ceramide conjugates (e.g., PEG-Cer-$C_8$, PEG-Cer-$C_{14}$ or PEG-Cer-$C_{20}$) which are described in co-pending U.S. Ser. No. 08/486,214, now U.S. Pat. No. 5,820,873, incorporated herein by reference.

In one group of particularly preferred embodiments, the compositions comprise a nucleic acid (e.g., plasmid), DODAC, DOPE and an aggregation-preventing agent (e.g., ATTA-lipids, PEG-lipids, such as PEG-Ceramides), more preferably with the plasmid being encapsulated in an amount of from about 30 µg to about 400 µg per milligram of lipid. Still further preferred are those embodiments in which DODAC is present in an amount of from about 5 mol % to about 50 mol %, DOPE is present in an amount of from about 30 mol % to about 70 mol %, and the aggregation-preventing agent (e.g., PEG-Ceramide) is present in an amount of about 5 mol % to about 20 mol %.

The compositions of the present invention can be prepared by the methods described below to provide compositions which are about 50 nm to about 100 nm in size. One of skill in the art will understand that the size of the compositions can be larger or smaller depending on the size of the plasmid which is encapsulated. Thus, for larger plasmids, the size distribution will typically be from about 80 nm to about 180 nm and, more preferably, from about 50 nm to about 150 nm and, more preferably from about 50 nm to about 90 nm. Additionally, the methods described below result in encapsulation of about 40% to 80% of the plasmids in solution. Surprisingly, compositions having the above properties can be prepared by a detergent dialysis method via manipulation of the salt concentration present in the formulation mixture.

III. Methods of Encapsulating Nucleic Acids in a Lipid Bilayer Carrier

In another aspect, the present invention provides methods for the encapsulation of nucleic acids, preferably plasmids, in a lipid bilayer carrier. The plasmids or nucleic acids present in the compositions formed by these methods exhibit preferably less than about 30% degradation, more preferably, less than about 15% degradation and, even more preferably, less than about 5% degradation when subjected to standard nucleases, such as DNase or normal serum nuclease.

The methods for encapsulating a nucleic acid or plasmid in a lipid bilayer carrier, comprise:
(a) combining the nucleic acid, i.e., antisense, ribozyme or plasmid, with a lipid-detergent mixture, the lipid-detergent mixture comprising a lipid mixture of an aggregation-preventing agent (e.g., a PEG-ceramide) in an amount of about 5 mol % to about 20 mol %, cationic lipids in an amount of about 0.5 mol % to about 50 mol %, and neutral or, alternatively, fusogenic lipids in an amount of from about 30 mol % to about 70 mol % and a detergent, to provide a nucleic acid-lipid-detergent mixture; and (b) dialyzing the nucleic acid-lipid-detergent mixture against a buffered salt solution to remove the detergent and to encapsulate the nucleic acid in a lipid bilayer carrier. In these methods, the salt concentration of the buffered salt solution is adjusted depending on the cationic lipid concentration in the lipid mixture to encapsulate from about 40% to about 80% of the nucleic acid.

In one group of embodiments, the methods further comprise the following step:

(c) removing substantially all of the unencapsulated nucleic acids to provide a purified lipid-bilayer-nucleic acid composition having from about 20 μg to about 400 μg of nucleic acid per about 1 mg of lipid.

The plasmids, antisense, ribozyme or nucleic acids, cationic lipids, fusogenic lipids and aggregation-preventing agent (e.g., ATTA-lipids, PEG-lipids, etc.) that are useful in the present invention are those which have been described above. In preferred embodiments, the amount of cationic lipid is from about 5 mol % to about 50 mol % by weight, more preferably about 10 mol % to about 40 mol % by weight, and most preferably about 20 mol % to about 40 mol % by weight. In a preferred embodiment, the amount of cationic lipids is 10 mol %, 11 mol %, 12 mol %, 13 mol %, 14 mol %, 15 mol %, 16 mol %, 17 mol %, 18 mol %, 19 mol %, 20 mol %, 21 mol %, 22 mol %, 23 mol %, 24 mol %, 25 mol %, 26 mol %, 27 mol %, 28 mol %, 29 mol %, 30 mol %, 31 mol %, 32 mol %, 33 mol %, 34 mol %, 35 mol %, 36 mol %, 37 mol %, 38 mol %, 39 mol %, 40 mol %, 41 mol %, 42 mol %, 43 mol %, 44 mol %, 45 mol %, 46 mol %, 47 mol %, 48 mol %, 49 mol % or 50 mol %.

Similarly, the amount of aggregation-preventing agent (e.g., PEG-Lipid) can vary from about 1 mol % to about 25 mol % and, more preferably, from about 5 mol % to about 20 mol %. For instance, the amount of PEG-ceramide can preferably vary from about 5 mol % to about 20 mol %, depending on the nature of the PEG-ceramide (e.g., PEG-Cer-$C_8$, PEG-Cer-$C_{14}$ or PEG-Cer-$C_{20}$), or the combination of PEG-ceramides used. Selection of the amounts of each can provide compositions in which the fusogenic properties are programmable (i.e., become fusogenic within a predetermined timeframe, depending on the rate at which the PEG-ceramide diffuses out of the composition).

A nucleic acid-lipid-detergent mixture is formed by combining the nucleic acid or plasmid with a lipid-detergent mixture. The lipid-detergent mixture is a combination of aggregation-preventing agent (e.g., ATTA-modified lipids, PEG-modified lipids, such as PEG-ceramides), cationic lipids, neutral or fusogenic lipids and a detergent. The detergent is preferably an aqueous solution of a neutral detergent having a critical micelle concentration of 15–300 mM and, more preferably, 20–50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent® 3–08; Zwittergent® 3–10; Triton X-405; hexyl-, heptyl-, octyl- and nonyl-β-D-glucopyranoside; and heptylthioglucopyranoside; with octyl β-D-glucopyranoside being the most preferred. The concentration of detergent in the detergent solution is typically about 100 mM to about 2 M, preferably about 200 mM to about 1.5 M.

The lipid-detergent mixture and nucleic acids typically be combined to produce a charge ratio (+/–) of about 1:1 to about 20:1, preferably in a ratio of about 3:1 to about 15:1. Additionally, the overall concentration of nucleic acid in solution will typically be from about 25 μg/mL to about 1 mg/mL, preferably from about 25–500 μg/mL and, more preferably, from about 100–300 μ/mL. The combination of nucleic acids and lipids in detergent solution is kept, typically at room temperature, for a period of time which is sufficient for complete mixing to occur. While not intending to be bound by any particular theory, it is believed that coated complexes form in which the negative charges of the nucleic acid are paired with positively charged lipids. Excess lipids complete the formation of a bilayer surrounding and encapsulating the nucleic acids. In other embodiments, the nucleic acids and lipid-detergent mixture can be combined and warmed to temperatures of up to about 37° C. For those embodiments in which temperature-sensitive plasmids are used, the mixtures or coated complexes can be formed at lower temperatures, typically down to about 4° C.

The resulting nucleic acid-lipid-detergent mixture is then subjected to dialysis against a buffered salt solution to remove the detergent from the mixture. The removal of the detergent results in the completed formation of a lipid-bilayer which surrounds the nucleic acids or plasmid providing serum-stable nucleic acid-lipid particles which have a size of from about 50 nm to about 150 nm. The particles thus formed do not aggregate.

The buffered salt solution which is used in the dialysis step will typically be a solution of alkali or alkaline earth halides (e.g., NaCl, KCl, and the like), phosphates (e.g., sodium or potassium phosphate), citrates (e.g., sodium citrate) or combinations thereof. The buffer which is used will typically be HEPES or an equivalent buffer. In particularly preferred embodiments, the buffered salt solution is a HEPES-buffered NaCl solution.

Changes in the salt concentration of the dialysis buffer requires significant changes in the lipid composition for efficient encapsulation in the above process. More particularly, the encapsulation efficiency, particle size and the amount of cationic lipid which is used to achieve optimum loading is altered upon changing the salt concentration in the dialysis buffer.

For example, a dialysis buffer containing 150 mM NaCl provides optimal loading of a plasmid in compositions of about 6 mol % DODAC (by weight). By adding citrate to the dialysis buffer, the amounts of DODAC which are used to achieve optimal encapsulation of a plasmid are increased, while maintaining a narrow distribution of particle sizes.

Still higher levels of DODAC (or other suitable cationic lipids) can be used and provide high levels of plasmid encapsulation (typically greater than 30% encapsulation with plasmid/lipid ratios of >20 μg plasmid/mg lipid). For example, a dialysis buffer of 150 mM NaCl and 150 mM sodium phosphate is useful for compositions of about 40–45 mol % DODAC.

Once the plasmid-lipid compositions have formed (typically as particles), any unencapsulated plasmid or empty liposomes can be removed by ion-exchange chromatography or gel filtration, respectively, and any empty liposomes can be removed by density gradient centrifugation using techniques which are well known in the art.

IV. Pharmaceutical Preparations

The nucleic acid (e.g., plasmid)-lipid compositions of the present invention can be administered either alone or in mixture with a physiologically-acceptable carrier (such as physiological saline or phosphate buffer) selected in accordance with the route of administration and standard pharmaceutical practice.

Pharmaceutical compositions comprising the nucleic acid (e.g., plasmid)-lipid compositions (e.g., in particle or liposome form) of the invention are prepared according to standard techniques and further comprise a pharmaceutically acceptable carrier. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The concentration of particles in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration. For diagnosis, the amount of particles administered will depend upon the particular label used, the disease state being diagnosed and the judgement of the clinician but will generally be between about 0.01 and about 50 mg per kilogram of body weight, preferably between about 0.1 and about 5 mg/kg of body weight.

As noted above, it is often desirable to include polyethylene glycol (PEG), PEG-lipids (e.g., PEG-ceramides), ATTA-lipids, or ganglioside $G_{M1}$-modified lipids to the particles. Addition of such components prevents particle aggregation and provides a means for increasing circulation lifetime and increasing the delivery of the plasmid-lipid particles to the target tissues. Typically, the concentration of the PEG, PEG-lipids (e.g., PEG-ceramide), ATTA-lipids or $G_{M1}$-modified lipids in the particle will be about 1–25 mol %, preferably about 5–20 mol %.

Overall particle charge is also an important determinant in particle clearance from the blood, with negatively charged complexes being taken up more rapidly by the reticuloendothelial system (Juliano, *Biochem. Biophys. Res. Commun.* 63:651 (1975)) and thus having shorter half-lives in the bloodstream. Particles with prolonged circulation half-lives are typically desirable for therapeutic and diagnostic uses. For instance, particles which can be maintained from 8, 12, or up to 24 hours in the bloodstream are particularly preferred.

In another example of their use, the nucleic acid-lipid particles can be incorporated into a broad range of topical dosage forms including but not limited to gels, oils, emulsions and the like. For instance, a suspension containing the plasmid-lipid particles can be formulated and administered as topical creams, pastes, ointments, gels, lotions and the like.

The present invention also provides nucleic acid-lipid particles in kit form. The kit will typically be comprised of a container which is compartmentalized for holding the various elements of the kit. The kit will contain the compositions of the present inventions, preferably in dehydrated form, with instructions for their rehydration and administration. In still other embodiments, the particles and/or compositions comprising the particles will have a targeting moiety attached to the surface of the particle. Methods of attaching targeting moieties (e.g., antibodies, proteins) to lipids (such as those used in the present particles) are known to those of skill in the art.

Dosage for the nucleic acid-lipid particle formulations will depend on the ratio of nucleic acid to lipid and the administrating physician's opinion based on age, weight, and condition of the patient.

V. Administration of Nucleic Acid-Lipid Particle Formulations

The serum-stable nucleic acid-lipid compositions particles of the present invention are useful for the introduction of plasmids into cells. Accordingly, the present invention also provides methods for introducing a plasmid into a cell. The methods are carried out in vitro or in vivo by first forming the particles or compositions as described above, then contacting the particles with the cells for a period of time sufficient for transfection to occur.

The particles of the present invention can be adsorbed to almost any cell type. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid. Contact between the cells and the plasmid-lipid particles, when carried out in vitro, will take place in a biologically compatible medium. The concentration of particles can vary widely depending on the particular application, but is generally between about 1 $\mu$mol and about 10 mmol. Treatment of the cells with the plasmid-lipid particles will generally be carried out at physiological temperatures (about 37° C.) for periods of time of from about 1 to 6 hours, preferably of from about 2 to 4 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

In one group of preferred embodiments, a nucleic acid-lipid particle suspension is added to 60–80% confluent plated cells having a cell density of from about $10^3$ to about $10^5$ cells/mL, more preferably about $2\times10^4$ cells/mL. The concentration of the suspension added to the cells is preferably of from about 0.01 to 0.2 $\mu$g/mL, more preferably about 0.1 $\mu$g/mL.

Typical applications include using well known transfection procedures to provide intracellular delivery of DNA or MRNA sequences which code for therapeutically useful polypeptides. However, the compositions can also be used for the delivery of the expressed gene product or protein itself. In this manner, therapy is provided for genetic diseases by supplying deficient or absent gene products (i.e., for Duchenne's dystrophy, see, Kunkel, et al., *Brit. Med. Bull.* 45(3):630–643 (1989), and for cystic fibrosis, see, Goodfellow, *Nature*, 341:102–103 (1989)). Other uses for the compositions of the present invention include introduction of antisense oligonucleotides in cells (see, Bennett, et al., *Mol. Pharm.*, 41:1023–1033 (1992)).

Alternatively, the compositions of the present invention can also be used for the transfection of cells in vivo, using methods which are known to those of skill in the art. In particular, Zhu, et al., *Science*, 261:209–211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature*, 362:250–256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.*, 298:278–281 (1989), incorporated herein by reference, describes the in vivo transfection of lungs of mice with a functioning prokaryotic gene encoding the intracellular enzyme, chloramphenicol acetyltransferase (CAT).

For in vivo administration, the pharmaceutical compositions are preferably administered parenterally, i.e., intraarticularly, intravenously, intraperitoneally, subcutaneously, or intramuscularly. More preferably, the pharmaceutical compositions are administered intravenously or intraperitoneally by a bolus injection. For example, see, Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York, 101:512–527 (1983); Mannino, et al., *Biotechniques*, 6:682–690 (1988); Nicolau, et al., *Crit. Rev. Ther. Drug Carrier Syst.*, 6:239–271 (1989), and Behr, *Acc. Chem. Res.*, 26:274–278 (1993). Still other methods of administering lipid-based therapeutics are described in, for example, Rahman, et al., U.S. Pat. No. 3,993,754; Sears, U.S. Pat. No. 4,145,410; Papahadjopoulos, et al., U.S. Pat. No. 4,235,871; Schneider, U.S. Pat. No. 4,224,179; Lenk, et al., U.S. Pat. No. 4,522,803; and Fountain, et al., U.S. Pat. No. 4,588,578.

In other methods, the pharmaceutical preparations may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The nucleic acid-lipid particles can also be administered in an aerosol inhaled into the lungs (see, Brigham, et al., *Am. J. Sci.*, 298(4):278–281 (1989)) or by direct injection at the site of disease (Culver, HUMAN GENE THERAPY, Mary-Ann Liebert, Inc., Publishers, New York. pp.70–71 (1994)).

In accordance with the above administration methods, the compositions of the present invention can be used to inhibit tumor cell growth, the method comprising contacting the tumor cell with an effective amount of a lipid-nucleic acid composition of the present invention. Tumor cells include, but are not limited to, lung, colon, breast, ovarian, prostate and hepatic tumor cells as well as squamous cell carcinomas. In a presently preferred embodiment, the tumor cells are present in a mammalian subject. Mammalian subjects include, but are not limited to, humans, laboratory animals, domestic pets and farm animals. Preferred hosts include humans, nonhuman primates, dogs, cats, cattle, horses and sheep. In a further preferred embodiment, the above method further comprises the step of observing for a reduction in the growth of the tumor cells.

In another embodiment, the present invention provides a method of treating cancer, the method comprising administering to a mammalian subject having cancer a therapeutically effective amount of a lipid-nucleic acid composition of the present invention. The compositions of the present invention are useful for treating a wide variety of cancers. Such cancers include, by way of example and not limitation, carcinomas such as pharynx, colon, rectal, pancreatic, stomach, liver, lung, breast, skin, prostate, ovary, cervical, uterine and bladder cancers; leukemias; lymphomas; gliomas; retinoblastomas; and sarcomas. Moreover, in accordance with the above method, mammalian subjects include, but are not limited to, humans, laboratory animals, domestic pets and farm animals.

Lipid-nucleic acid compositions suitable for use in the methods of the present invention can readily be identified using in vitro and in vivo screening assays. Such assays may screen for the ability of a particular composition to inhibit tumor cell growth or to abolish tumorigenicity of malignant cells in vitro or in vivo. For instance, tumor cell lines can be exposed to varying concentrations of a composition of interest, and the viability of the cells can be measured at set time points using the alamar Blue® assay (commercially available from BioSource, International of Camarillo, Calif.). When alamar Blue dye is added to the culture medium, the dye is reduced by cellular mitochondrial enzymes yielding a soluble product with substantially enhanced fluorescence. This fluorescence can be measured with a fluorimeter, whereby the signal is directly proportional to the cell number. Using this information, $IC_{50}$ (concentration of composition lethal to 50% of a cell culture as compared to a control culture) values for the compositions of interest can be readily be calculated.

As will be appreciated by the skilled artisan, many varieties of tumor cell cultures and cell lines can be used to screen for activity including, but not limited to, MDA MB 231 (breast), MCF-7 (breast), MDA MB 468 (breast), Siha (squamous cell carcinoma), A549 (nonsmall cell lung), HL-60 (leukemia) Ovcar-3 (ovarian), etc. Of course, other in vitro and/or in vivo assays to screen for anti-tumor and/or anti-cancer activity known to and used by the skilled artisan can also be employed to identify effective compositions useful in the methods of the present invention.

VII. EXAMPLE 1

Formulation of Lipid-Nucleic Acid Compositions

A. Materials and Methods

1. Materials

N,N-dioleyl-N,N-dimethyl ammonium chloride (DODAC), monomethoxy polyethylene2000 glycol succinate-(C8:0-ceramide) (PEG-Ceramide-$C_8$), pACN53, pINEXP005, pINEXL002 and pINEX018 plasmids and pL002 (luciferase) plasmid were manufactured and supplied by INEX Pharmaceuticals Corp. Dioleyl-phosphatidylethanolamine (DOPE) was obtained from Northern Lipids (Vancouver, British Columbia, Canada). Picogreen dsDNA quantitation reagent was obtained from Molecular Probes (Eugene, Oreg.). Dialysis buffers were prepared from commercially available reagents (HEPES, NaCl, dibasic sodium phosphate, monobasic sodium phosphate, trisodium citrate) by standard methods. Octyl-β-D-glucoside (OGP), Spectrapor dialysis tubing and ACS or higher grade reagents were obtained from VWR Scientific, Fisher Scientific or Sigma Chemical Company.

2. Method of Formulation

A variety of formulations were prepared using the procedures outlined below. In a first method, a formulation of plasmid with DOPE:DODAC:PEG-Ceramide-$C_8$ (42.5:42.5:15 mol %) was prepared. In other methods, the PEG-Ceramide was held constant and formulations were prepared by altering the amounts of DODAC present.

a. DOPE:DODAC:PEG-Ceramide-$C_8$ (42.5:42.5:15 mol %)

In a preparation containing 5 mg/ml total lipid, the concentration of each lipid at the above mol % quantities are DOPE (1.69 mg/ml), DODAC (1.315 mg/ml) and PEG-Ceramide-C8 (2.005 mg/ml) based on molecular weights calculated at 744, 582 and 2515, respectively. Each of these can be dissolved stock solutions using absolute ethanol, 2:1 chloroform:methanol or 9:1 benzene:methanol. If stock solutions of >20 mg/ml are required, the latter two solvent mixtures are not suitable. Lipids prepared in benzene:methanol have the added advantage that they can be lyophilized (freeze-dried) to a fluffy powder. A dried film of the above lipids are prepared in glass test-tubes (or in round bottomed flasks when prepared in large scale). The combined lipids are dried under a stream of nitrogen (small scale) or in a rotary evaporator (large scale) followed by incubation in vacuo (<100 microns Hg) for at least 2 hours at room temperature. Alternatively, benzene:methanol solutions may be freeze-dried directly. A 1 M solution of OGP (100 μl) is added to each tube containing dried lipid. The plasmid suspension (typically 200–300 μl at 1 mg/mL in TRIS-EDTA buffer) is added to the lipid film. The suspension is made up to 1.0 ml with dialysis buffer, and the suspension is mixed by vortexing until the lipid film is dissolved and a clear solution is formed. Alternatively, the plasmid may be added after the lipid film is dissolved, if desired. The tube is allowed to stand for approximately 30 minutes at room temperature and then the contents are loaded into prepared dialysis bags. Dialysis conditions are found to vary slightly with the quality and type of the plasmid. However, at this DODAC concentration optimum formulations are obtained with 150 mM $NaPO_4$, pH 7.4 with 150 to 175 mM NaCl. The formulations are dialyzed against 2 changes of 2 L of the appropriate buffer (per 1 to 10 ml of formulation).

b. Varying DODAC and DOPE amounts

Lipid mixtures of DODAC/DOPE/PEG-Cer-C8 containing 15 mol % of PEG-Cer-C8 were used for all samples. The amount of DODAC and DOPE were varied to reach desired mole % concentrations. For formulations containing greater than 30 mol % DODAC, the total lipid concentration is typically 5 mg/mL. Formulations containing 30 mol % DODAC and less are prepared at 10 mg/mL total lipid. Five or ten mg of lipid mixture of DODAC/DOPE/PEG-Cer-C8 was dissolved in ethanol or organic solvent (MeOH/$CHCl_3$: 1/1). The solvent was removed by gas $N_2$ and then dried under vacuum for at least 3 hrs. The lipid mixture is dried to a film in a glass tube or flask as described above. The detergent suspension is prepared as described above. Where DODAC concentrations are below 42.5 mol % (and DOPE increased correspondingly), the buffer and buffer salt concentrations must be adjusted accordingly to allow optimum encapsulation and the selection of specific buffer concentrations is described in the examples below (see, Table 1).

3. Method of Removing Unencapsulated Plasmid

In order to remove unencapsulated plasmid DNA and to determine the absolute recovery of encapsulated plasmid the formulations are *cleaned* by running through a short column (typically 3 cm×1 cm or larger) of DEAE Sepharose which had been pre-equilibrated in either HBS or the respective dialysis buffer for the formulation (i.e., with 150 mM sodium phosphate (NaPO4), 150 mM NaCl, pH 7.4). After running through the column the preparations are normally dialyzed against HBS and concentrated in the dialysis bag using Aquacide II (Calbiochem) to a desired plasmid concentration.

4. Method of Determining Percent Encapsulation

For the determination of percent encapsulation a −/+ Triton X-100 method was used. Typically, aliquots of the formulation taken directly from dialysis were diluted 1:400 in HBS and 2 μL of Picogreen reagent were added to 1 mL of the diluted samples. The fluorescence was measured at 495 nm (excitation) and 525 nm (emission), both in the absence and presence of 10 μL, 10% Triton-X100. The percent encapsulation was calculated as:

$$1 - \text{Fluorescence} - \text{Triton}/\text{Fluorescence} + \text{Triton} \times 100.$$

For the determination of absolute plasmid DNA concentration, aliquots of formulation were measured for fluorescence as above in the presence of Triton X100 and compared to standard plasmid concentrations identically prepared.

The following examples are offered solely for the purposes of illustration, and are intended neither to limit nor to define the invention. In each of these examples, the term "DNA" or "plasmid" refers to the plasmid pCMV4-CAT.

5. Method for Separation of Empty Liposomes from Plasmid Containing Vesicles a. Sucrose Density Gradient Isolation.

Sucrose density gradients are used for the removal of lipid which is not associated with plasmid. The particular gradient used varies with the DODAC concentration as formulations containing the highest DODAC concentrations are the least dense. Gradients are formed by layering decreasing concentrations of HBS-sucrose (W/V) solutions in Beckman (13.2 mL) ultraclear ultracentrifuge tubes above one another. This process is simplified if the solutions are prechilled (at 4° C.) to increase the viscosity of the solutions and using a short Pasteur pipette where the tip has been bent upward (done under a gentle flame). Two useful gradients have been employed. For INEX 351 formulations (42.5 mol % DODAC), a gradient of 5% (3 ml):2.5% (5 ml):1% (2 ml) sucrose (w/v in 20 mM HBS) has been employed. The formulation has been found to settle on the 2.5%–5% sucrose interface. For formulations containing 20–30 mol % DODAC, a gradient containing 10% (2 ml): 5% (2 ml):2.5% (4 ml):1% (2 ml) sucrose has been employed. The plasmic containing TCS has been found to settle on the 5%–10% interface. With either gradient, the formulations are centrifuged at 36,000 rpm in a Beckman SW41 Ti rotor at 25° C. for 7–14 hours. A half deceleration speed has not been found to disturb the bands which form. In every case, 3–4 diffuse bands are observed in the upper portion of the gradient, while a narrower band is generally observed at the lower interface of each gradient. The lower band normally contains 90% of the applied DNA and is removed by piercing the centrifuge tube with a needle and removing the band using a syringe (3 ml normally adequate). Excellent separation of the desired band has been accomplished with starting plasmid DNA containing up to 400 μg of plasmid per tube. After removal from the gradient, the formulation is dialyzed against 2×21 HBS at 4° C., and the resulting preparation is analyzed for DNA content and particle size.

B. Experiments

1. Formulation: Detergent Dialysis

Figure 5:
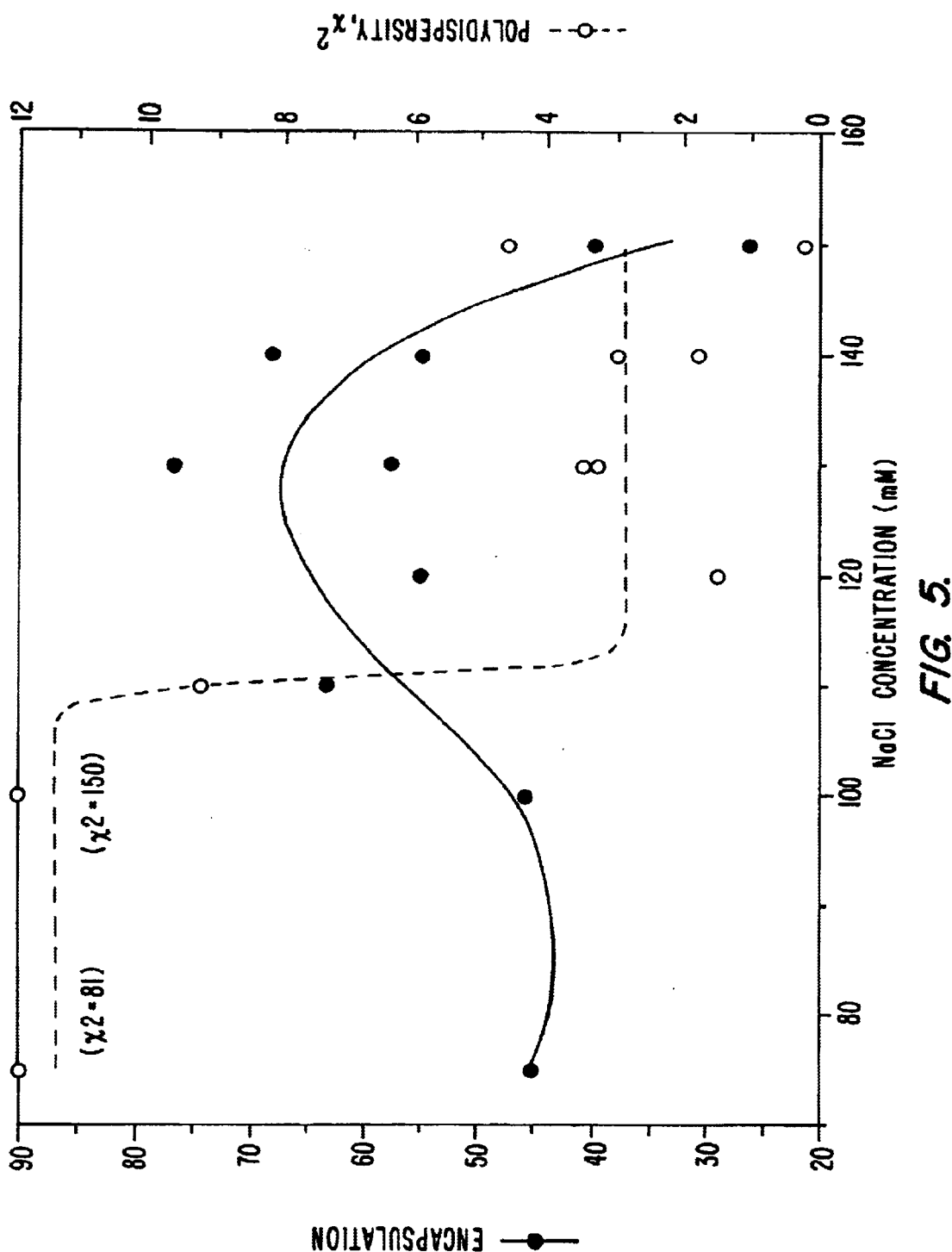
FIG. 5. Encapsulation of pINEXL018 plasmid using DODAC/DOPE/PEG-Cer-C8 (30:55:15 mol %) by detergent dialysis in citrate buffer. Effect of varying NaCl concentration with constant citrate concentration (100 mM Na citrate, 5 mM HEPES, pH:7.2) is illustrated. The encapsulation efficiency and polydispersity, $\chi^2$ (a measure of formulation homogeneity), of formulations are plotted as functions of NaCl. Successful formulations are indicated by the high encapsulation and low $\chi^2$.
Figure 6:
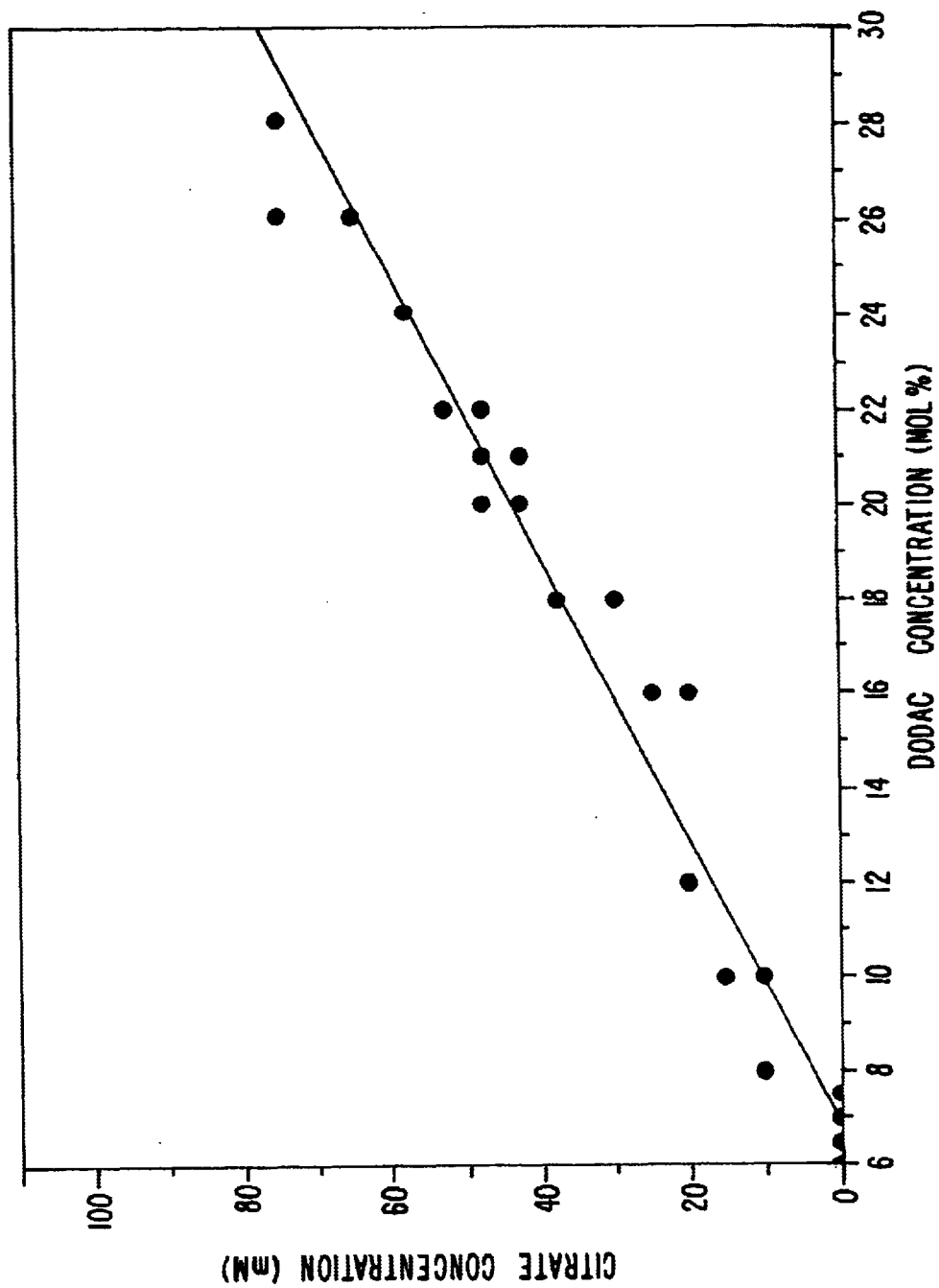
FIG. 6. Encapsulation of pINEX L018 plasmid using DODAC/DOPE/PEG-Cer-C8 system by detergent dialysis in citrate buffer containing constant NaCl concentration (150 mM) and 5 mM HEPES, pH:7.2. The relationship between varying DODAC mol % and the optimal citrate concentration and the effect upon encapsulation efficiency is demonstrated. Each point represents a formulation of acceptable size and encapsulation efficiency. The optimal range of citrate and DODAC concentrations are indicated by the solid line. Typically, those preparations prepared below the optimal citrate concentration have large sizes or aggregate, and those formulations prepared above the optimal citrate concentration have low encapsulation efficiencies (0–30%).

The ionic strength and the counter-ion concentration of the dialysis buffer required for efficient encapsulation of plasmid DNA are critical and there is a direct relationship between the ionic strength and the cationic lipid concentration used in the formulation. Both the ionic strength and the counter-ion concentration can be adjusted by varying the salt concentration and/or the type of salt ions in the buffer. The ionic strength/counter-ion concentration necessary for efficient encapsulation increases with increasing cationic lipid concentration in the formulation. Phosphate and citrate, respectively, are used as counter-ions to compete with the charges on the polynucleotide for interaction with the cationic charge on the lipid headgroup. When the ionic strength (salt concentration) is too high, it results in vesicle formation with little or no encapsulation, and when it is below the optimum concentration, there is formation of lipid/DNA complexes and of aggregates. An indication for aggregation is a wide size distribution (high polydispersity) of the particles/vesicles formed (see, FIG. 5). Therefore, the optimum salt concentration needs to be determined for each desired cationic lipid concentration in the formulation. The optimum salt concentration required in the buffer for efficient encapsulation with different concentrations of cationic lipid is summarized in Table 1. Examples for two salt combinations, NaCl with citrate and NaCl with phosphate, are illustrated (FIGS. 5 through 9). FIG. 5 shows the effect of the NaCl concentration in the citrate/NaCl buffer on the encapsulation efficiency at a given cationic lipid concentration. FIG. 6 shows the relationship between the cationic lipid concentration (DODAC) and the citrate concentration in the buffer to obtain efficient encapsulation. NaCl/citrate was suitable for formulations with DODAC concentration of up to 30 mol %, while NaCl/phosphate could be used over the entire DODAC concentration range tested.

TABLE 1

Characterization of representative large scale TCS formulations.

| DODAC concentration | Buffer | Encapsulation efficiency | Nicomp particle size (nm)[a] |
|---|---|---|---|
| 7% | 0.0 mM citrate, 150 mM NaCl, | 80.5% | 37 ± 18 |
| 17.1% | 40.0 mM citrate, 150 mM NaCl, | 38.5% | 39 ± 20 |
| 22.2% | 70.0 mM citrate, 150 mM NaCl, | 53.5% | 43 ± 22 |
| 32.0% | 105 mM citrate, 150 mM NaCl, Phosphate | 51.0% | 53 ± 35 |
| 20% | 105 mM NaPO$_4$ | 63.% | 178 |
| 24% | 130 mM NaPO$_4$ | 50.7% | 250 |
| 30% | 150 mM NaPO$_4$ | 56.8% | 109 |
| 42.5% | 150 mM NaPO$_4$, 130 mM NaCl | 49% | 131 |

Figure 7:
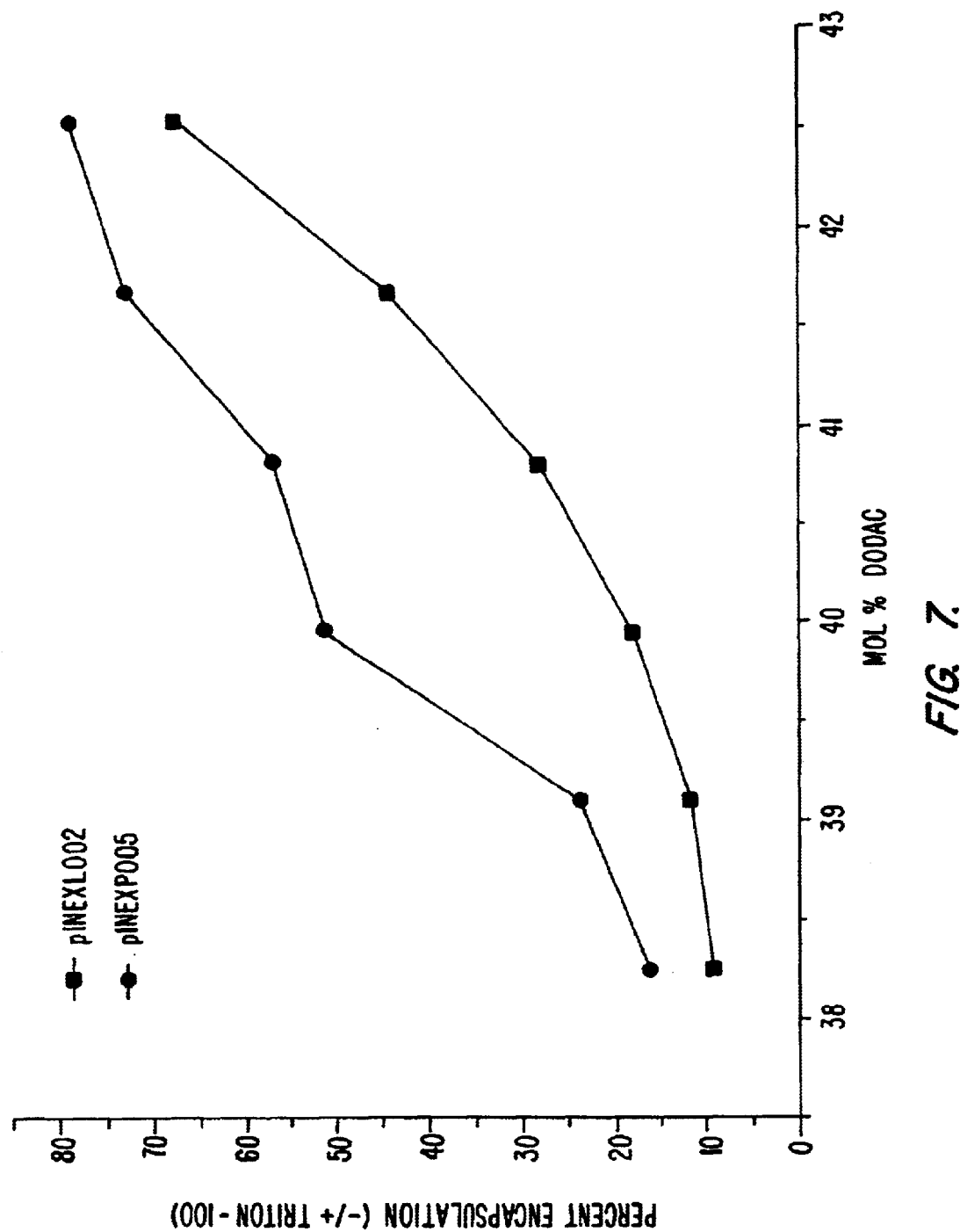
FIG. 7. Effect of DODAC concentration on plasmid encapsulation. In this study, the effect of small (1 mol %) changes of DODAC concentration were tested at constant lipid (10 mg/mL), plasmid (400 μg/mL) and buffer concentrations. Encapsulation efficiency dropped significantly with a decrease in DODAC concentration, indicating that care must be taken to precisely deliver DODAC at a given NaCl concentration. pINEXL002 was formulated in 150 mM $NaPO_4$, 175 mM NaCl, pH 7.4, and pINEXP005 was formulated in 150 mM $NaPO_4$, 150 mM NaCl pH 7.4.
Figure 8:
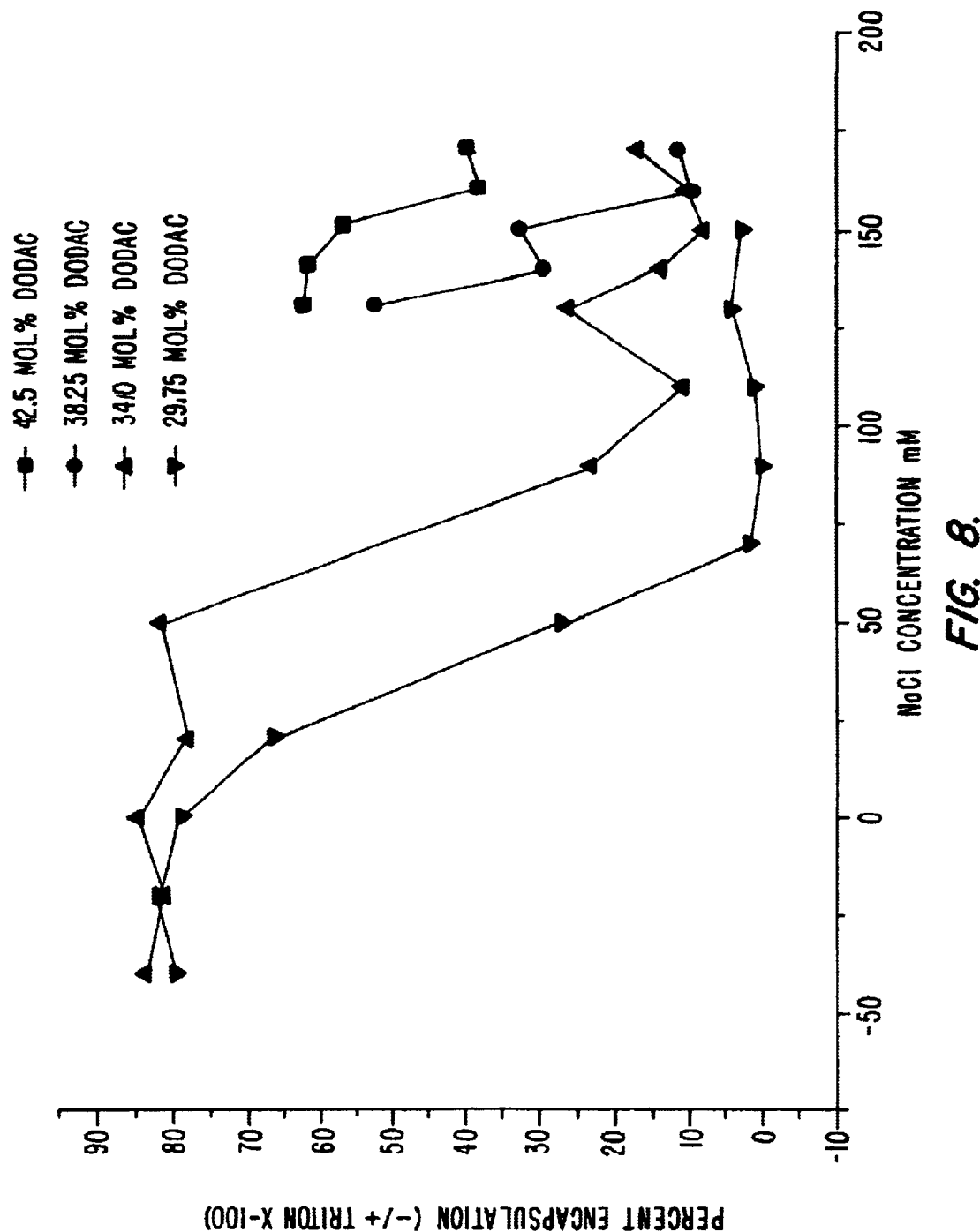
FIG. 8. Encapsulation of pINEXP005. Effect of varying NaCl with constant $NaPO_4$ concentration. The relationship between varying the salt concentration on the encapsulation of plasmid over a range of INEX TCS DODAC concentrations is illustrated. Negative NaCl concentrations indicate where the buffer concentration was decreased to an extent where no NaCl was included in the dialysis buffer, and the phosphate buffer concentration alone was decreased to achieve encapsulation. Formulations were prepared containing 10 mg/mL total lipid, 400 μg/mL plasmid DNA. In each 1.0 ml formulation, the PEG-C8 concentration was maintained at 15 mol %, the DODAC concentration was varied as indicated and the balance of the lipid was DOPE. At each DODAC concentration, formulations were dialyzed against a range of buffer salt concentrations. This study demonstrates that a range of encapsulation efficiencies can be achieved by adjusting the NaCl concentration in a phosphate buffer. Thus, the association of the DNA with the lipid particles can be regulated.
Figure 9:
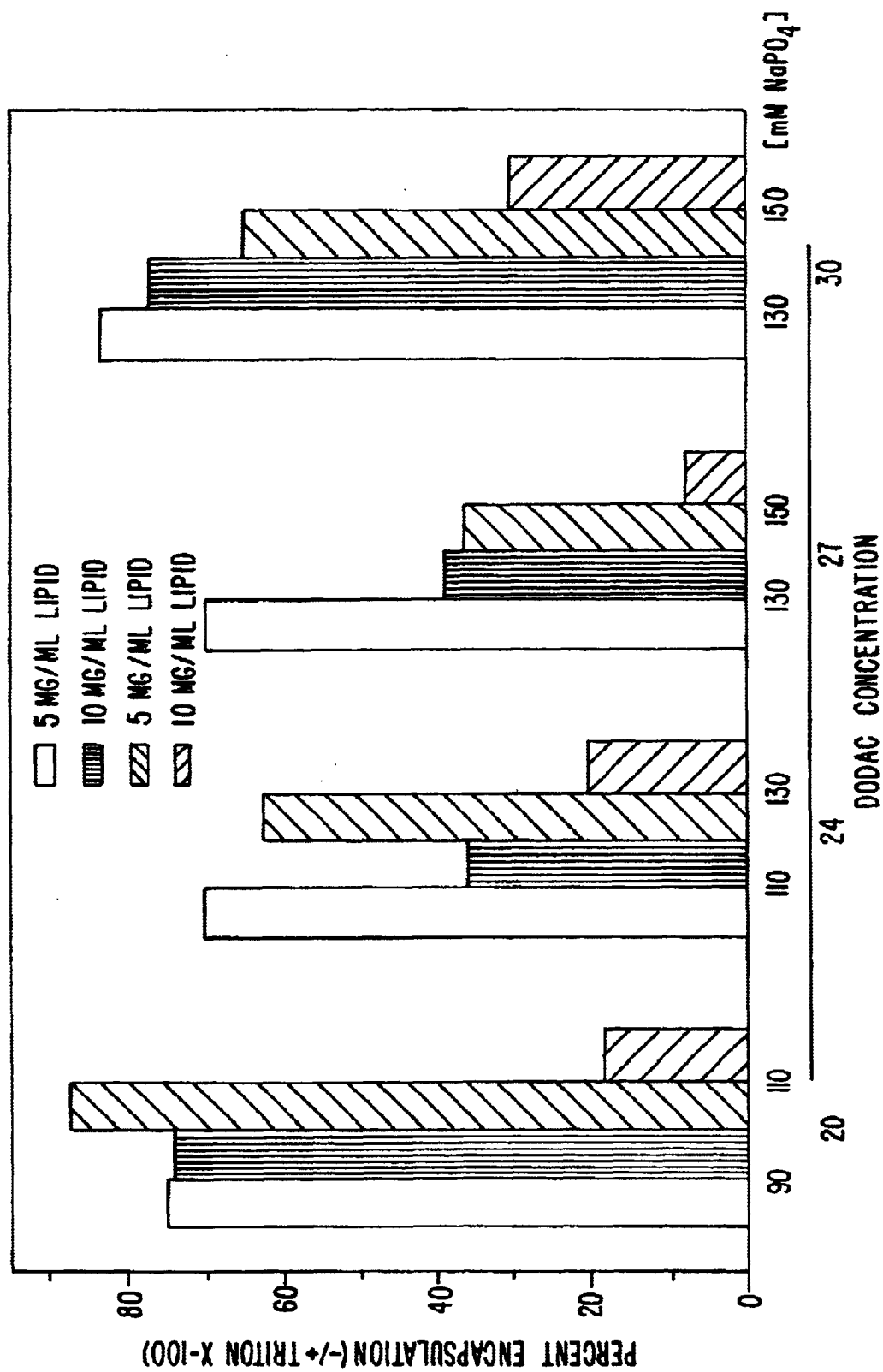
FIG. 9. Encapsulation of pINEXL018. Effect of varying $NaPO_4$ and total lipid concentration. The effect of varying the lipid and phosphate buffer concentration on the encapsulation of plasmid over a range of INEX TCS DODAC concentrations is demonstrated. Formulations were prepared containing either 5 or 10 mg/mL total lipid, 400 μg/mL plasmid DNA. As in FIG. 3, the formulations were prepared containing 15 mol % PEG-C8, the range of indicated DODAC concentrations and the balance of lipid made up with DODAC. In this study, the concentration of the dialysis phosphate buffer alone could be decreased to achieve encapsulation of a plasmid over this range of DODAC concentrations.
Figure 10:
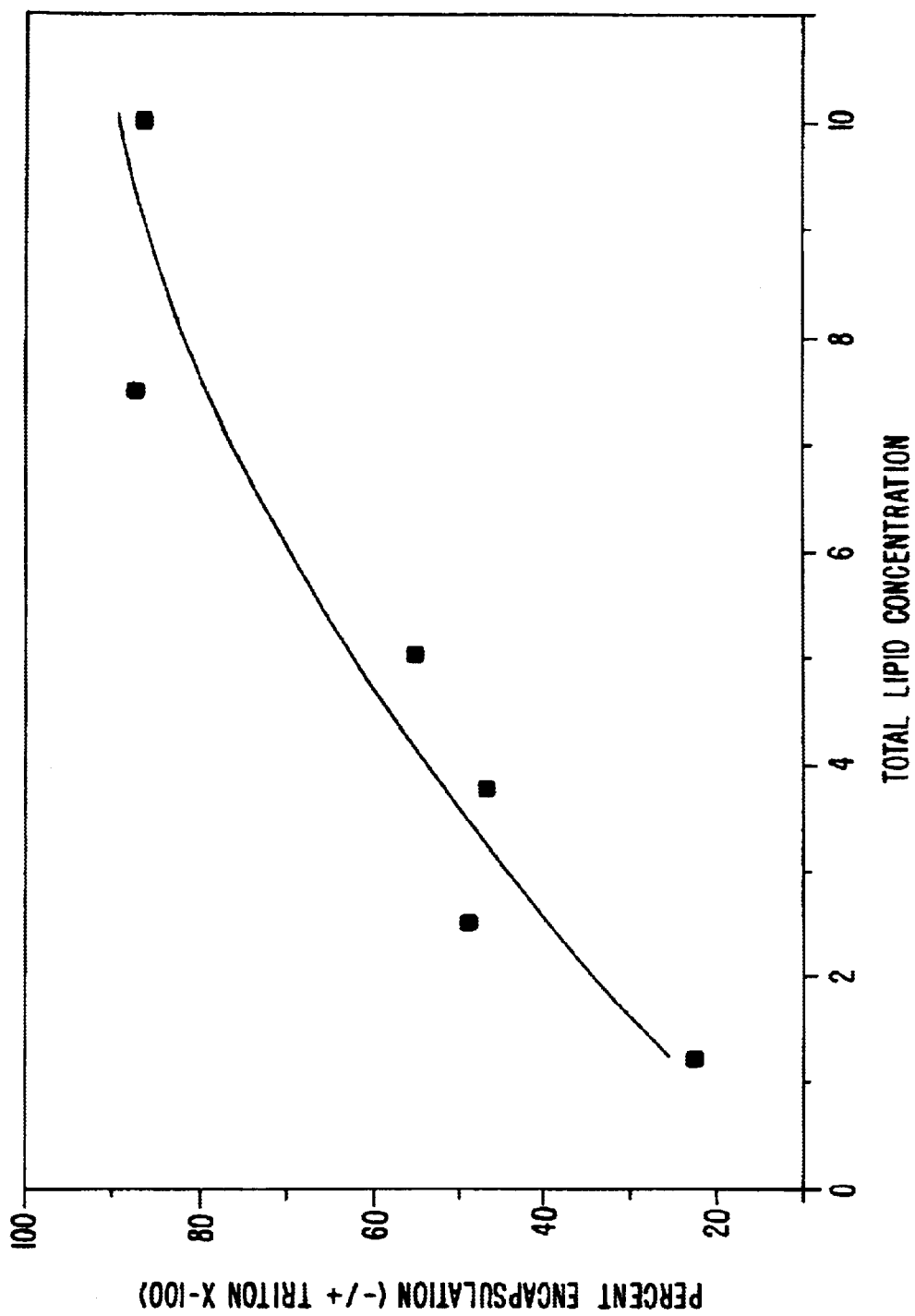
FIG. 10. Effect of lipid concentration on the encapsulation of pINEXP005 in INEX 351. Formulations were prepared in 1 mL formulations containing 200 μg/mL plasmid and total lipids ranging from 1.25 mg/mL to 10 mg/mL. INEX 351 indicates a formulation containing 42.5 mol % DODAC, 42.5 mol % DOPE and 15 mol % PEG-C8. The formulations were dialyzed against 150 mM $NaPO_4$, 150 mM NaCl, pH 7.4. This study demonstrates that an increase in lipid concentration increases the extent of plasmid concentration. Thus, sufficient total lipid is required for loading of the plasmid into the particles.
Figure 11:
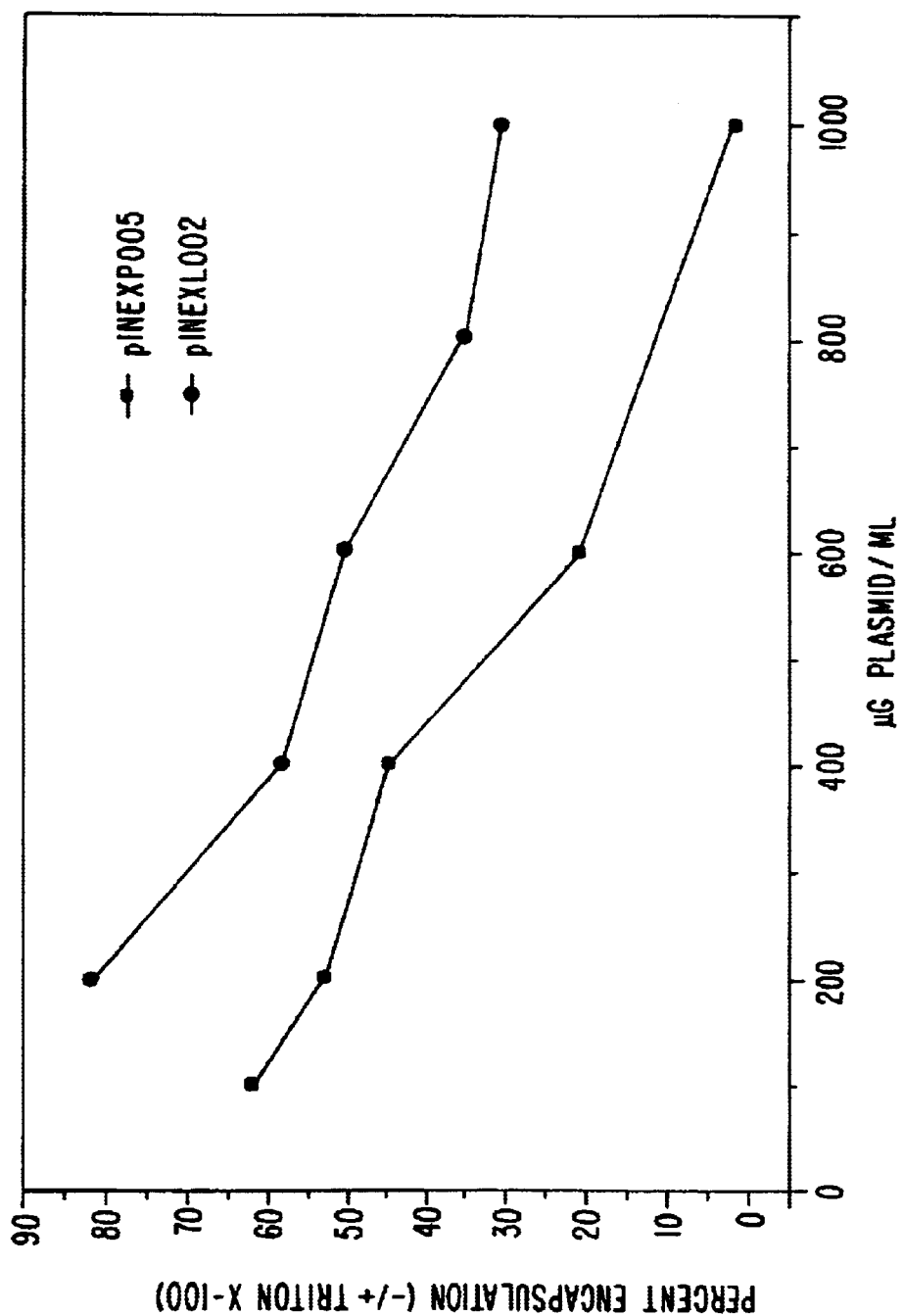
FIG. 11. Effect of plasmid concentration on encapsulation efficiency in INEX 351 particles were prepared in 1 mL formulations containing 5 mg/mL total lipid and the concentration of the plasmids ranged from 100 to 1000 μg/mL. Formulations containing pINEXP005 and pINEXL002 were dialyzed against 150 mM $NaPO_4$, pH 7.4 containing 150 mM and 175 mM NaCl, respectively. This study demonstrates that with increasing plasmid concentration, there is a decrease in the encapsulation efficiency. Thus, as seen in FIG. 5, sufficient lipid is required in order to have significant loading of the plasmid into particles.

[a]Nicomp analysis of mean particle size, gaussian dist., volume weighting, before DEAE cleaning and isolation FIGS. 7 through 11 represent examples where NaCl/phosphate buffers are applied. The effect of a small change in DODAC (cationic lipid) concentration on the encapsulation efficiency is shown in FIG. 7. The % encapsulation as a function of NaCl concentration is presented in FIG. 8 for four different DODAC concentrations. The NaCl concentration required increased with increasing DODAC concentration. Similarly, the phosphate concentration was adjusted to obtain good encapsulation at different DODAC concentrations (see, FIG. 9). An additional effect on the encapsulation efficiency was observed by the lipid and polynucleotide concentration, respectively (see, FIGS. 9, 10 and 11).

Figures 12A, 12B, 12C:
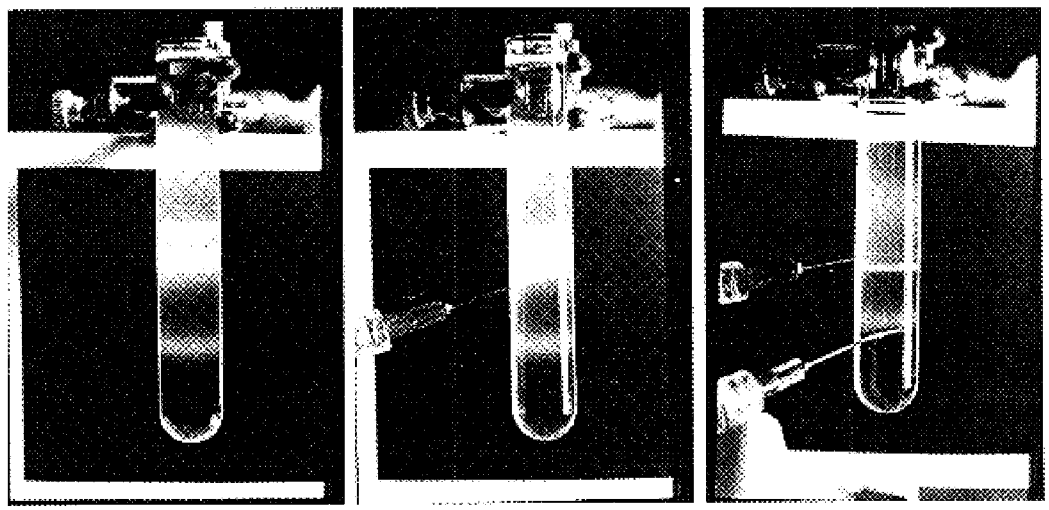
FIG. 12. Sucrose density gradient isolation of an INEX TCS. Panel A: Separation of TCS formulation loaded with plasmid (lower band) from empty vesicles (upper bands) on the gradient after 12 hr centrifugation at 36,000 rpm (SW 41 Ti Rotor). Panel B: Removal of empty liposomes (non-DNA associated). Panel C: Removal of the DNA-loaded TCS from the gradient. Empty vesicles are removed from the TCS formulation using sucrose gradient isolation after the nonencapsulated plasmids are removed on a column of DEAE-Sepharose. In this preparation, a formulation containing 24 mol % DODAC (200 μg DNA/10 mg plasmid) was loaded onto a typical sucrose gradient which contained (from bottom to top) 10% (2 mL), 5% (4 mL), and 2.5% (3 mL) sucrose in 20 mM HEPES buffered saline. The gradient was centrifuged for 14 hr at room temp. In this case, the DNA loaded TCS were removed using a syringe; however, fractions can be removed from the top of the gradient.
Figure 13:
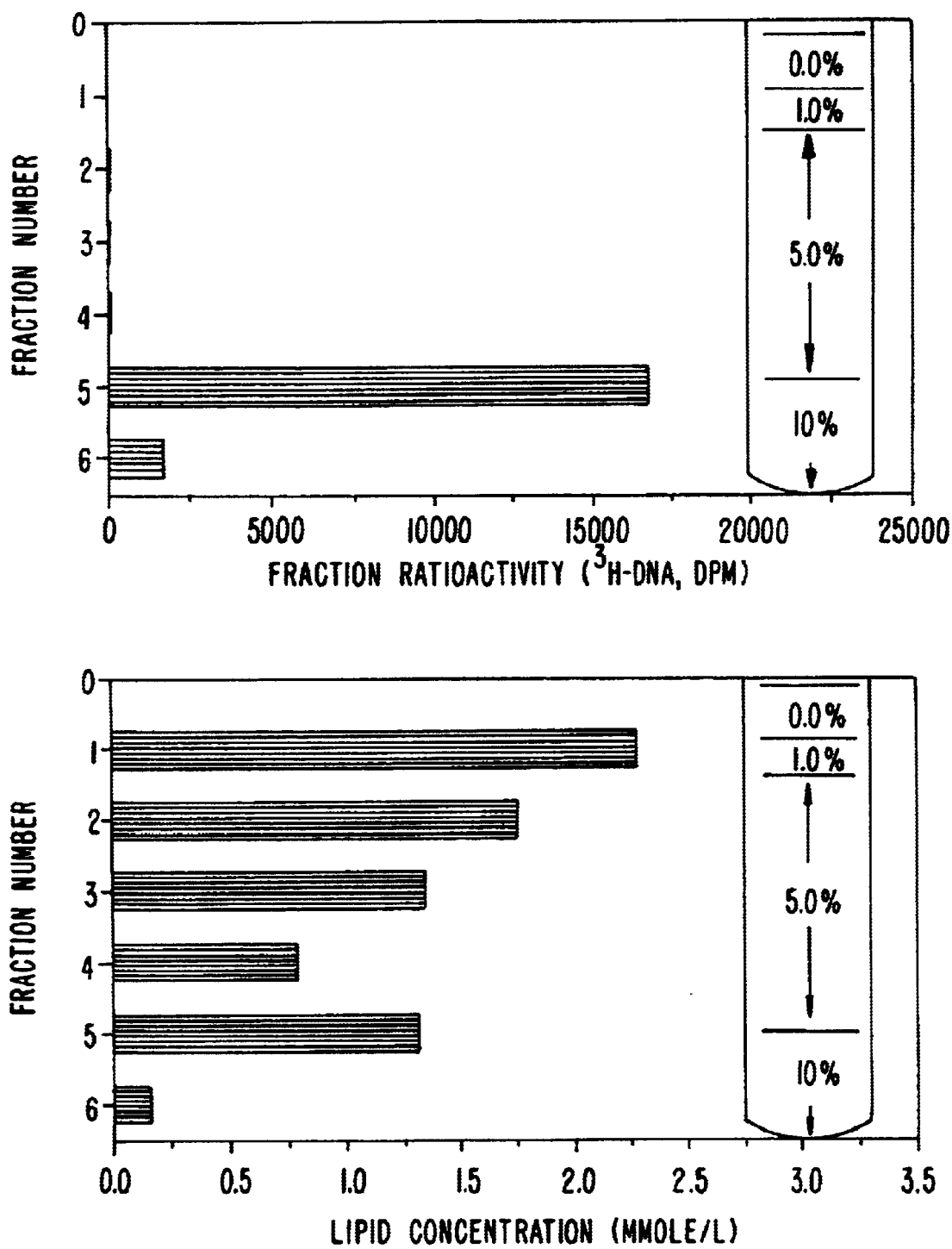
FIG. 13. Distribution of lipid and DNA for a typical TCS containing 21 mol % DODAC after centrifugation on a sucrose density gradient for 5 hrs at 36000 rpm at 20° C. using a Beckman ultracentrifuge with a SW41 Ti rotor. Fractions of 2 mL were removed from top to bottom and assayed for DNA and lipid concentration. Upper panel: distribution of $^3$H-labelled DNA. Lower panel: distribution of $^{14}$C-labelled lipid on the sucrose gradient.
Figure 14A:
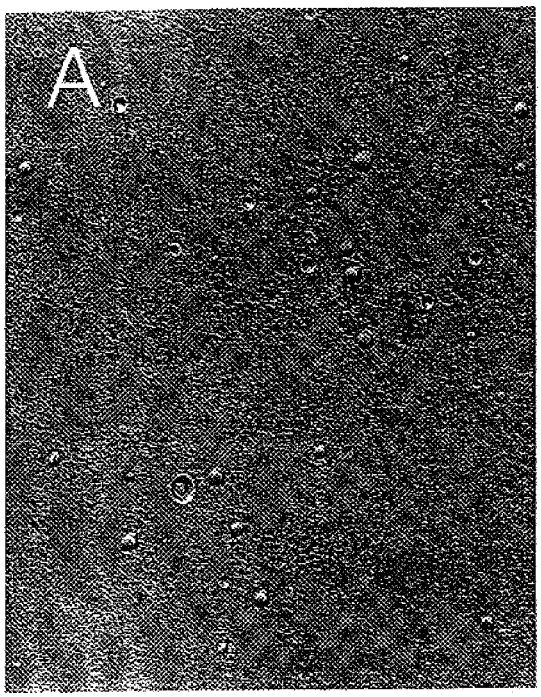
FIG. 14. Electron-microscopy (EM) of various INEX TCS formulations. (A) Freeze-fracture EM of a formulation containing 20 mol % DODAC. (B) Freeze-fracture EM of a formulation containing 42.5 mol % DODAC formulation.
Figure 14B:
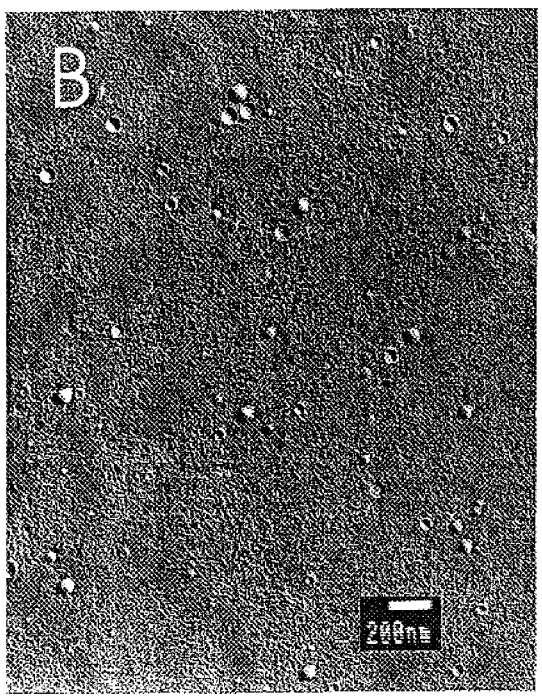

The particles/vesicles containing polynucleotides can be separated from empty vesicles by density gradient centrifugation. DNA containing particles accumulate at a higher sucrose concentration (i.e., lower band) than the empty vesicles (i.e., upper two bands) (see, FIGS. 12 and 13). FIG. 13 shows the results of lipid and DNA analysis of the different gradient fractions, with DNA exclusively in the lower band. The size distribution of the particles/vesicles in the lower band is very narrow (small number for polydispersity, $\chi^2$) and the mean diameter increases slightly with increasing DODAC concentration from about 65 to 94 nm (see, Table 2). The particles isolated from formulations with different DODAC concentrations had a similar lipid/DNA ratio (see, Table 3). The homogeneous size distribution of the isolated particles was also seen by electron microscopy (see, FIG. 14).

TABLE 2

Effect of Isolation on Particle Size Parameters

| | Particle Size Parameters | | | |
|---|---|---|---|---|
| | Before Isolation | | After Isolation | |
| Formulation % DODAC | Mean diameter (nm) | $\chi^2$ | Mean diameter (nm) | $\chi^2$ |
| Citrate | | | | |
| 7% | 37 ± 18 | 0.92 | 101 ± 11 | 0.36 |
| 17.1% | 39 ± 20 | 2.7 | 96 ± 20 | 0.2 |
| 22.2% | 43 ± 22 | 2.6 | 92 ± 25 | 0.1 |
| 32.0% | 53 ± 35 | 23 | 114 ± 57 ± | 1.7 |
| Phosphate | | | | |
| 20% | 178 | 22.9 | 64.0 | 0.3 |
| 24% | 250 | 78.6 | 77.2 | 0.2 |
| 30% | 109 | 1.77 | 89.3 | 0.18 |
| 42.5% | 131 | 2.96 | 93.8 | 0.31 |

TABLE 3

Lipid/DNA ratio of TCS after isolation.

| | Total Lipid/DNA ratio (mg/mg) | |
|---|---|---|
| Mol % DODAC | Before Sucrose Gradient Isolation | After Sucrose Gradient Isolation |
| Citrate | | |
| 17.1% | 30.3 | 15.9 |
| 22.2% | 45.0 | 14.0 |
| 23.0% | 56.4 | 16.2 |
| Phosphate | | |
| 20 | 48.8 | 14.8 |
| 24 | n.d. | 16.6 |
| 30 | 66.3 | 18.5 |
| 42.5 | 53.2 | 13.5 | n.d. - not determined

Figure 16:
FIG. 16. Serum and DNAse stability of plasmid, Free, in complexes (INEX100.3, complexes prepared by mixing DODAC/DOPE liposomes with pINEXL018) and encapsulated in INEX TCS. Agarose gel electrophoresis of pIN-EXL018 phenol-chloroform extracted after treatment with 80% normal mouse serum. Lanes 1–4: Free pINEXL018; Lanes 5–8: pINEXL018 encapsulated 42.5% DODAC containing TCS; Lanes 9–12: DOPE:DODAC complexed-pINEXL018. This study illustrates that the encapsulated DNA remains intact after treatment with serum and DNAse, while demonstrating that complexed DNA is not as nuclease stable.
Figure 17:
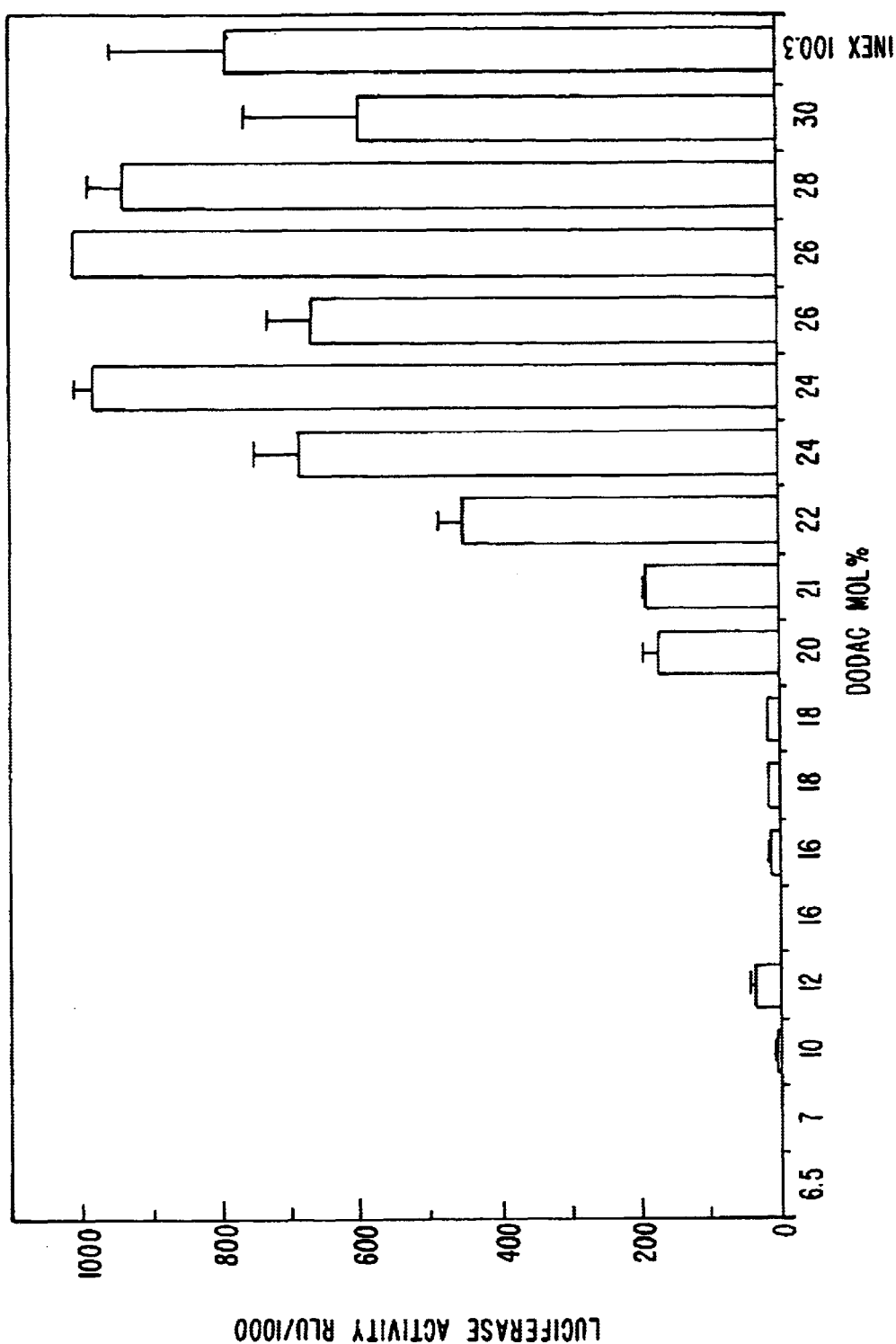
FIG. 17. Effect of DODAC concentration in TCS on the transfection of COS-7 cells in culture using isolated TCSs prepared with pINEXL018 and DODAC/DOPE/PEG-Cer-C8 by the detergent dialysis method using citrate buffer. Cells (40,000/well) were seeded in 24 well plates 24 hr before transfection. The dose was 1.0 μg/well and the luciferase activity was assayed at 48 hr time point (n=3). INEX100.3 represents complexes prepared by mixing DODAC/DOPE liposomes with pINEXL018.
Figure 18:
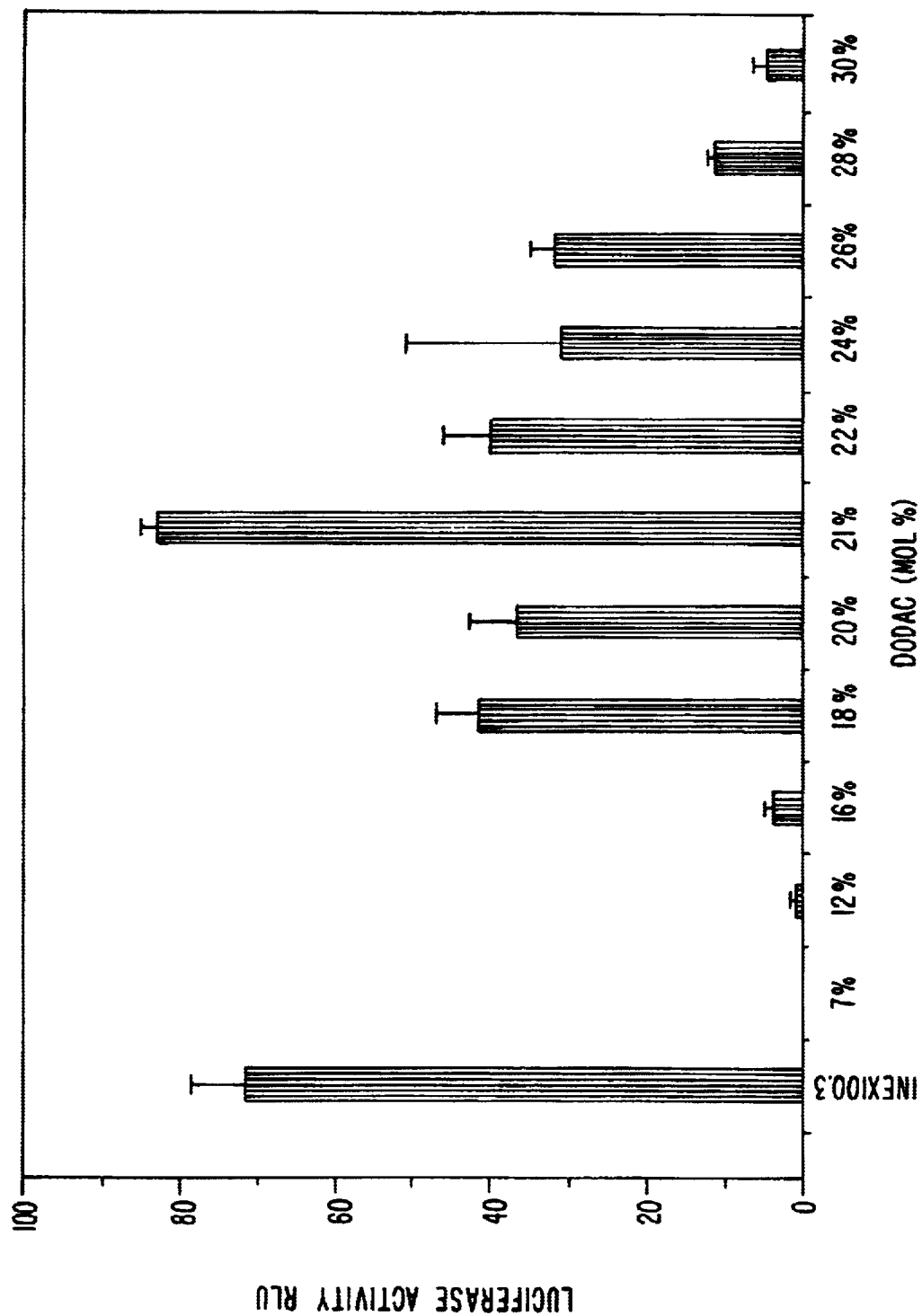
FIG. 18. Effect of DODAC concentration in TCS on the transfection of Hep-G2 cells in culture using isolated TCSs prepared with pINEXL018 and DODAC/DOPE/PEG-Cer-C8 by the detergent dialysis method using citrate buffer. Cells (40,000/well) were seeded in 24 well plates 24 hr before transfection. The dose was 0.3 μg/well and the luciferase activity was assayed at 48 hr time point (n=3). INEX100.3 represents complexes prepared by mixing DODAC/DOPE liposomes with pINEXL018.
Figure 20:
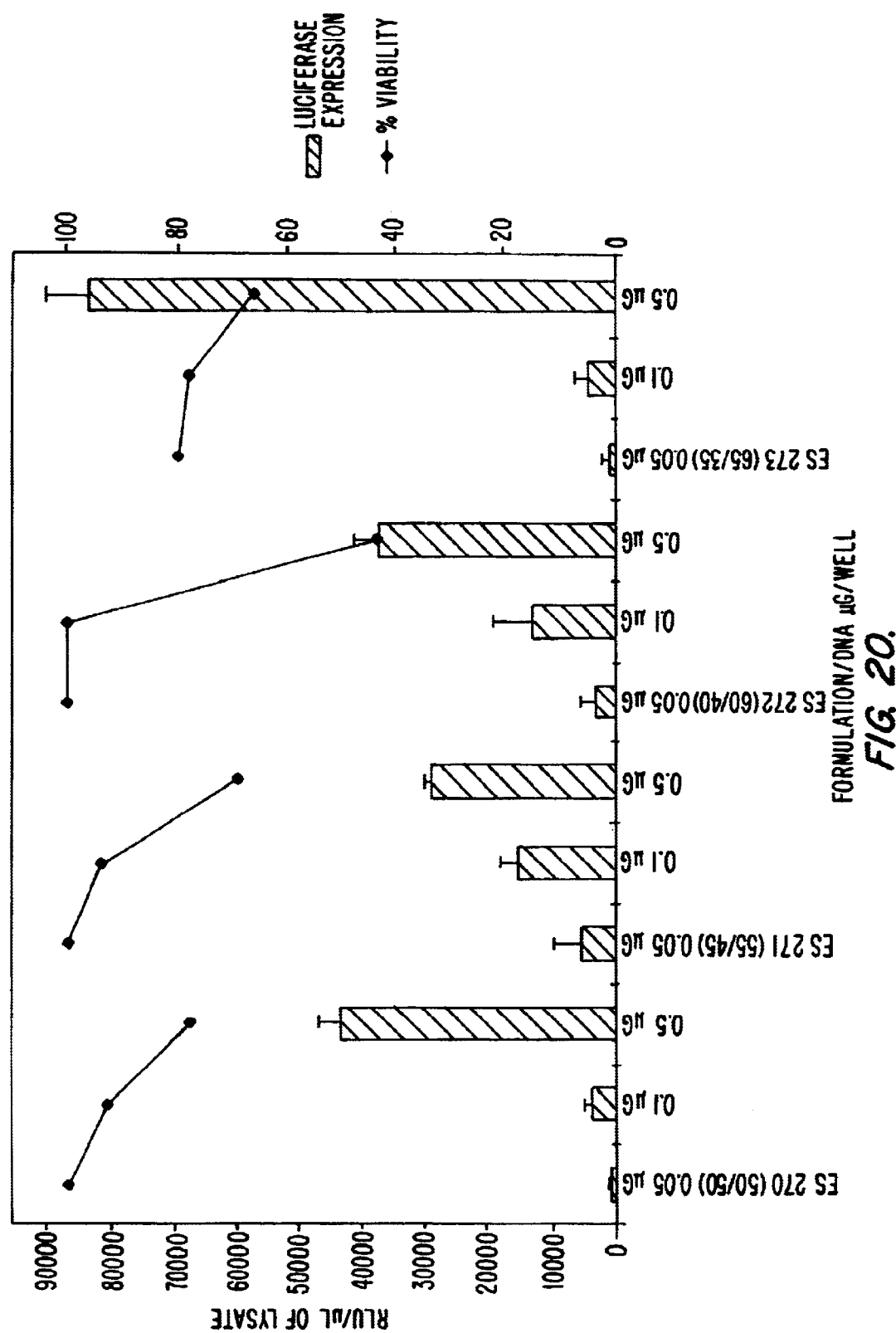
FIG. 20. In vitro transfection study. Effect of the dose and DODAC concentrations of TCS prepared by phosphate buffer dialysis on the transfection and viability of COS-7 cells in culture. INEX TCS formulations containing 42.5, 38, 34 and 30 mol % DODAC (expressed as DOPE/DODAC ratios 50/50, 55/45, 60/40 and 63/35, respectively) were incubated with 35,000 cells/well at doses of 0.05, 0.1, 0.5 μg DNA. After 24 hr incubation, the cells were resuspended, lysed and measured for viability and luciferase activity (expressed as relative luminescence units). This study demonstrates that decreasing the DODAC concentration in non-isolated TCS increases the transfection activity and decreases the relative toxicity of the formulation.
Figure 21:
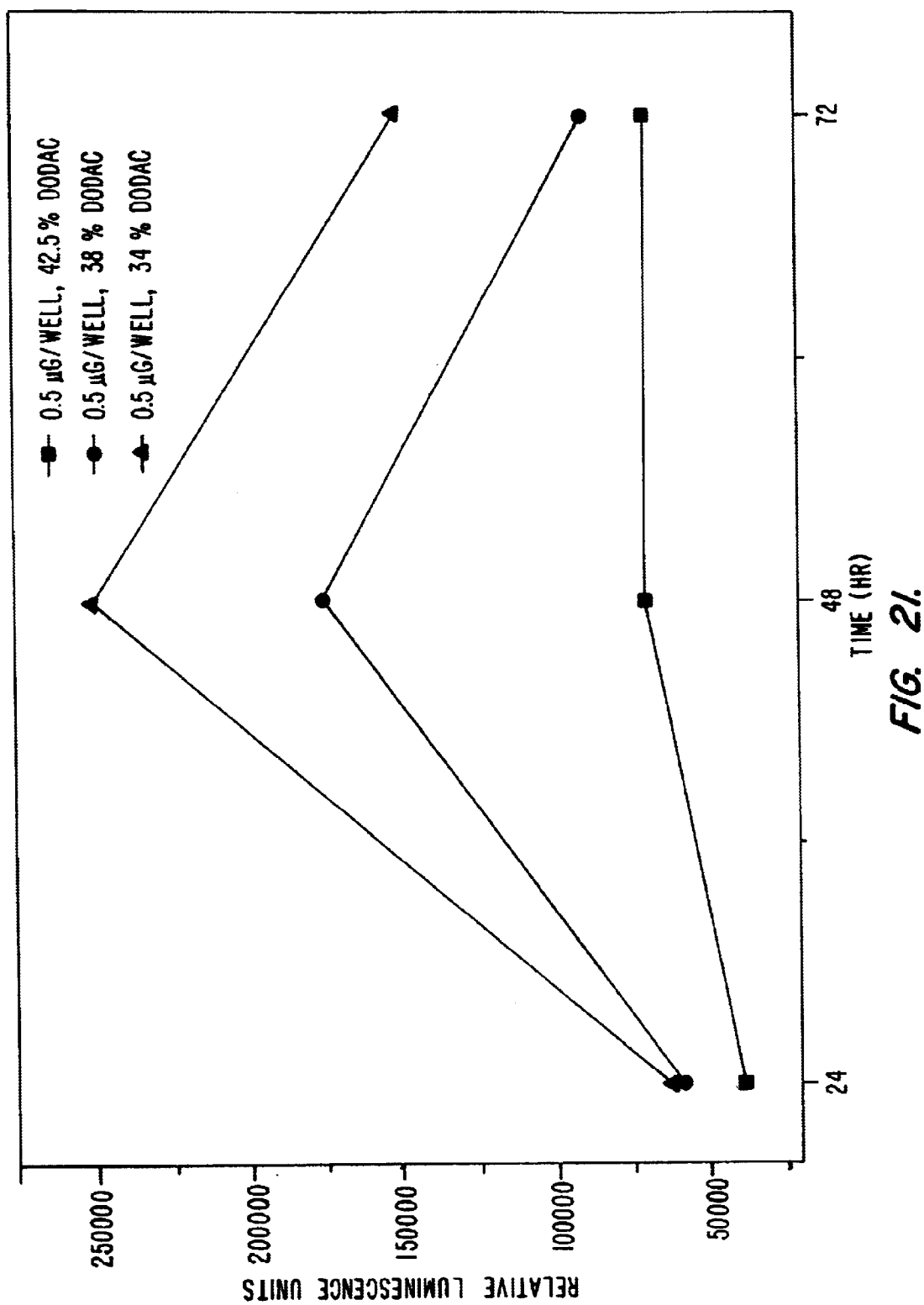
FIG. 21. Time course of transfection activity of TCS prepared by the phosphate dialysis method. COS-7 cells were incubated with 0.5 μg non-isolated TCS under the conditions described in FIG. 14. After incubation for 24, 48 and 72 hours, transfection was measured as luciferase activity. This study illustrates that in vitro transfection increases for up to 48 hr and is sustained for well over 72 hr. As observed in FIG. 14, transfection activity increased with decreasing DODAC concentration.
Figure 22:
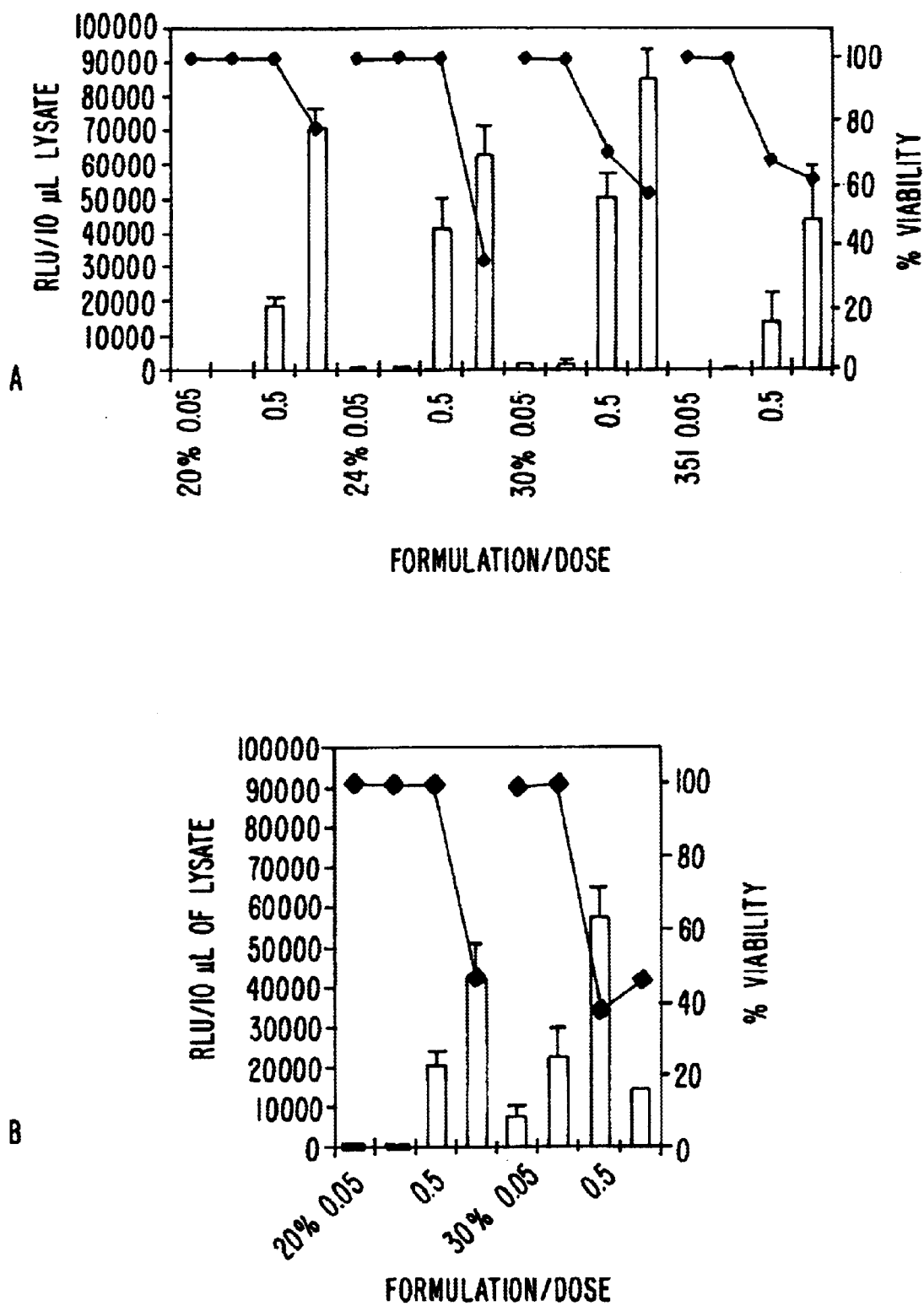
FIG. 22. Effect of sucrose density gradient isolation of TCS prepared by the phosphate dialysis method on the transfection and viability of COS-7 cells in culture. COS-7 cells were incubated with both isolated and nonisolated TCS at 0.05, 0.1, 0.5 and 1.0 μg of DNA. TCS contained DODAC concentrations of 20, 24, 30 and 42.5 mol %. After 24 hours the cell viability and luciferase activity was measured. In total, FIGS. 14–16 demonstrate that TCS mediated transfection is dose dependent. Maximal in vitro transfection activity is obtained at 30 mol % DODAC. Decreasing the TCS DODAC concentration reduces toxicity. Removal of empty TCS by sucrose density gradient isolation also decreases the toxicity of the formulations and increases the in vitro transfection activity.

The DNA inside the particles was largely protected from serum nucleases and DNase (see, FIGS. 15 and 16). Formulations were incubated in either DNase or serum, and then separated by gel chromatography. FIG. 15 illustrates the separation profile from Sepharose CL-4B gel filtration chromatography for free plasmid DNA after serum incubation, and for a formulation with 21 mol % DODAC before sucrose density gradient isolation (see, FIG. 15A) and after the isolation (see, FIG. 15B). DNA cleaved by nucleases eluted in fractions >7, while the encapsulated intact DNA eluted together with the lipids in the exclusion volume fractions 4–7. The integrity of the encapsulated DNA was characterized further by electrophoresis and, as illustrated in FIG. 16, the plasmid remained intact.

2. Transfection: In Vitro

The transfection activity and toxicity of formulations containing various concentrations of the cationic lipid DODAC were tested in vitro in COS-7 and Hep-G2 cells (see, FIGS. 17 through 22). Luciferase plasmid was formulated and expression of luciferase was determined at times indicated. Cell viability was used as an indication for toxicity. The transfection efficiency was determined as a function of DODAC concentration used in the formulation (see, FIGS. 17 through 22). Furthermore, transfection activity was evaluated as a function of the DNA dose applied (see, FIGS. 19 and 20) and as a function of time (see, FIG. 21). There is limited transfection activity with formulations containing less than 16–18 mol % DODAC. The best transfection activities are obtained with DODAC concentration in the range of 20–30 mol % in the formulations. The cell viability indicates that toxicity increases significantly with preparations containing >30 mol % DODAC. The toxic effect of the preparation particularly for formulations with high DODAC concentrations can be reduced greatly by removal of the empty vesicles by gradient centrifugation. Furthermore, these isolated preparations showed a significant increase in the transfection activity (see, FIG. 22).

3. Transfection: In Vivo

Figure 23:
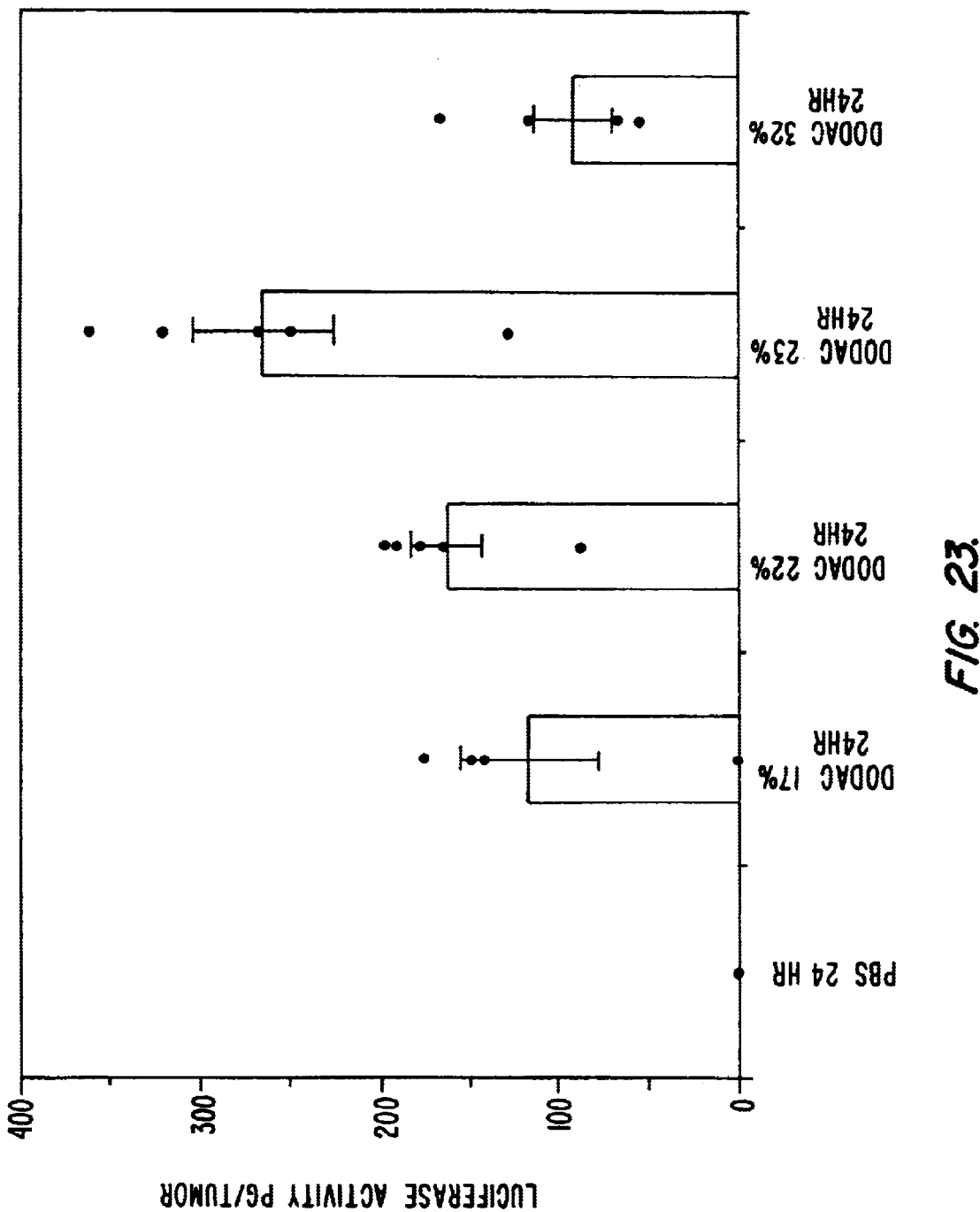
FIG. 23. In vivo, intraperitoneal transfection study for TCS containing various DODAC concentrations in TCS prepared by detergent dialysis in citrate buffer after isolation on transfection of B16 i.p. tumors. The TCSs were composed of pINEXL018/DODAC/DOPE/PEG-Cer-C8. TCS (30 μg DNA/500 μl/mouse) formulations were injected i.p. into mice 7 days after tumor seeding. Tumors were removed from mice 24 hours after treatment and were assayed for luciferase activity.
Figure 24:
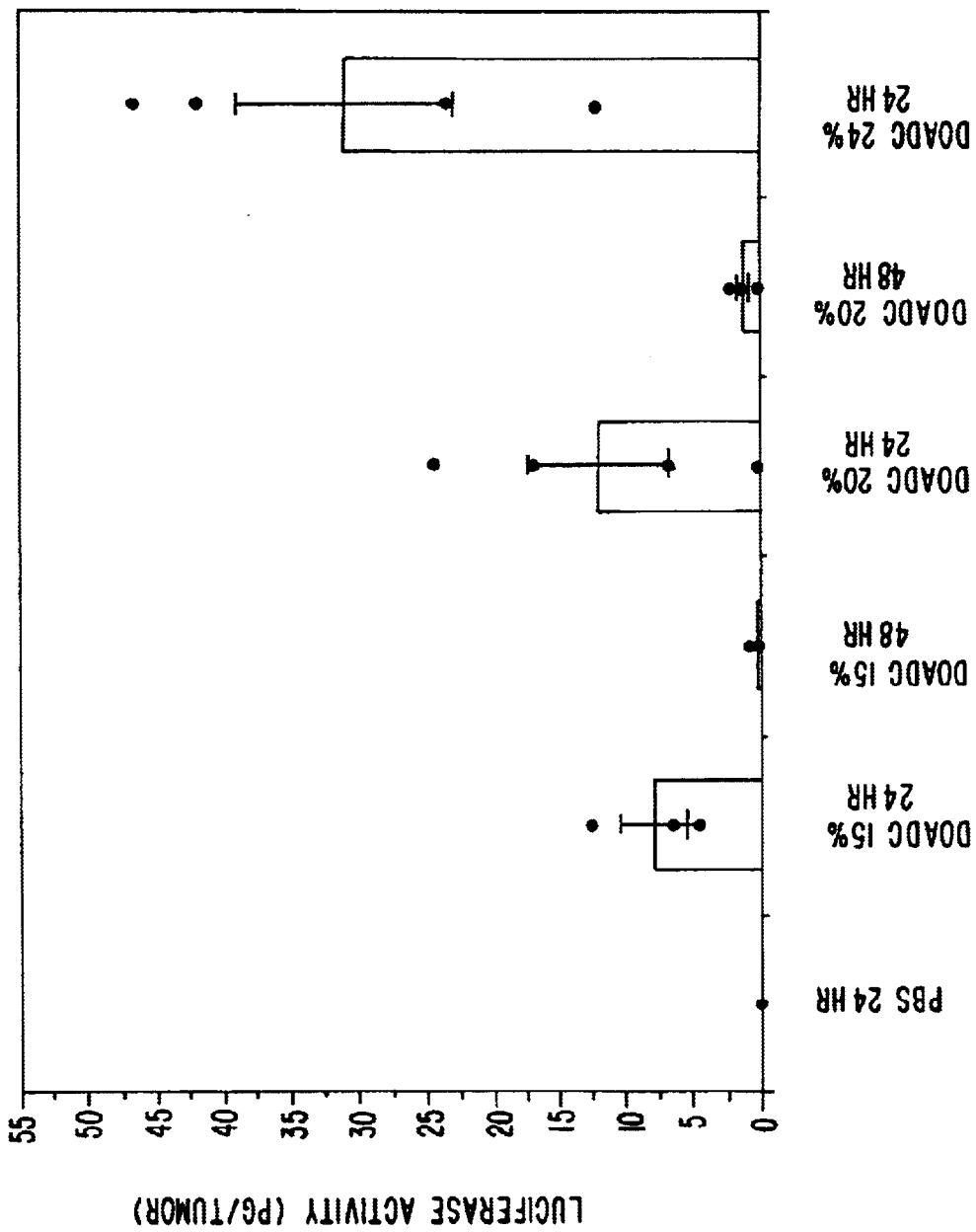
FIG. 24. Effect of time on the transfection of i.p. B16 tumors. Isolated TCS (30 μg DNA/500 μl/mouse) of various DODAC concentrations prepared by detergent dialysis in citrate buffer were tested for luciferase transfection activity 24 and 48 hours after injection. The TCSs were composed of pINEXL018/DODAC/DOPE/PEG-Cer-C8.
Figure 25:
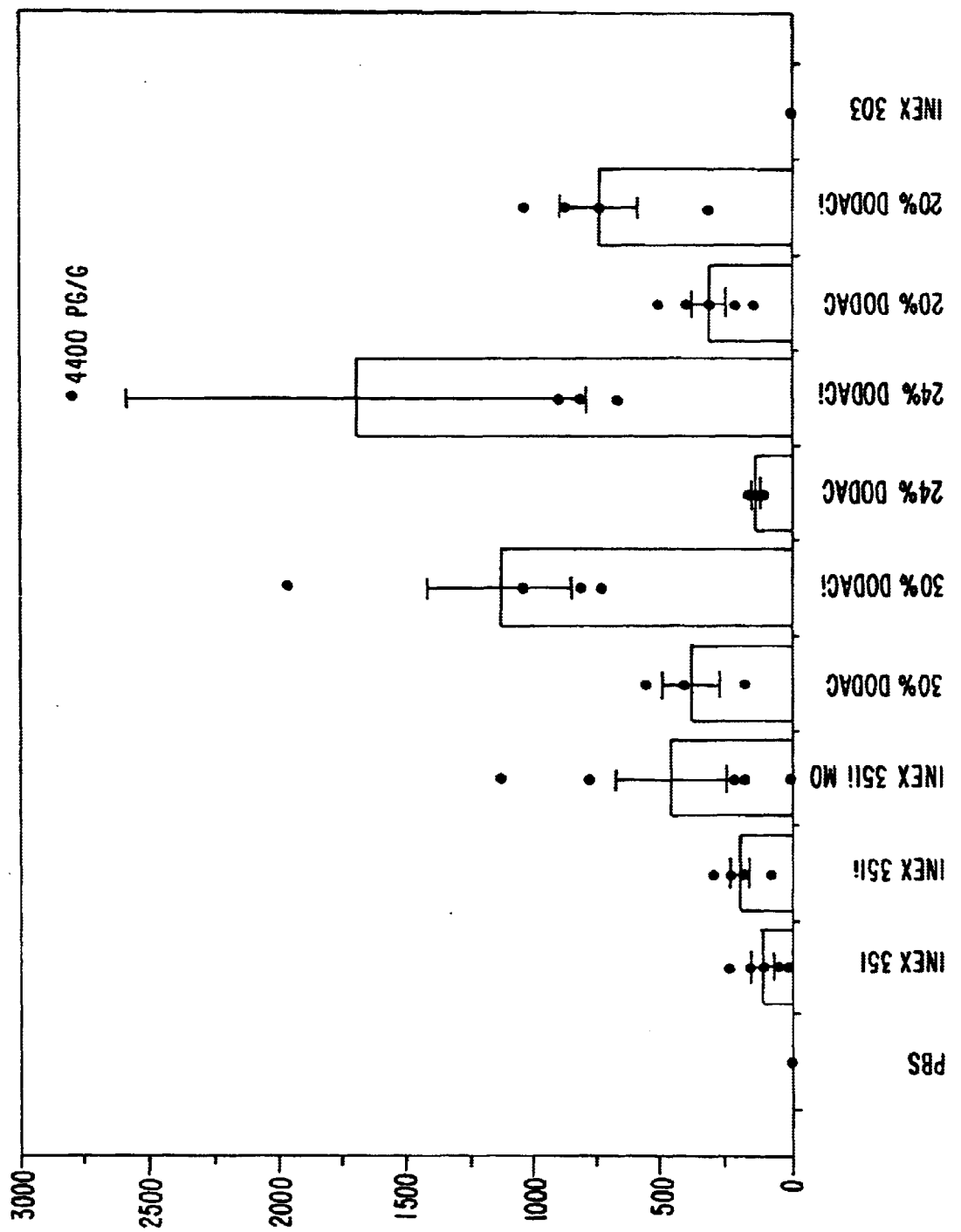
FIG. 25. Comparison of the transfection activity of isolated vs. non-isolated TCS formulations. TCS containing DODAC concentrations of 42.5 mol % 30 mol %, 24 mol % and 20 mol % DODAC prepared by phosphate dialysis were injected i.p. at 30 μg DNA into mice 7 days after tumor seeding. Tumors removed from mice 24 hours after administration were assayed for luciferase activity. This study demonstrates that these TCS formulations transfect in vivo as well as in vitro. In addition, removal of the empty liposomes by sucrose density gradient isolation results in increased transfection activity.
Figure 26:
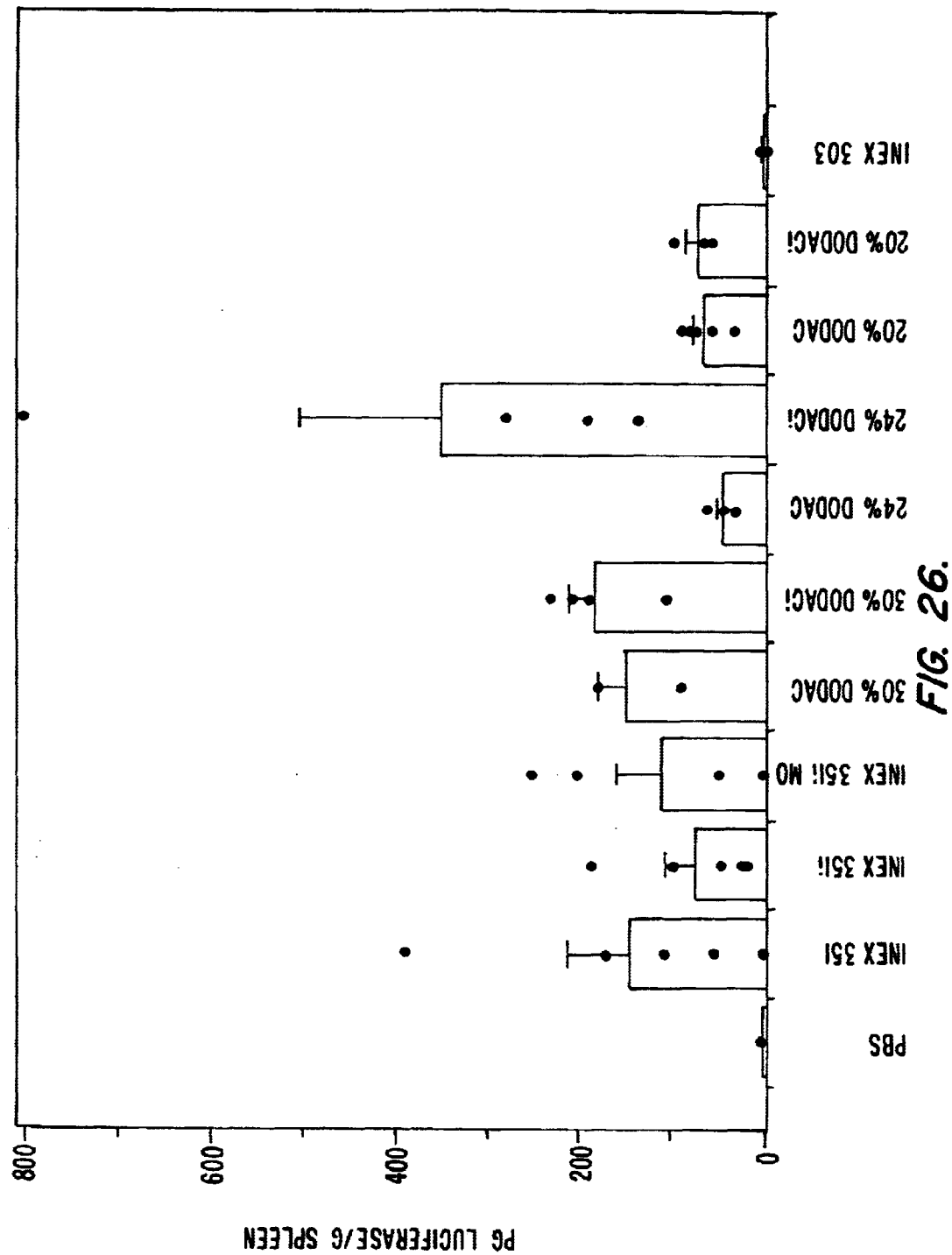
FIG. 26. The effect of DODAC TCS concentration on the transfection of mouse spleens after i.p. administration. TCS formulations described in FIG. 19 were injected i.p. at 30 μg DNA into mice 7 days after tumor seeding. Spleens removed from the tumor bearing mice 24 hours after administration were assayed for luciferase activity.
Figure 27:
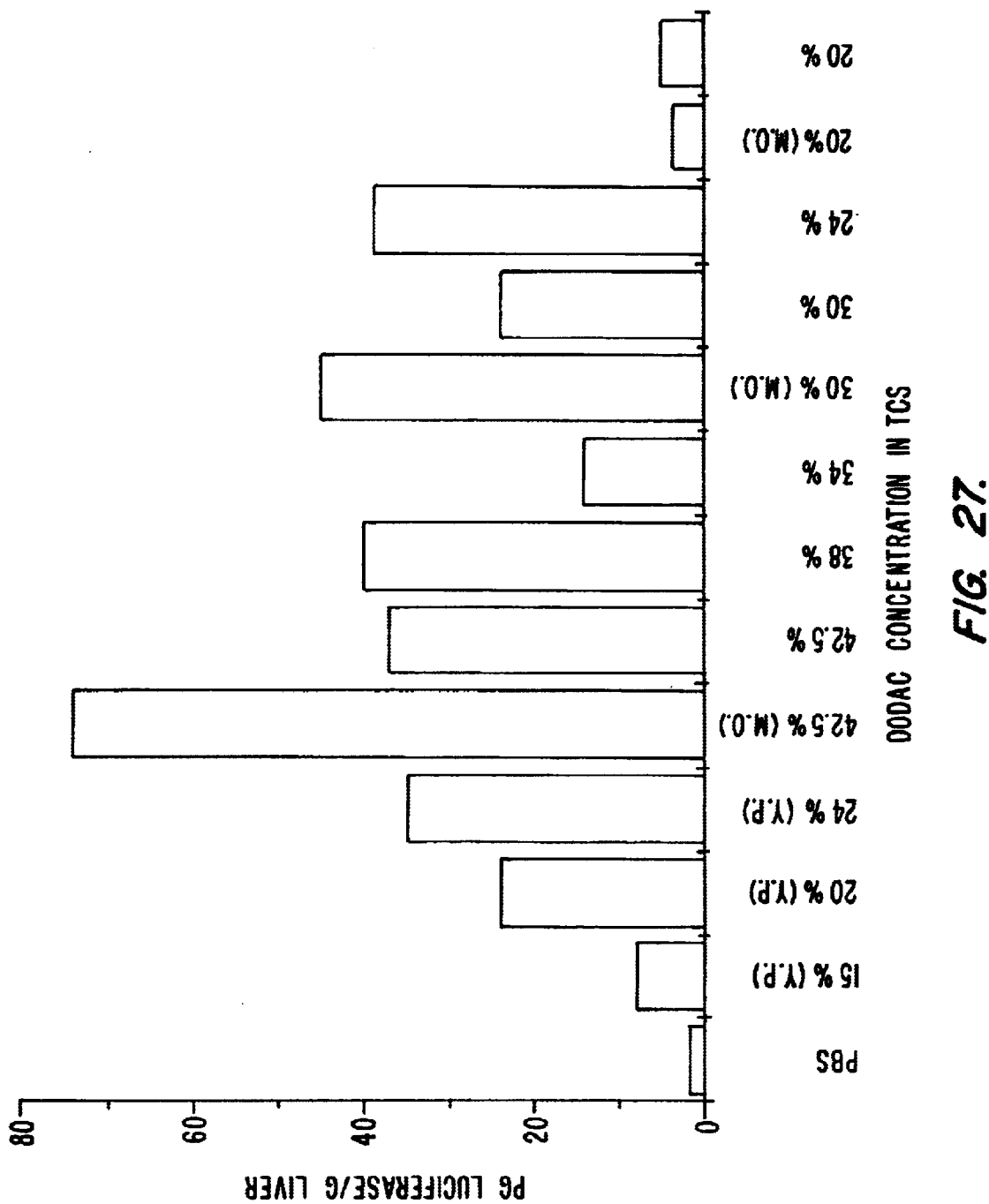
FIG. 27. The effect of DODAC TCS concentration on the transfection of mouse liver after i.p. administration. TCS formulations described in FIG. 19 were injected i.p. at 30 µg DNA into mice 7 days after tumor seeding. Livers removed from the tumor bearing mice 24 hours after administration were assayed for luciferase activity. The studies described in FIGS. 21 and 22 demonstrate that it is possible to transfect normal organs as well as tumor tissue after i.p. administration of TCS formulation.
Figure 28:
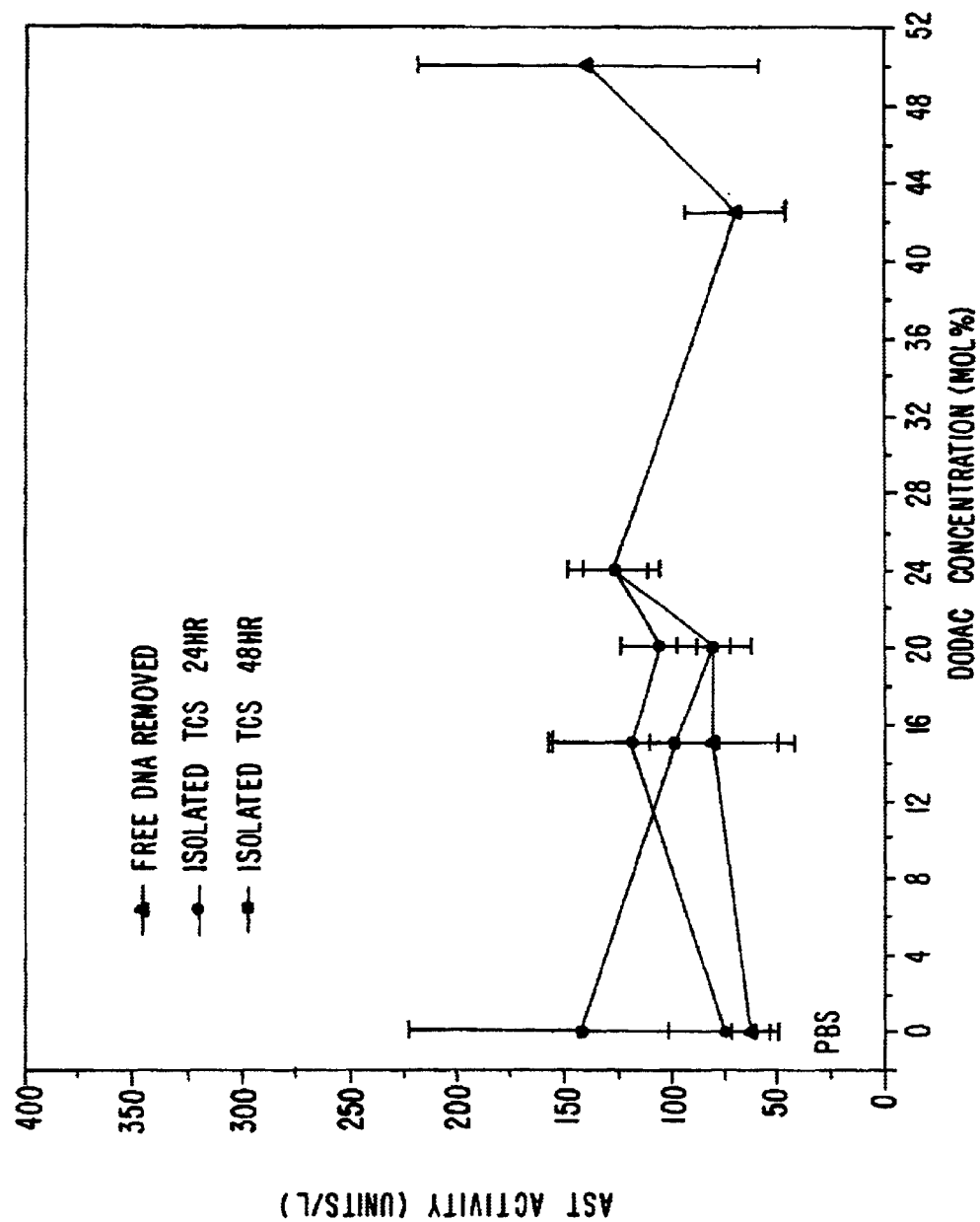
FIG. 28. TCS toxicity study was carried out by monitoring the plasma aspartate aminotransferase (AST) levels after i.p. administration of TCS containing various concentrations of DODAC. Isolated TCS composed of pINEXL018/DODAC/DOPE/PEG-Cer-C8 prepared by detergent dialysis in citrate buffer were injected i.p. into mice 7 days after tumor seeding. Blood was removed from mice 24 hours after administration and was assayed for AST activity. This study demonstrates that there is little significant tissue or organ damage associated with TCS formulations administered by the i.p. route.

A murine tumor model was chosen to determine the transfection activity in vivo. Mice (C57) were injected by the intra peritoneal (i.p.) route with 100,000 B16 tumor cells. Formulations were administered i.p. on day 7 of B16 tumor growth. After 24 hours (unless indicated otherwise), the animals were sacrificed and the tumors, liver and spleen were analyzed for luciferase expression. The tumor transfection activity was dependent on the concentration of DODAC in the formulation (see, FIGS. 23 and 25). The highest luciferase activity was observed from formulations with 20 to 30 mol % DODAC. Isolated preparations consistently showed increased transfection activity when compared to nonisolated preparations for the same DNA dose (see, FIG. 25). The luciferase expression in tumors was higher 24 hours after injection than after 48 hours (see, FIG. 24). Luciferase activity was also observed in liver (see, FIG. 27) and in spleen (see, FIG. 26). None of the formulations with the different DODAC concentrations showed significant liver toxicity following i.p. administration as based on the AST levels in the plasma (see, FIG. 28).

VII. EXAMPLE 2

Immunological Effect of Repeated Injections of Lipid-Nucleic Acid Compositions

A. Materials and Methods

A formulation of plasmid with DOPE:DODAC:PEG-Ceramide-C8 (61:24:15 mol %) (INEX324) was prepared using the methods of Example 1. The formulations were prepared containing pCMV(3 and pINEXL018. They were isolated and assayed as described in Example 1.

1. Administration of INEX324 to Balb/c Mice.

Mice, 12 per group, were injected intravenously (i.v.) with TCS formulations as described below. In this study four injections were given at intervals of seven days over a period of five weeks (Table 4). Group A was injected with INEX324 expressing LacZ reporter gene on day 0, 7 and 14 (150 $\mu$l per mouse of INEX324-LacZ, 75 $\mu$g DNA). Two weeks after the last LacZ injection, mice were injected with INEX324-Luc (150 $\mu$l per injection, 80 $\mu$g DNA). To evaluate the immunogenicity of INEX324 lipid, Group B received three injections of INEX324 empty vesicles (150 $\mu$l per mouse) and one injection of INEX324-Luc two weeks later. Group C served as a base-line control, mice were given 150 $\mu$l of diluent at each time point. Mice from Group D received three diluent injections, followed by a single injection of INEX324-Luc, and served as a positive control for luciferase expression. Three mice from each group were sacrificed at 18 hours after each injection, or 24 hours prior to the following injection. Blood was collected and the serum samples were analyzed for the presence of antibodies specific for $\beta$-galactosidase using an ELISA assay. Spleens were harvested and splenocytes were processed for various immunological assays: carrier specific, $\beta$-gal, LacZ, or mitogen induced clonal expansion and cytokine (IL-2 and IL-4) release. Splenocytes were monitored for expression, of differentiation (CD4, CD8, CD22, CD11b) and activation (CD86, MHC-II, Ly-6A/E, CD54 and CD25) markers. The remaining mice from all groups were sacrificed 12 h following the last injection with INEX324-Luc. At this point, the organs (lung, liver and spleen) were fast frozen in liquid nitrogen and assayed for luciferase expression.

TABLE 4

Treatment Schedule

| Group | Formulation | day 0 1st injection | Day 7 2nd injection | day 14 3rd injection | day 28 4th injection |
|---|---|---|---|---|---|
| A | 324/LacZ | 324/LacZ | 324/LacZ | 324/LacZ | 324/Luc |
| B | 324 lipid | 324 lipid | 324 lipid | 324 lipid | 324/Luc |
| C | Diluent | Diluent | Diluent | Diluent | Diluent |
| D | Diluent | Diluent | Diluent | Diluent | 324/Luc |

2. Flow Cytometry Analysis.

Splenocytes from all groups were analyzed for expression of differentiation and activation markers. Spleen cells (1×10$^6$) were stained with appropriate PE-conjugated antibodies (anti-CD22, anti-CD4, anti-CD8, anti-CD11b, anti-CD54, anti-CD86, anti-Ly6A/E and anti-CD25) and phenotypic analysis was performed on a FACSsort flow cytometer (Becton Dickinson, San Jose, Calif.). Splenocytes were analyzed either after 18 h and 6 days after in vivo treatment.

3. Cell Proliferation Assay.

Unseparated spleen cells were tested in vitro for their ability to proliferate upon re-stimulation with the empty INEX324 vesicles, INEX324-LacZ formulation, LacZ, transgene product (r-$\beta$-galactosidase), or with polyclonal activators for T (Concanavalin A, Con A) and $\beta$ cells (Lipopolysaccharide, LPS). Single-cell suspensions of lymphocytes were prepared from whole spleens by grinding the spleens using the frosted ends of sterile glass slides in RPMI media containing 10% FBS. The suspension was allowed to settle standing on ice in a 15 ml polypropylene culture tube. An isolated cell suspension was separated from debris by removing the supernatant and the cell number was quantified using a Coulter counter (Coulter Instruments, Miami, Fla.). Aliquots of cell suspensions (100 $\mu$l, 5×10$^6$/ml) in the above media were placed into 96-well plates along with the equal volumes of various appropriate stimuli. Cells were labeled with $^3$H-thymidine for 48 h, and after 3 days incubation, they were harvested. The levels of incorporated radioactivity were measured in a scintillation counter. $^3$H-thymidine incorporation is expressed total $^3$H-incorporation (DPMs), or as a mean percentage (±SD) of media control and plotted versus lipid concentration values.

4. Measurement of Cytokine Release.

Splenocytes (1×10$^6$ cells/ml) were either nonstimulated or cultured in the presence of various concentrations of either empty INEX324 vesicles, or INEX324-LacZ formulation at different times after culture initiation (24 h and 48 h). The levels of cytokine in the cell culture supernatant (Interleukin-2 and Interleukin-4) were determined by an ELISA assassy (below).

5. Cytokine ELISA Assays.

Cytokine-specific ELISA assays were performed using the protocol and specific anti-interleukin antibodies provided by reagent mini-kit (Endogen, Woburn MA). Briefly, Immuno-module (F8-maxisorb) 96-well plates were coated overnight with anti-IL-2, or anti-IL-4 antibody. Plates were washed with PBS-Tween 20 (0.05%) and blocked with PBS-Tween 20-BSA (2%) for 1 hour at room temperature. Supernatant samples and standards (diluted in blocking buffer) were added and allowed to incubate overnight. Plates were washed and biotinylated anti-IL-2 or anti-IL-4 antibody was added. After 2 hours incubation, plates were washed and HRP-Extravidin, followed by TMB, was added to each well. Plates were read on a plate reader at $OD_{450nm}$. The amount of released cytokine was determined by comparing the O.D. of test supernatants to a standard curve of serially diluted cytokine standards.

6. ELISA for Detection of β-gal-specific Antibodies.

β-gal specific antibodies in the serum were measured using an ELISA assay. Immuno-module (F8-maxisorb) 96-well plates were coated overnight with r-β-gal (10 μg/ml, 100 μl/well) diluted in bicarbonate buffer (pH 9.6). Plates were washed with PBS-Tween 20 (0.05%) and blocked with PBS-Tween 20-BSA (1%) for 30 minutes. Serum samples and standard anti-β-gal IgM and IgG, diluted in blocking buffer, were added to the wells and allowed to incubate overnight. Plates were washed and biotinylated anti-mouse IgG antibody was added. After 2 hours incubation, plates were washed and HRP-Extravidin, followed by TMB substrate, was added to each well. The development of a colored reaction product was quantified on plate reader at $OD_{450}$. The amount of IgG was determined by comparing OD of test serums to a standard curve of serially diluted antibodies as standards.

7. In Vivo Gene Expression.

Balb/c mice were given 3 intravenous injections of INEX324-LacZ or empty INEX324 vesicles on days 0, 7 and 14. After two additional weeks, mice from all groups (except for the diluent treated group) received one injection of INEX324-Luc (80 μg of DNA) and 12 h later the organs (liver, lung, spleen) were collected and assayed for luciferase activity. A standard assay for the determination of luciferase from the tissue samples was employed. Tissue homogenization was performed using a FastPrep Instrument (FastPrep™ FP120 Instrument, Bio 101) using supplied tubes and beads (FastDNA tubes with MS Matrix). Tissues were homogenized in Cell Culture Lysis Reagent (1×CCLR, Promega) supplemented with BSA (1 mg/ml). FastPrep Instrument settings: speed—5; time—8 sec twice. Samples were transferred to new microcentrifuge tubes and briefly centrifuged (2 min., 10,000 rpm) to remove debris. The luciferase assay was performed on luminometer (Dynatech Microlite™ ML3000) using a 96-well microlite plate. A set of purified luciferase standard solutions was prepared (Firefly luciferase) by serially diluting 1 μg/μl luciferase in 1×CCLR supplemented with BSA (1 mg/ml). For the standard curve, luciferase protein was diluted in a control tissue homogenate to compensate for quenching and 20 μl aliquots (in duplicates) were assayed for each sample/standard. Settings for Luminometer: grade—medium; delay time—2 sec; integrate time—10 sec; substrate—100 μl (Luciferase Assay System, Promega). The results were converted to pg of luciferase protein/g of tissue.

8. In Vitro Transfection of BHK Cells.

BHK-21 cells were plated at a density of $1\times10^6$ cells (in 10 ml media) per 75 cm² tissue culture flasks. The following day, when the cells were 60–70% confluent, the media was aspirated and replaced with 4.8 ml of fresh culture media 2–3 hours prior to transfection. INEX324-LacZ (12.5, 6.2 or 3.1 μg of DNA per $1\times10^6$ cells) was added to the culture media (total volume did not exceeded more than 200 μl) and particles were allowed to remain in contact with the cells for the next 24 hours (at 37° C., 5% $CO_2$). Separate flasks for appropriate transfection controls: untreated cells, lipid only, plasmid only, and gene unrelated plasmid/particles (i.e., INEX324-Luc) were included. The cell viability and gene expression assays were performed 24 hours post-transfection.

9. FACS Assay for in Vitro Detection of Transgene β-galactosidase.

Single cell suspensions from transfected cell monolayers were prepared by mechanical dissociation. Dissociated cells were transfered into polystyrene tubes, and stained for the presence of the transgene product, β-galactosidase, using the FDG assay. In this assay, aliquots containing $10^6$ cells were pelleted and re-suspended in 100 μl of staining medium in a 6 ml polystyrene FACS tube and were incubated for 10 min. at 37° C. for 10 minutes. The FDG reagent was diluted into 2 ml of distilled water and was pre-warmed to 37° C. for no more than 10 minutes. A 100 μl aliquot of the FDG solution was added to each sample. The suspensions were vortexed and incubated an additional minute at 37° C. After incubation, 1.8 ml ice-cold staining medium was added to each tube and the tubes were placed on ice in darkness. Each sample was read within 5 min. after staining using the FACSort flow cytometer.

B. Results and Discussion

1. Analysis of Differentiation Markers.

Spleen cells analyzed for the expression of differentiation markers were isolated, stained and assayed either 18 h, or six days following INEX324-LacZ administration. The analysis of differentiation markers 18 h after in vivo treatment shows that there are no appreciable differences in the frequency of cells expressing CD22 (B cells) and CD11b (macrophages) markers between the groups (Table 5). The percentage of $CD4^+$ cells and $CD8^+$ cells within the spleen cell population from INEX324-LacZ treated group was approximately 40% higher compared with diluent or lipid treated group, however, alteration in the ratio of $CD4^+$ and $CD8^+$ was not observed. Spleen cells were processed for the expression of the same set of differentiation markers six days following last injection. Examination of the spleen cell population from INEX324-LacZ treated group revealed changes in phenotypic profile of spleen cells: a moderate decrease in the percentage of T cells (15%) and a significant 30% decrease of $CD22^+$ cells. Furthermore, INEX324-LacZ treatment resulted in a five-fold increase of macrophage number as defined by expression of CD11b antigen, compared with diluent treated mice and those that received the empty liposome. It might be that repeated administration of lipid/DNA induces alteration in the pool of splenic cells, evidenced by the decreased number of lymphocytes subsets, T and B cells, and increased the number of macrophages. On the other hand, it is possible that the number of T and B cells is not decreased and these changes are due to the increased spleen cellularity in this group (40% increase compared with control groups).

A possible explanation for the observed increased spleen cellularity (also observed as splenomegaly) is an infiltration of monocytes into the spleen. In this case, the promoted infiltration of monocytes (and consequently an increased number of CD11b cells), would make the relative contribution of other cell subpopulations within unfractionated spleen samples appear relatively lower (Table 5). In addition, an increased number of macrophages suggests that INEX324 lipid is not toxic. Macrophages have an innate capacity for nonspecific phagocytosis of large quantities of foreign particles such as liposomes. Following internalization and processing of phagocytosed liposomes, their survival depends on the toxicity of the liposomal constituents. In the present study, repeated administration of INEX324 lipid is not accompanied with a decrease in CD11b$^+$ cells, on the contrary, their number is significantly increased and this strongly indicates that INEX324 lipid and INEX324/DNA are not toxic, even following repeated systemic administration.

LacZ-formulation, LacZ (naked DNA), with transgene product (r-β-galactosidase), or with polyclonal activators for T (Con A) and B (LPS) cells. The immunogenicity of INEX324 lipid and INEX324-LacZ formulation was evaluated using three concentrations of lipid (0.005, 0.01 and 0.02 ng/ml) and three different encapsulated DNA concentrations (0.01, 0.05 and 0.1 μg/ml). At the same time, the mitogenicity of the same formulation was determined in vitro using spleen cells from control mice (diluent treated group). If in vivo treatment with control lipid, or with lipid/DNA

TABLE 5

Expression of differentiation markers by spleen cells treated in vivo

| | After 18 hours | | | | After 6 days | | | |
|---|---|---|---|---|---|---|---|---|
| Formulation | CD4 | CD8 | CD22 | CD11b | CD4 | CD8 | CD22 | CD11b |
| Diluent | 22.38 | 9.47 | 57.64 | 6.02 | 25.76 | 11.33 | 57.88 | 4.19 |
| INEX324 lipid control | 19.65 | 9.32 | 57.03 | 5.32 | 25.57 | 11.62 | 57.51 | 5.33 |
| INEX324-LacZ | 30.76 | 13.51 | 52.71 | 6.31 | 21.85 | 9.65 | 42.58 | 25.10 |

Expression of differentiation markers is quantified as the percentage of positive cells in the unseparated splenic suspension.

2. Expression of Activation Markers.

The expression of activation markers was analyzed either 18 h, or six days after the last injection in vivo. The results show that there was a significant difference in their expression that was both time and treatment dependent (Table 6). The expression of activation markers was up-regulated in spleen cells from animals injected with INEX324-LacZ compared with the untreated and control lipid treated groups 18 h following treatment. As up-regulated expression of activation markers is always associated and positively correlates with the activation of immune cells, these results indicate that only lipid/DNA administration results in activation of spleen cells. However, when splenocytes were analyzed six days following the third injection, expression of activation markers in lipid/DNA treated group, returned to normal level and there was no difference between the groups. These results clearly show that activation is not induced by the repeated administration of the INEX324 TCS. In addition, activation is only detected as a transient increase in mice injected with INEX324-LacZ and is probably associated with the inflammatory properties of DODAC in the INEX324 formulation combined with potential immunogenicity of plasmid DNA.

formulation, had induced an immune stimulation, than a clone of memory cells would be generated, and in vitro restimulation of those cells with the same immunogen would result in augmented cell proliferation. The results show that when mice were primed with lipid or with lipid/DNA formulations, secondary responses to the same formulations in vitro were practically undetectable, indicative of minimal immunostimulation (Table 7).

Similar results were obtained upon in vitro stimulation of splenocytes from control mice with the same formulations, regardless of the concentrations used for stimulation none of them induced measurable mitogenic response. These results indicate that lipid and lipid/DNA formulations are not immunogenic in vivo and are not mitogenic in vitro. Stimulation of splenocytes from lipid/DNA treated group with plasmid DNA (LacZ) induced minimal, but detectable response that was not significantly different compared to those obtained from control and lipid-treated group in vitro. Stimulation of splenocytes from all experimental groups with r-β-Gal did not induce any differences in proliferative response that would correspond with the treatment in vivo. When splenocytes from all three groups were stimulated in vitro with polyclonal activator LPS (mitogen for B-cells and

TABLE 6

Expression of activation markers by spleen cells treated in vivo

| | After 18 hours | | | | After 18 hours After 6 days | | | |
|---|---|---|---|---|---|---|---|---|
| Formulation | CD54 | CD86 | MHC-II | Ly6A/E | CD54 | CD86 | MHC-II | Ly6A/E |
| Diluent | 40.14 | 1.27 | 53.97 | 1.49 | 6.18 | 0.76 | 53.16 | 1.20 |
| 324 lipid | 39.87 | 2.14 | 55.83 | 2.38 | 7.06 | 0.99 | 53.03 | 2.13 |
| 324-LacZ | 57.53 | 6.74 | 62.62 | 84.96 | 7.19 | 1.27 | 52.85 | 5.73 |

Expression of activation markers is quantified as the percentage of positive cells in the unseparated splenic suspension.

3. Influence of Repeated Administration of INEX324/DNA on Cell Proliferation.

Unseparated spleen cells, from all experimental groups, were tested in vitro for their ability to proliferate upon re-stimulation with empty INEX324 vesicles, INEX324- macrophages), again there were no measurable differences in the magnitude of proliferative response corresponding to the in vivo treatment (Table 4.). However, repeated administration of INEX324 into Balb/c mice resulted in a moderate (16%) decrease and INEX324/DNA caused a marked (40%) decrease in ConA-induced proliferation compared with diluent injected mice. ConA is a T cell mitogen, and this result indicates that repeated administration of INEX324/DNA is accompanied by a down-regulation of the splenic T cell proliferative response. The factors involved in this suppression are not completely understood, but are consistent with the reported results regarding the ability of increased number of CD11b+ cells to inhibit the proliferation of T cells in unseparated spleen cell population (Ostro MJ, TomBD/Six HR Liposomes and Immunobiology, Elsevier NH Inc., p225–239,(1980); Jaffe et al., Molecular Medicine 2, (6) 692–701, (1996)). The INEX324/DNA induced splenomegaly, increased spleen cellullarity, and five-fold increase of macrophage number observed in this study are consistent with this mechanism.

TABLE 7

Cell proliferation and cytokine release following in vitro stimulation of spleen cells.

| In vivo treatment | In vitro stimulation | $^3$H-incorporation DPMs | Cytokine release IL-2 | $(OD_{450})$ IL-4 |
|---|---|---|---|---|
| Diluent | Diluent | 1674 | 0.127 | 0.151 |
| Diluent | 324 empty vesicles | 9673 | 0.073 | 0.097 |
| Diluent | 324-LacZ | 9051 | 0.089 | 0.090 |
| Diluent | LacZ | 3352 | 0.082 | 0.095 |
| Diluent | r-β-gal | 18336 | 0.059 | 0.103 |
| Diluent | ConA | 215542 | 0.615 | 0.138 |
| Diluent | LPS | 35676 | — | — |
| 324 empty vesicles | 324 empty vesicles | 2447 | 0.083 | 0.099 |
| 324 empty vesicles | 324-LacZ | 6375 | 0.089 | 0.081 |
| 324 empty vesicles | LacZ | 3798 | 0.116 | 0.098 |
| 324 empty vesicles | r-β-gal | 16401 | 0.077 | 0.097 |
| 324 empty vesicles | ConA | 182435 | 0.569 | 0.165 |
| 324 empty vesicles | LPS | 33090 | — | — |
| 324-LacZ | 324-LacZ | 16959 | 0.103 | 0.076 |
| 324-LacZ | 324 empty vesicles | 9025 | 0.099 | 0.082 |
| 324-LacZ | LacZ | 7520 | 0.134 | 0.089 |
| 324-LacZ | r-β-gal | 13345 | 0.125 | 0.087 |
| 324-LacZ | ConA | 125450 | 0.350 | 0.157 |
| 324-LacZ | LPS | 41639 | — | — |

4. Influence of Repeated Administration of INEX324-DNA on Cytokine Release.

Splenocytes were nonstimulated, or cultured in the presence of either lipid, or various concentrations of lipid/DNA formulation, DNA, r-β-Gal, or Con A. Culture supernatants were collected at different times after culture initiation (after 24 h or 48 h), and the levels of released cytokines, IL-2 and IL-4, were measured (Table 4). Following in vivo treatment, there was no increased release of Th1 and Th2 cytokines from splenocytes of INEX324 and INEX324/DNA treated mice. TCS treated splenocytes produced IL-2 and IL-4 in levels similar to splenocytes from mice that received diluent only. Following in vivo treatment, there was also no difference in cytokine release pattern between control and lipid treated group, compared to group treated with lipid/DNA formulation. In addition, the splenocytes from all experimental groups released similar insignificant amounts of IL-2 and IL-4 after in vitro stimulation with LacZ and r-β-gal. In response to stimulation with T-cell mitogen (with a suboptimal concentration of ConA) however, unfractionated spleen cells obtained from lipid and lipid/DNA treated mice secreted markedly reduced amounts of IL-2. Splenocytes from lipid treated mice produced 25% less, and from lipid/DNA treated mice 40% less IL-2 compared with group of mice receiving diluent only (Table 4.). The decreased amounts of IL-2 release correlate with down-regulated ability of T cells to proliferate following stimulation with ConA. These results suggest that various subsets of cells of the immune system might be differentially affected by in vivo treatment with INEX324 and INEX324/DNA.

5. Effect of Repeated INEX324/DNA Administration on Production of β-gal Specific Antibodies.

Figure 29:
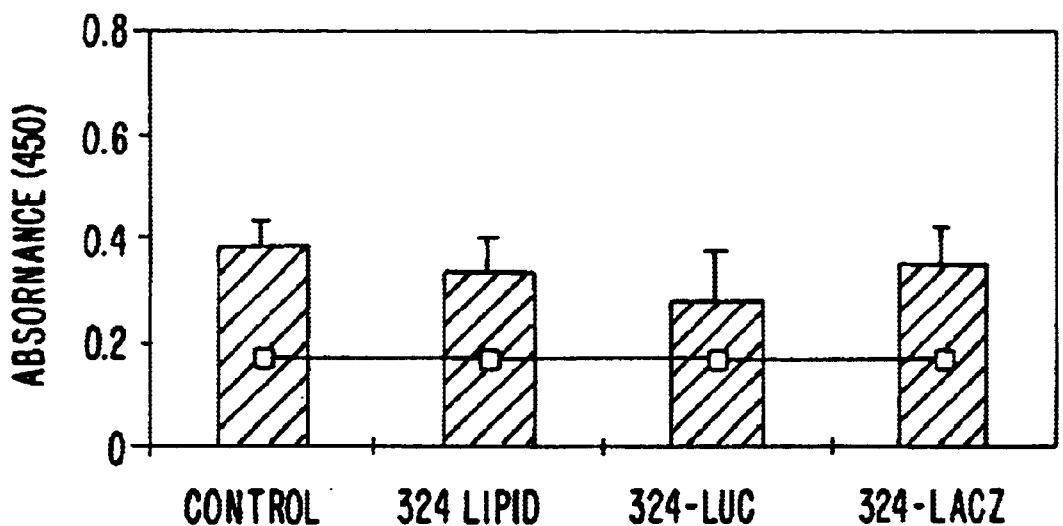
FIG. 29. Effect of repeated i.v. administration of INEX324-LacZ on serum levels of anti-β-gal antibodies. Mice received three i.v. injections of INEX324-LacZ and the level of antibodies against transgene product was measured using capture ELISA assay.

Serum samples were assayed for presence of antibodies against the transgene protein (β-gal) following third injection of lipid/LacZ formulation. Results indicate that in vivo treatment with INEX324-LacZ formulations did not elicit measurable amounts of IgM antibodies, following first injection, and IgG antibodies, after three consecutive i.v. injections (FIG. 29). The amount of IgM and IgG antibodies assayed on the same level as in a control and lipid treated group. The absence of detectable levels of anti-transgene IgG antibodies suggests that although there is measurable expression of transgene protein, the immune response against the expressed transgene protein has not been elicited.

6. Gene Expression in Vitro.

Figure 30:
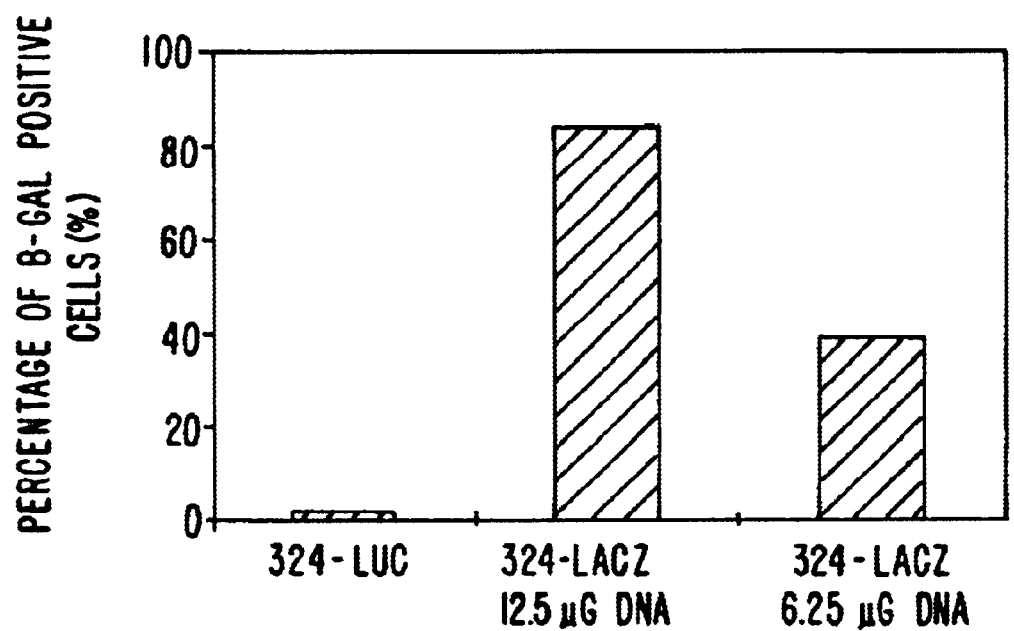
FIG. 30. Effect of DNA concentration on the expression of β-galactosidase by BHK-21 cells in vitro. Cells were incubated with either INEX324-luc or INEX324-LacZ for 24 h and expression of β-galactosidase was determined by FACS using the FDG assay.

Transfectability of the INEX324-LacZ formulation was tested in vitro. BHK cells were transduced in vitro using various concentrations (3.1, 6.2 and 12.5 µg per 1×10$^6$ cells) of INEX324-LacZ and 24 hours later the expression of β-gal was assayed by FACS. The FDG assay was developed to evaluate the establishement of stable transformed cell lines (constititively express β-gal protein) and to test the quality of pINEXLacZ plasmids. When complexes (INEX100 series TCS) were used for in vitro transfection of various cell lines, in most cases transduced cells were 60–80% positive for the expression of β-gal protein. pINEXLacZ was encapsulated in 302 and 303 vesicles and used for transfection in vitro, but the expression of the transgene protein was not detected, even though expression can be detected in vivo. Using INEX324 to encapsulate pINEXLacZ, for the first time we were able to measure gene expression in vitro. INEX324 lipid and INEX324-Luc formulation were used as negative controls. Transfection of BHK cells with INEX324-LacZ was very efficient: 85% of cells transfected with 12.5 µg of DNA and 40% of cells transfected with 6.2 µg of DNA expressed transgene β-gal protein (FIG. 30.).

7. Gene Expression in Vivo

Figure 31:
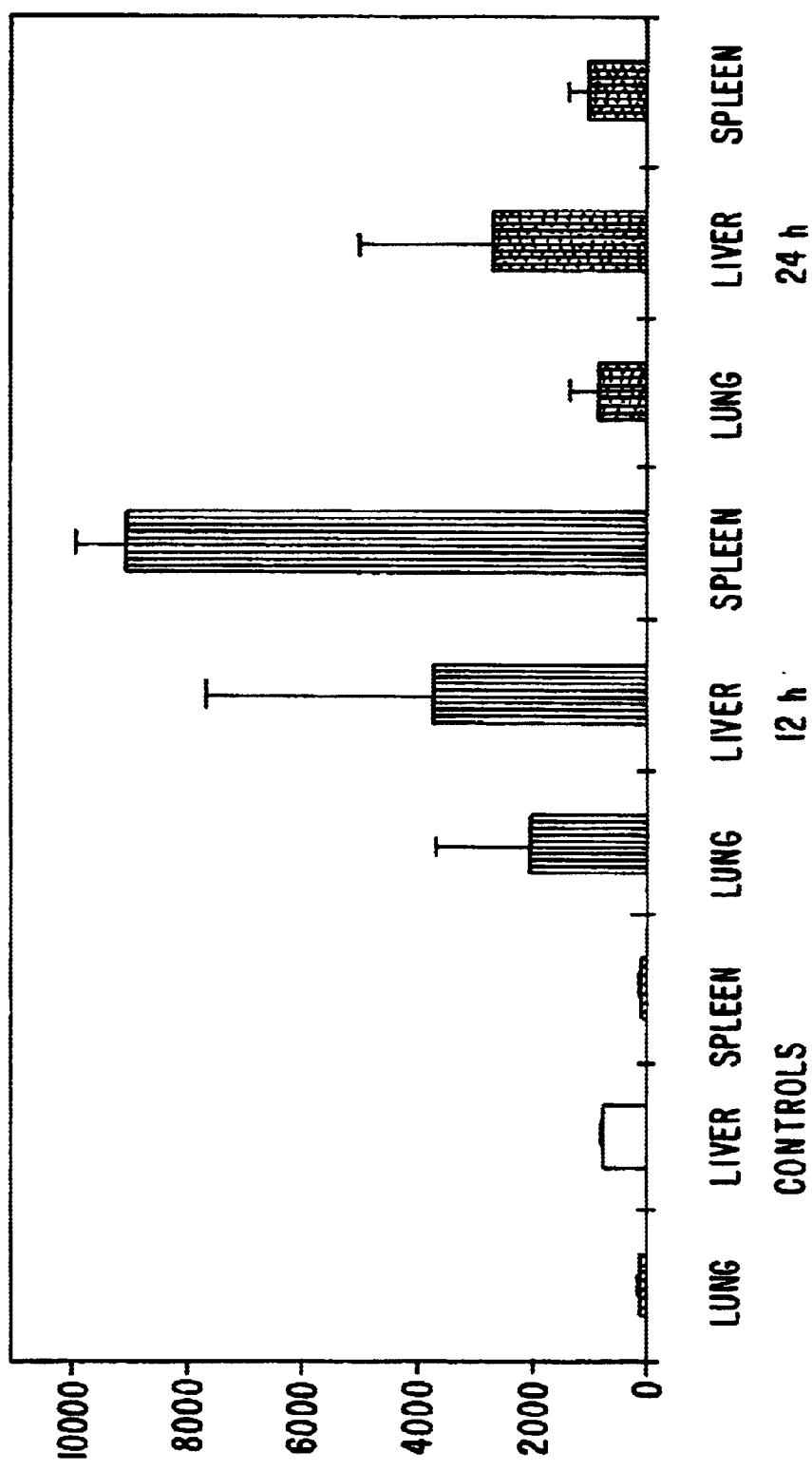
FIG. 31. Time course of luciferase expression after i.v. administration of INEX324-luc formulation. Mice were given a single i.v. injection of INEX324-luc (100 µg DNA) and the expression of luciferase was determined 12 h and 24 h post-injection.

A small-scale in vivo experiment was performed in order to determine the time course and the magnitude of gene expression following systemic (i.v.) administration of INEX324-Luc formulation. Balb/c mice (three per group) were given a single i.v. injection of INEX324-Luc (100 µg of DNA per mouse) and the expression of luciferase was determined either 12 h or 24 h post-injection. The organs (lung, liver and spleen) from both INEX324-Luc injected mice and diluent treated controls, were processed the same time and luciferase expression was evaluated. The results demonstrate that a single administration of INEX324-Luc resulted in significant gene expression in the spleen. Luciferase expression in the liver was measurable, but at a much lower level. No expression was detected in the lung. The time course of transgene expression was highest at 12 hours post injection and is still measurable at lower levels 24 hours post-injection (FIG. 31.).

Figure 32:
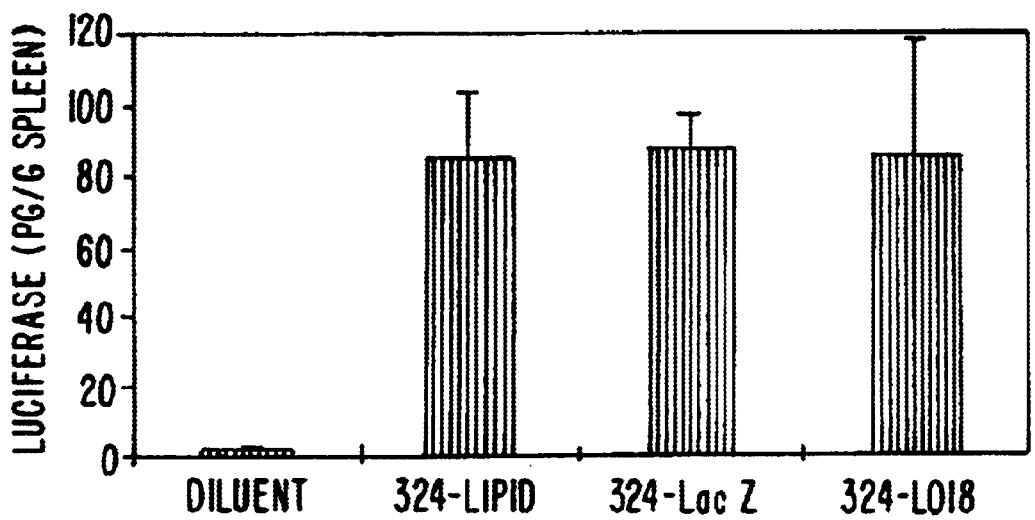
FIG. 32. Transfection of the spleen after intravenous administration of INEX324-Luc formulation. Mice received three consecutive injections of INEX324-LacZ or INEX324 lipid, followed by a single injection of INEX324-Luc. Spleens were harvested 12 h after INEX324-Luc administration and the levels of luciferase were assayed.

In the next study, Balb/c mice were given 3 intravenous injections of INEX324-LacZ or empty 324 vesicles on day 0, 7 and 14. Two weeks later the administration was repeated with INEX324-Luc (80 µg of DNA per mouse) and 12 h later the organs (liver, lung and spleen) were collected and assayed for luciferase activity. The results show that there was a significant luciferase expression in the spleen from all experimental groups (FIG. 32).

Figure 33:
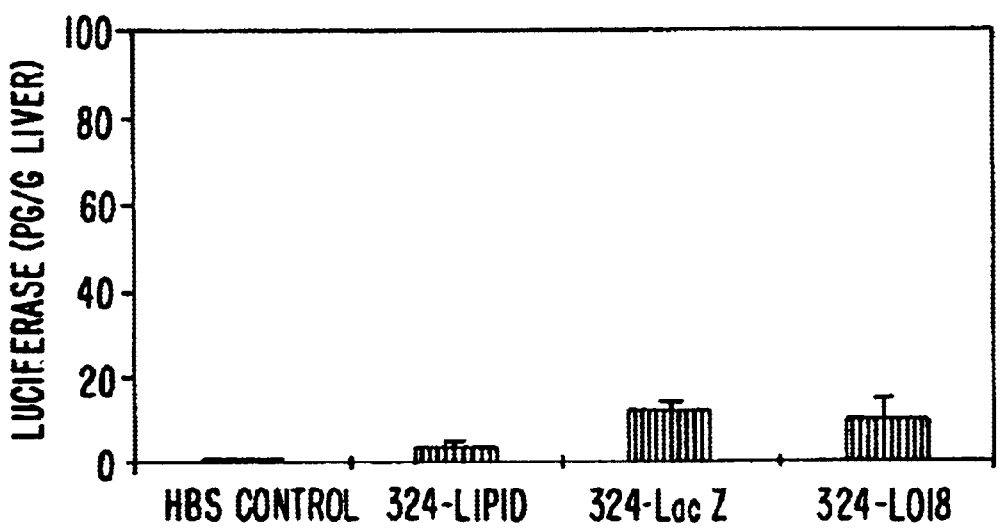
FIG. 33. Transfection of the liver after intravenous administration of INEX324-Luc formulation. Mice received three consecutive injections of INEX324-LacZ or 324 lipid, followed by single injection of INEX324-Luc. Livers were harvested 12 h after INEX324-Luc administration and the levels of luciferase were assayed.

Previous in vivo treatment with INEX324 empty vesicles or INEX324-LacZ formulation, did not result in decreased gene expression in the spleen, luciferase expression in both groups assayed at levels similar to that from control group. Although the level of gene expression in the liver was much lower, it demonstrates the same pattern as in the spleen confirming that previous in vivo treatment did not compromise the ability of TCS to deliver gene of interest (FIG. 33.). There was no measurable gene expression in the lungs from any of the groups tested (results not shown).

VIII. CONCLUSION

As discussed above, in accordance with one of its aspects, the present invention provides compositions and methods for preparing serum-stable nucleic acid (e.g., plasmid)-lipid particles which are useful for the transfection of cells, both in vitro and in vivo.

Still further, nucleic acids (e.g., plasmid DNA) can now be formulated using a variety of lipids to provide compositions having extremely high plasmid/lipid ratios. The process can be performed in a predictable manner, by generating theoretical curves for any set of lipids, whereby accurate predictions of the salt concentration necessary to achieve a serum stable formulation can be made.

Still further, nucleic acids (e.g., plasmid DNA) can be formulated using a variety of lipids to provide compositions that can be administered in repeat doses without eliciting an immune response, while still maintaining gene expression.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method of encapsulating a nucleic acid in a lipid bilayer carrier, said method comprising:
   (a) combining said nucleic acid with a lipid-detergent mixture, said lipid-detergent mixture comprising a lipid mixture of an aggregation-preventing agent in an amount of about 5 mol % to about 20 mol %, a cationic lipid in an amount of about 0.5 mol % to about 50 mol %, and a flisogenic lipid and a detergent, to provide a nucleic acid-lipid detergent mixture; and
   (b) dialyzing said nucleic acid-lipid-detergent mixture against a buffered salt solution to remove said detergent and to encapsulate said nucleic acid in a lipid bilayer carrier and provide a lipid bilayer-nucleic acid composition, wherein said buffered salt solution has an ionic strength sufficient to encapsulate of from about 40% to about 80% of said nucleic acid.

2. The method in accordance with claim 1, further comprising (c) removing substantially all of the unencapsulated nucleic acids to provide a purified lipid bilayer-nucleic acid composition having from about 20 μg to about 400 μg of nucleic acid per about 1 mg of lipid.

3. The method in accordance with claim 1, wherein said nucleic acid is a plasmid.

4. The method in accordance with claim 1, wherein said detergent is octylglucoside.

5. The method in accordance with claim 1, wherein said cationic lipid is DODAC.

6. The method in accordance with claim 1, wherein said aggregation-preventing agent is a member selected from the group consisting of gangliosides, ATTA-lipids and PEG-lipids.

7. The method in accordance with claim 6, wherein said aggregation-preventing agent is a PEG-lipid.

8. The method in accordance with claim 7, wherein said PEG-lipid is a PEG-ceramide.

9. The method in accordance with claim 8, wherein said PEG-ceramide is selected from the group consisting of PEG-Cer-C8, PEG-Cer-C 14 and PEG-Cer-C20.

10. The method in accordance with claim 1, wherein said buffered salt solution is HEPES-buffered NaCl solution.

11. The method in accordance with claim 1, wherein said buffered salt solution is a citrate solution.

12. The method in accordance with claim 1, wherein said buffered salt solution contains about 150 mM NaCl.

13. The method in accordance with claim 1, wherein about 50% to about 70% of the initial concentration of said nucleic acid becomes encapsulated.

14. The method in accordance with claim 8, wherein said cationic lipid is DODAC, said PEG-ceramide is selected from the group consisting of PEG-Cer-C8, PEG-Cer-C14 and PEG-Cer-C20, said fusogenic lipid comprises DOPE and said buffered salt solution comprises NaCl and sodium phosphate.

15. The method in accordance with claim 1, wherein the lipid bilayer carrier-encapsulated nucleic acid formed has a mean particle diameter of from about 50 nm to about 150 nm in the absence of extrusion or sonication.

16. The method in accordance with claim 1, wherein the lipid bilayer carrier-encapsulated nucleic acid formed has a mean particle diameter of from about 50 nm to about 90 nm in the absence of extrusion or sonication.

17. A method for introducing a nucleic acid into a cell, said method comprising:
   (a) preparing a lipid-nucleic acid composition according to claim 1; and
   (b) contacting said cell with said lipid-nucleic acid composition for a period of time sufficient to introduce said nucleic acid into said cell.

18. The method in accordance with claim 17, wherein said cell is a spleen cell.

19. The method in accordance with claim 17, wherein the efficiency of transfection is not diminished by repeat doses administered within 2 weeks.

* * * * *